(12) United States Patent
Krawczyk et al.

(10) Patent No.: US 10,287,571 B2
(45) Date of Patent: May 14, 2019

(54) GENETICALLY MODIFIED MICROORGANISM FOR IMPROVED PRODUCTION OF FINE CHEMICALS ON SUCROSE

(71) Applicant: BASF SE, Ludwigshafen (DE)

(72) Inventors: Joanna Martyna Krawczyk, Biberach (DE); Stefan Haefner, Speyer (DE); Hartwig Schroeder, Nußloch (DE); Oskar Zelder, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/308,874

(22) PCT Filed: May 7, 2015

(86) PCT No.: PCT/EP2015/060102
§ 371 (c)(1),
(2) Date: Nov. 4, 2016

(87) PCT Pub. No.: WO2015/169920
PCT Pub. Date: Nov. 12, 2015

(65) Prior Publication Data
US 2017/0073665 A1   Mar. 16, 2017

(30) Foreign Application Priority Data

May 8, 2014  (EP) .................... 14167488

(51) Int. Cl.
*A61K 38/00* (2006.01)
*C12N 15/10* (2006.01)
*C12P 7/46* (2006.01)
*C07K 14/195* (2006.01)
*C12N 15/74* (2006.01)

(52) U.S. Cl.
CPC .......... *C12N 15/102* (2013.01); *C07K 14/195* (2013.01); *C12N 15/74* (2013.01); *C12P 7/46* (2013.01); *C12Y 207/11* (2013.01); *C12N 2510/02* (2013.01)

(58) Field of Classification Search
CPC ................................ A61K 38/00; C12Q 1/48
USPC .................................. 435/15, 252.3
See application file for complete search history.

(56) References Cited

U.S. PATENT DOCUMENTS

2016/0244777 A1* 8/2016 Coffin ............... C12N 15/8274

FOREIGN PATENT DOCUMENTS

| WO | WO-2009/024294 A1 | 2/2009 |
| WO | WO-2010/092155 A1 | 8/2010 |
| WO | WO-2010/115067 A2 | 10/2010 |
| WO | WO-2011/063157 A2 | 5/2011 |
| WO | WO-2012/031079 A2 | 3/2012 |
| WO | WO-2013/003432 A1 | 1/2013 |
| WO | WO-2014/066235 A1 | 5/2014 |

OTHER PUBLICATIONS

International Preliminary Report on Patentability (Chapter II), International Application No. PCT/EP2015/060102, dated Jun. 10, 2016.
International Search Report and Written Opinion, International Application No. PCT/EP2015/060102, dated Oct. 5, 2015.
Zhang et al., Reengineering *Escherichia coli* for Succinate Production in Mineral Salts Medium, Appl. Environ. Microbiol., 75(24):7807-13.

* cited by examiner

*Primary Examiner* — Tekchand Saidha
(74) *Attorney, Agent, or Firm* — Marshall, Gerstein & Borun LLP

(57) ABSTRACT

The present invention relates to a modified microorganism having, compared to its wildtype, —a reduced activity of an enzyme encoded by the ptsA-gene, —a reduced activity of an enzyme encoded by the ptsH-gene or —a reduced activity of an enzyme encoded by the ptsA-gene and a reduced activity of an enzyme encoded by the ptsH-gene, wherein the wildtype from which the modified microorganism has been derived belongs to the family of Pasteurellaceae. The present invention also relates to a method for producing succinic acid and to the use of modified microorganisms.

8 Claims, 7 Drawing Sheets
Specification includes a Sequence Listing.

GENETICALLY MODIFIED MICROORGANISM FOR IMPROVED PRODUCTION OF FINE CHEMICALS ON SUCROSE

This application is a National Stage application of International Application No. PCT/EP2015/060102, filed May 7, 2015, which claims priority under 35 U.S.C. § 119 to European Patent Application No. 14167488.7, which was filed on May 8, 2014.

INCORPORATION BY REFERENCE OF MATERIAL SUBMITTED ELECTRONICALLY

This application incorporates by reference in its entirety a computer-readable nucleotide/amino acid sequence listing identified as one 103,895 byte ASCII (text) file named "H78475_Seqlisting.txt," created Nov. 1, 2016.

The present invention relates to a modified microorganism, to a method for producing an organic compound and to the use of a modified microorganism.

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the IdhA-gene and/or the pflD- or the pflA-gene have been disrupted, are disclosed in WO-A-2010/092155, these mutant strains being characterized by a significantly increased production of succinic acid from carbon sources such as glycerol or mixtures of glycerol and carbohydrates such as maltose, under anaerobic conditions compared to the DD1-wildtype disclosed in WO-A-2009/024294.

However, bio-based succinate still faces the challenge of becoming cost competitive against petrochemical-based alternatives. In order to develop the bio-based industrial production of succinic acid, it will be important to grow the cells in a low cost medium, and the working strain optimally should be able to metabolize a wide range of low-cost sugar feedstock to produce succinic acid in good yields so that the cheapest available raw materials can be used.

Sucrose (commonly known as sugar) is a disaccharide consisting of glucose and fructose, and it is a carbon source that is very abundant in nature and is produced from all plants having photosynthesis ability. Particularly, sugarcane and sugar beet contain large amounts of sucrose, and more than 60% of the world's sucrose is currently being produced from sugarcane. Particularly, sucrose is produced at a very low cost, because it can be industrially produced through a simple process of evaporating/concentrating extracts obtained by mechanical pressing of sugarcanes. Sucrose as a raw material for producing chemical compounds through microbial fermentation is thus inexpensive and it also functions to protect the cell membrane from an external environment containing large amounts of desired metabolites, thus producing high-concentrations of desired metabolites as shown by Kilimann et al. (*Biochimica et Biophysica Acta*, 1764, 2006).

Even though sucrose is an excellent raw material having the above-described advantages, including low price and a function to protect microorganisms from an external environment, the disadvantage of this carbon source can be seen in the fact a large number of microorganisms do not have a complete mechanism of transporting sucrose into cell, degrading the transported sucrose and linking the degraded products to glycolysis, and thus cannot use sucrose as a carbon source. Even in the case of microorganisms having a mechanism capable of using sucrose, they cannot efficiently produce desired metabolites, because the rate of ingestion and degradation of sucrose as a carbon source is very low.

It was therefore an object of the present invention to overcome the disadvantages of the prior art.

In particular, it was an object of the present invention to provide microorganisms which can be used for the fermentative production of organic compounds such as succinic acid and that can efficiently utilize sucrose as the predominant carbon source without sacrificing growth rates or yields. Preferably said microorganisms would be able to use a number of low cost carbon sources and produce excellent yields of organic compounds such as succinic acid. Compared to the recombinant microorganisms of the prior art that are used for the fermentative production of succinic acid, the microorganisms of the present invention should be characterized by an increased succinic acid yield and an increased carbon yield during growth of the cells on sucrose as the predominant carbon source.

A contribution to achieving the abovementioned aims is provided by a modified microorganism having, compared to its wildtype, having, compared to its wildtype, a reduced activity of an enzyme encoded by the ptsA-gene, a reduced activity of an enzyme encoded by the ptsH-gene or a reduced activity of an enzyme encoded by the ptsA-gene and a reduced activity of an enzyme encoded by the ptsH-gene wherein the wildtype from which the modified microorganism has been derived belongs to the family of Pasteurellaceae.

A contribution to achieving the abovementioned aims is in particular provided by a modified microorganism which
the ptsA-gene or parts thereof,
the ptsH-gene or parts thereof, or
the ptsA-gene or parts thereof and the ptsH-gene or parts thereof have been deleted or in which a regulatory element of these genes or at least a part thereof has been deleted or in which at least one mutation has been introduced into these genes, wherein the wildtype from which the modified microorganism has been derived belongs to the family of Pasteurellaceae.

Surprisingly, it has been discovered that a reduction of the activity of the enzyme that is encoded by the ptsA-gene (this enzyme being the energy coupling Enzyme I of the phosphoenolpyruvate-dependent phosphotransferase system) and/or a reduction of the activity of the enzyme that is encoded by the ptsH-gene (this enzyme being the histidine-containing protein HPr of the phosphoenolpyruvate-dependent phosphotransferase system), for example by a deletion of the ptsA-gene or parts thereof and/or the ptsH-gene or parts thereof, in a microorganism that belongs to the family of Pasteurellaceae results in a modified microorganism that, compared to the corresponding microorganism in which the activity of this enzyme or these enzymes has not been decreased, is characterized by an increased yield of organic compounds such as succinic acid, especially if these modified microorganisms are grown on sucrose as the assimilable carbon source. This is indeed surprising as in microorganisms that belong to the family of Pasteurellaceae, such as those of the genus *Basfia*, in particular those of the species *Basfia succiniciproducens*, the phosphoenolpyruvate-dependent phosphotransferase system (i.e. the PTS-system) is responsible of the uptake of fructose into the cells. When *Basfia*-strains are cultured on sucrose, the disaccharide is hydrolyzed inside the cell to obtain glucose-6-phosphat and fructose. Fructose, however, is secreted after hydrolysis and is taken up again by the cell using the fructose PTS-system. The person skilled in the art would therefore have assumed that an inactivation of the ptsA-gene and/or the ptsH-gene, which results in an inactivation of the PTS-system, would lead to a decreased formation of succinic acid when the cells are cultured on sucrose as the predominant carbon source as at least a part of the disaccharide (i.e. fructose) can not be imported into the cell.

In context with the expression "a modified microorganism having, compared to its wildtype, a reduced activity of the enzyme that is encoded by the x-gene", wherein the x-gene is the ptsA-gene or the ptsH-gene and optionally, as described later, the ldhA-gene, the pflA-gene, the pflD-gene, the wcaJ-gene and/or the pykA-gene, the term "wildtype" refers to a microorganism in which the activity of the enzyme that is encoded by the x-gene has not been decreased, i.e. to a microorganism whose genome is present in a state as before the introduction of a genetic modification of the x-gene. Preferably, the expression "wildtype" refers to a microorganism (e.g., bacteria, yeast cell, fungal cell, etc.) whose genome, in particular whose x-gene, is present in a state as generated naturally as the result of evolution. The term is used both for the entire microorganism and for individual genes. As a consequence, the term "wildtype" preferably does not cover in particular those microorganisms, or those genes, whose gene sequences have at least in part been modified by man by means of recombinant methods. The term "modified microorganism" thus includes a microorganism which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring wildtype microorganism from which it was derived. According to a particular preferred embodiment of the modified microorganism according to the present invention the modified microorganism is a recombinant microorganism, which means that the microorganism has been obtained using recombinant DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

The wildtype from which the microorganisms according to the present invention are derived belongs to the family of Pasteurellaceae. Pasteurellaceae comprise a large family of Gram-negative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related *Enterobacteriaceae* by the presence of oxidase, and from most other similar bacteria by the absence of flagella. Bacteria in the family Pasteurellaceae have been classified into a number of genera based on metabolic properties and there sequences of the 16S RNA and 23S RNA. Many of the Pasteurellaceae contain pyruvate-formate-lyase genes and are capable of anaerobically fermenting carbon sources to organic acids.

According to a particular preferred embodiment of the modified microorganism according to the present invention the wildtype from which the modified microorganism has been derived belongs to the genus *Basfia* and it is particularly preferred that the wildtype from which the modified microorganism has been derived belongs to the species *Basfia succiniciproducens*.

Most preferably, the wildtype from which the modified microorganism according to the present invention as been derived is *Basfia succiniciproducens*-strain DD1 deposited under the Budapest Treaty with DSMZ (Deutsche Sammlung von Mikroorganismen und Zellkulturen GmbH, Inhoffenstr. 7B, D-38124 Braunschweig, Germany), Germany, having the deposit number DSM 18541 that has been deposited on Aug. 11, 2006. This strain has been originally isolated from the rumen of a cow of German origin. Pasteurella bacteria can be isolated from the gastrointestinal tract of animals and, preferably, mammals. The bacterial strain DD1, in particular, can be isolated from bovine rumen and is capable of utilizing glycerol (including crude glycerol) as a carbon source. Further strains of the genus *Basfia* that can be used for preparing the modified microorganism according to the present invention are the *Basfia*-strain that is commercially available from the Deutsche Sammlung von Mikroorganismen und Zellkulturen GmbH under DSM number 22022 or the *Basfia*-strains that have been deposited with the Culture Collection of the University of Göteborg (CCUG, University of Gothenburg, Department of Clinical Bacteriology, Guldhedsgatan 10, SE-413 46 Göteborg), Sweden, having the deposit numbers CCUG 57335, CCUG 57762, CCUG 57763, CCUG 57764, CCUG 57765 or CCUG 57766 on Feb. 27, 2009. Said strains have been originally isolated from the rumen of cows of German or Swiss origin.

In this context it is particularly preferred that the wildtype from which the modified microorganism according to the present invention has been derived has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the wildtype from which the modified microorganism according to the present invention has been derived has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, http://emboss.source-forge.net/what/) with the default parameters which are, i.e. gap open (penalty to open a gap): 10.0, gap extend (penalty to extend a gap): 0.5, and data file (scoring matrix file included in package): EDNAFUL.

It should be noted that the modified microorganism according to the present invention can not only be derived from the above mentioned wildtype-microorganisms, especially from *Basfia succiniciproducens*-strain DD1, but also from variants of these strains. In this context the expression "a variant of a strain" comprises every strain having the same or essentially the same characteristics as the wildtype-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wildtype from which the variant has been derived. A variant of a strain in the sense of this definition can, for example, be obtained by treating the wildtype-strain with a mutagenizing chemical agent, X-rays, or UV light.

The modified microorganism according to the present invention is characterized in that it has, compared to its wildtype, a reduced activity of an enzyme encoded by the ptsA-gene, a reduced activity of an enzyme encoded by the ptsH-gene or a reduced activity of an enzyme encoded by the ptsA-gene and a reduced activity of an enzyme encoded by the ptsH-gene.

The reduction of the enzyme activity ($\Delta_{activity}$) is defined as follows:

$$\Delta_{activity} = 100\% - \left(\frac{\text{activity of the modified microorganism}}{\text{activity of the } wildtype} \times 100\%\right)$$

wherein, when determining $\Delta_{activity}$, the activity in the wildtype and the activity in the modified microorganism are determined under exactly the same conditions. Methods for the detection and determination of the activity of the enzyme that is encoded by the ptsA-gene and the ptsH-gene can be found, for example, in Reizer et al.: "*Evidence for the presence of heat-stable protein (HPr) and ATP-dependent HPr kinase in heterofermentative lactobacilli lacking phosphoenolpyruvate:glycose phosphotransferase activity*"; *Proc. Nadl. Acad. Sci. USA*; Vol. 85, pages 2041-2045 (1988).

The reduced activity of the enzymes disclosed herein, in particular the reduced activity of the enzyme encoded by the ptsA-gene and/or the ptsH-gene, the ldhA-gene, the pflA-gene, the pflD-gene and/or the wcaJ-gene, can be a reduction of the enzymatic activity by at least 50%, compared to the activity of said enzyme in the wildtype of the microorganism, or a reduction of the enzymatic activity by at least 90%, or more preferably a reduction of the enzymatic activity by at least 95%, or more preferably a reduction of the enzymatic activity by at least 98%, or even more preferably a reduction of the enzymatic activity by at least 99% or even more preferably a reduction of the enzymatic activity by at least 99.9%. In case of the pykA-gene the reduced activity is preferably a reduction of the enzymatic activity by 0.1 to 99%, compared to the activity of said enzyme in the wildtype of the microorganism, or a reduction of the enzymatic activity by at least 15%, or at least 25%, or at least 35%, or at least 45%, or at least 55%, or at least 65%, or at least 75% or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%. Preferably, the reduction of the activity of the enzyme encoded by the pykA-gene is in the range of 15 to 99%, more preferably in the range of 50 to 95% and even more preferably in the range of 90 to 99%. The term "reduced activity of the enzyme that is encoded by the x-gene" also encompasses a modified microorganism which has no detectable activity of this particular enzyme.

The term "reduced activity of an enzyme" includes, for example, the expression of the enzyme by said genetically manipulated (e.g., genetically engineered) microorganism at a lower level than that expressed by the wildtype of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

Microorganisms having a reduced activity of the enzyme encoded by the ptsA-gene and/or the ptsH-gene may occur naturally, i.e. due to spontaneous mutations. A microorganism can be modified to lack or to have significantly reduced activity of the enzyme that is encoded by the ptsA-gene and/or the ptsH-gene by various techniques, such as chemical treatment or radiation. To this end, microorganisms will be treated by, e.g., a mutagenizing chemical agent, X-rays, or UV light. In a subsequent step, those microorganisms which have a reduced activity of the enzyme that is encoded by the ptsA-gene and/or by the ptsH-gene will be selected. Modified microorganisms are also obtainable by homologous recombination techniques which aim to mutate, disrupt or excise the ptsA-gene and/or the ptsH-gene in the genome of the microorganism or to substitute the gene with a corresponding gene that encodes for an enzyme which, compared to the enzyme encoded by the wildtype-gene, has a reduced activity.

According to a preferred embodiment of the modified microorganism according to the present invention, a reduction of the activity of the enzyme encoded by the ptsA-gene and/or by the ptsH-gene is achieved by a modification of the ptsA-gene and the ptsH-gene, respectively, wherein this gene modification is preferably realized by a deletion of the ptsA-gene and/or the ptsH-gene or at least a part of these gene, a deletion of a regulatory element of the ptsA-gene and/or the ptsH-gene or parts of these regulatory elements, such as a promotor sequence, or by an introduction of at least one mutation into the ptsA-gene and/or into the ptsH-gene.

In the following, a suitable technique for recombination, in particular for introducing a mutation or for deleting sequences, is described.

This technique is also sometimes referred to as the "Campbell recombination" herein (Leen-houts et al., *Appl Env Microbiol.* (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

The ptsA-gene the activity of which is reduced in the modified microorganism according to the present invention preferably comprises a nucleic acid selected from the group consisting of:

a1) nucleic acids having the nucleotide sequence of SEQ ID NO: 3;
b1) nucleic acids encoding the amino acid sequence of SEQ ID NO: 4;
c1) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a1) or b1), the identity being the identity over the total length of the nucleic acids of a1) or b1);
d1) nucleic acid encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a1) or b1), the identity being the identity over the total length of amino acid sequence encoded by the nucleic acids of a1) or b1)

e1) nucleic acids capable of hybridizing under stringent conditions with a complementary sequence of any of the nucleic acids according to a1) or b1); and f1) nucleic acids encoding the same protein as any of the nucleic acids of a1) or b1), but differing from the nucleic acids of a1) or b1) above due to the degeneracy of the genetic code.

The ptsH-gene the activity of which is reduced in the modified microorganism according to the present invention preferably comprises a nucleic acid selected from the group consisting of:

a2) nucleic acids having the nucleotide sequence of SEQ ID NO: 5;

b2) nucleic acids encoding the amino acid sequence of SEQ ID NO: 6;

c2) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a2) or b2), the identity being the identity over the total length of the nucleic acids of a2) or b2);

d2) nucleic acid encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a2) or b2), the identity being the identity over the total length of amino acid sequence encoded by the nucleic acids of a2) or b2)

e2) nucleic acids capable of hybridizing under stringent conditions with a complementary sequence of any of the nucleic acids according to a2) or b2); and f2) nucleic acids encoding the same protein as any of the nucleic acids of a2) or b2), but differing from the nucleic acids of a2) or b2) above due to the degeneracy of the genetic code.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M Na—PO4, 1 mM EDTA at 50° C. with washing in 0.1×SSC, 0.1% SDS at 50° C. or 65° C., preferably 65° C. Preferably, the complementary nucleotides hybridize with a fragment or the whole wcaJ nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The ptsA-gene and/or the ptsH-gene or parts of these genes that may be deleted by the above mentioned "Campbell recombination" or in which at least one mutation is introduced by the above mentioned "Campbell recombination" preferably comprises a nucleic acid as defined above.

Nucleic acid having the nucleotide sequence of SEQ ID NO: 3 and SEQ ID NO: 5 correspond to the ptsA-gene and the ptsH-gene of *Basfia succiniciproducens*-strain DD1.

According to a preferred embodiment of the modified microorganism according to the present invention, this microorganism is not only characterized by a reduced activity of the enzyme encoded by the ptsA-gene and/or the ptsH-gene, but also, compared to the wildtype, by at least one of the following properties:

i) a reduced pyruvate formate lyase activity;
ii) a reduced lactate dehydrogenase activity;
iii) a reduced activity of an enzyme encoded by the wcaJ-gene;
iv) a reduced activity of an enzyme encoded by the pykA-gene.

In this context particularly preferred modified microorganism are those having the following properties or combination of properties: i), ii), iii), iv), i)ii), i)iii), i)iv), ii)iii), ii)iv), iii)iv), i)ii)iii), i)ii)iv), i)iii)iv), ii)iii)iv) and i)ii)iii)iv), wherein a modified microorganism that is characterized by properties i), ii), iii) and iv) is most preferred.

Modified microorganisms being deficient in lactate dehydrogenase and/or being deficient in pyruvate formate lyase activity are disclosed in WO-A-2010/092155, US 2010/0159543 and WO-A-2005/052135, the disclosure of which with respect to the different approaches of reducing the activity of lactate dehydrogenase and/or pyruvate formate lyase in a microorganism, preferably in a bacterial cell of the genus Pasteurella, particular preferred in *Basfia succinicip-*

*roducens* strain DD1, is incorporated herein by reference. Methods for determining the pyruvate formate lyase activity are, for example, disclosed by Asanuma N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777 and methods for determining the lactate dehydrogenase activity are, for example, disclosed by Bergmeyer, H. U., Bergmeyer J. and Grassi, M. (1983-1986) in "*Methods of Enzymatic Analysis*", 3rd Edition, Volume III, pages 126-133, Verlag Chemie, Weinheim.

In this context it is preferred that the reduction of the activity of lactate dehydrogenase is achieved by an inactivation of the IdhA-gene (which encodes the lactate dehydrogenase; LdhA; EC 1.1.1.27 or EC 1.1.1.28) and the reduction of the pyruvate formate lyase is achieved by an inactivation of the pflA-gene (which encodes for an activator of pyruvate formate lyase; PflA; EC 1.97.1.4) or the pflD-gene (which encodes the pyruvate formate lyase; PflD; EC 2.3.1.54), wherein the inactivation of these genes (i.e. IdhA, pflA and pflD) is preferably achieved by a deletion of theses genes or parts thereof, by a deletion of a regulatory element of these genes or at least a part thereof of by an introduction of at least one mutation into these genes, particular preferred by means of the "Campbell recombination" as described above.

A reduction of the activity of the enzyme encoded by the wcaJ-gene is preferably achieved by a modification of the wcaJ-gene, wherein this gene modification is preferably realized by a deletion of the wcaJ-gene or at least a part thereof, a deletion of a regulatory element of the wcaJ-gene or at least a part thereof, such as a promotor sequence, or by an introduction of at least one mutation into the wcaJ-gene. In context with the introduction of at least one mutation into the wcaJ-gene it is particularly preferred that the at least one mutation leads to the expression of a truncated enzyme encoded by the wcaJ-gene. It is furthermore preferred that in the truncated enzyme at least 100 amino acids, preferably at least 125 amino acids, more preferred at least 150 amino acids and most preferred at least 160 amino acids of the wildtype enzyme encoded by the wcaJ-gene are deleted from the C-terminal end. Such a truncated enzyme encoded the wcaJ-gene can, for example, be obtained by inserting or deleting nucleotides at appropriate positions within the wcaJ-gene which leads to a frame shift mutation, wherein by means of this frame shift mutation a stop codon introduced. For example, insertion of a nucleotide in the codon that encodes of lysine between thymine at position 81 and adenine at position 82 leads to a frame shift mutation by means of which a stop codon is introduced as shown in SEQ ID NO: 13. Such mutations of the wcaJ-gene can be introduced, for example, by site-directed or random mutagenesis, followed by an introduction of the modified gene into the genome of the microorganism by recombination. Variants of the wcaJ-gene can be are generated by mutating the wcaJ-gene sequence SEQ ID NO: 13 by means of PCR. The "Quickchange Site-directed Mutagenesis Kit" (Stratagene) can be used to carry out a directed mutagenesis. A random mutagenesis over the entire coding sequence, or else only part thereof, of SEQ ID NO: 13 can be performed with the aid of the "GeneMorph II Random Mutagenesis Kit" (Stratagene).

A reduction of the activity of the enzyme encoded by the pykA-gene is preferably achieved by introducing at least one mutation into the pykA-gene, preferably into the wildtype-pykA-gene. In this context it is particularly preferred that the at least one mutation leads to a modification of the nucleic acid sequence of the pykA-gene, such that the amino acid sequence of the enzyme encoded by the modified gene differs from the amino acid sequence of the enzyme encoded by the wildtype pykA-gene in at least one amino acid. A mutation into the pykA-gene can be introduced, for example, by site-directed or random mutagenesis, followed by an introduction of the modified gene into the genome of the microorganism by recombination. Variants of the pykA-gene can be are generated by mutating the gene sequence SEQ ID NO: 15 by means of PCR. The "Quickchange Site-directed Mutagenesis Kit" (Stratagene) can be used to carry out a directed mutagenesis. A random mutagenesis over the entire coding sequence, or else only part thereof, of SEQ ID NO: 15 can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

The IdhA-gene the activity of which may be reduced in the modified microorganism according to the present invention preferably comprises a nucleic acid selected from the group consisting of:

α1) nucleic acids having the nucleotide sequence of SEQ ID NO: 7;

α2) nucleic acids encoding the amino acid sequence of SEQ ID NO: 8;

α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2);

α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2);

α5) nucleic acids capable of hybridizing under stringent conditions with a complementary sequence of any of the nucleic acids according to α1) or α2); and α6) nucleic acids encoding the same protein as any of the nucleic acids of α1) or α2), but differing from the nucleic acids of α1) or α2) above due to the degeneracy of the genetic code.

Nucleic acid having the nucleotide sequence of SEQ ID NO: 7 correspond to the Idh-gene of *Basfia succiniciproducens*-strain DD1.

The pflA-gene the activity of which may be reduced in the modified microorganism according to the present invention preferably comprises a nucleic acid selected from the group consisting of:

β1) nucleic acids having the nucleotide sequence of SEQ ID NO: 9;

β2) nucleic acids encoding the amino acid sequence of SEQ ID NO: 10;

β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1) or β2), the identity being the identity over the total length of the nucleic acids of β1) or β2);

β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of β1) or β2), the identity being the identity over the total length of amino acid sequence encoded by the nucleic acids of β1) or β2);

β5) nucleic acids capable of hybridizing under stringent conditions with a complementary sequence of any of the nucleic acids according to β1) or β2); and β6) nucleic acids encoding the same protein as any of the nucleic acids of β1) or β2), but differing from the nucleic acids of β1) or β2) above due to the degeneracy of the genetic code.

Nucleic acid having the nucleotide sequence of SEQ ID NO: 9 correspond to the pflA-gene of *Basfia succiniciproducens*-strain DD1.

The pflD-gene the activity of which may be reduced in the modified microorganism according to the present invention preferably comprises a nucleic acid selected from the group consisting of:

γ1) nucleic acids having the nucleotide sequence of SEQ ID NO: 11;

γ2) nucleic acids encoding the amino acid sequence of SEQ ID NO: 12;

γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2);

γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2);

γ5) nucleic acids capable of hybridizing under stringent conditions with a complementary sequence of any of the nucleic acids according to γ1) or γ2); and γ6) nucleic acids encoding the same protein as any of the nucleic acids of γ1) or γ2), but differing from the nucleic acids of γ1) or γ2) above due to the degeneracy of the genetic code.

Nucleic acid having the nucleotide sequence of SEQ ID NO: 11 correspond to the pflD-gene of *Basfia succiniciproducens*-strain DD1.

The wcaJ-gene the activity of which may be reduced in the modified microorganism according to the present invention preferably comprises a nucleic acid selected from the group consisting of:

δ1) nucleic acids having the nucleotide sequence of SEQ ID NO: 13;

δ2) nucleic acids encoding the amino acid sequence of SEQ ID NO: 14;

δ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of δ1) or δ2), the identity being the identity over the total length of the nucleic acids of δ1) or δ2);

δ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of δ1) or δ2), the identity being the identity over the total length of amino acid sequence encoded by the nucleic acids of δ1) or δ2);

δ5) nucleic acids capable of hybridizing under stringent conditions with a complementary sequence of any of the nucleic acids according to δ1) or δ2); and δ6) nucleic acids encoding the same protein as any of the nucleic acids of δ1) or δ2), but differing from the nucleic acids of δ1) or δ2) above due to the degeneracy of the genetic code.

Nucleic acid having the nucleotide sequence of SEQ ID NO: 13 correspond to the wcaJ-gene of *Basfia succiniciproducens*-strain DD1.

The pykA-gene the activity of which may be reduced in the modified microorganism according to the present invention preferably comprises a nucleic acid selected from the group consisting of:

ε1) nucleic acids having the nucleotide sequence of SEQ ID NO: 15;

ε2) nucleic acids encoding the amino acid sequence of SEQ ID NO: 16;

ε3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of ε1) or ε2), the identity being the identity over the total length of the nucleic acids of ε1) or ε2);

ε4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of 61) or c2), the identity being the identity over the total length of amino acid sequence encoded by the nucleic acids of ε1) or ε2);

ε5) nucleic acids capable of hybridizing under stringent conditions with a complementary sequence of any of the nucleic acids according to ε1) or ε2); and ε6) nucleic acids encoding the same protein as any of the nucleic acids of ε1) or ε2), but differing from the nucleic acids of ε1) or ε2) above due to the degeneracy of the genetic code.

Nucleic acid having the nucleotide sequence of SEQ ID NO: 15 correspond to the pykA-gene of *Basfia succiniciproducens*-strain DD1.

In this context it is preferred that the modified microorganism according to the present invention comprises at least one of the following genetic modifications A) to E):

A) a deletion of the IdhA-gene or at least a part thereof, a deletion of a regulatory element of the IdhA-gene or at least a part thereof or an introduction of at least one mutation into the IdhA-gene;

B) a deletion of the pflD-gene or at least a part thereof, a deletion of a regulatory element of the pflD-gene or at least a part thereof or an introduction of at least one mutation into the pflD-gene;

or
a deletion of the pflA-gene or at least a part thereof, a deletion of a regulatory element of the pflA-gene or at least a part thereof or an introduction of at least one mutation into the pflA-gene;

C) a deletion of the wcaJ-gene or at least a part thereof, a deletion of a regulatory element of the wcaJ-gene or at least a part thereof or an introduction of at least one mutation into the wcaJ-gene;

D) a deletion of the pykA-gene or at least a part thereof, a deletion of a regulatory element of the pykA-gene or at least a part thereof or an introduction of at least one mutation into the pykA-gene that least to a reduction of the activity of the enzyme encodes by the pykA-gene;

E) a deletion of the ptsA-gene or at least a part thereof, a deletion of a regulatory element of the ptsA-gene or at least a part thereof or an introduction of at least one mutation into the ptsA-gene and/or
a deletion of the ptsH-gene or at least a part thereof, a deletion of a regulatory element of the ptsH-gene or at least a part thereof or an introduction of at least one mutation into the ptsH-gene.

In this context particularly preferred modified microorganism are those having the following properties or combination of properties: A), B), C), D), E), A)B), A)C), A)D) A)E), B)C), B)D), B)E), C)D), C)E), D)E), A)B)C), A)B)D), A)B)E), A)C)D), A)C)E), A)D)E), B)C)D), B)C)E), B)D) E)m C)D)E), A)B)C)D), A)B)C)E), A)B)D)E), A)C)D)E, B)C)D)E) and A)B)C)D)E), wherein a modified microorganism that is characterized by properties A), B), C), D) and E) is most preferred.

According to a first particularly preferred embodiment of the modified microorganism according to the present invention the microorganism comprises the following genetic modifications A) to E):
A) a deletion of the ldhA-gene or at least a part thereof;
B) a deletion of the pflA-gene or at least a part thereof or a deletion of the pflD-gene or at least a part thereof;
C) an introduction of at least one mutation into the wcaJ-gene that lead to the expression of a truncated enzyme encoded by the wcaJ-gene;
D) an introduction of at least one mutation into the pykA-gene that least to a reduction of the activity of the enzyme encodes by the pykA-gene; and
E) a deletion of the ptsA-gene or at least a part thereof.

According to a second particularly preferred embodiment of the modified microorganism according to the present invention the microorganism comprises the following genetic modifications A) to E):
A) a deletion of the ldhA-gene or at least a part thereof;
B) a deletion of the pflA-gene or at least a part thereof or a deletion of the pflD-gene or at least a part thereof;
C) an introduction of at least one mutation into the wcaJ-gene that lead to the expression of a truncated enzyme encoded by the wcaJ-gene;
D) an introduction of at least one mutation into the pykA-gene that least to a reduction of the activity of the enzyme encodes by the pykA-gene; and
E) a deletion of the ptsH-gene or at least a part thereof.

Particular preferred embodiments of the modified microorganisms according to the present invention are:
modified bacterial cells of the family Pasteurellaceae, in particular preferred of the genus *Basfia* and even more preferred of the species *Basfia succiniciproducens*,
in which the activity of the enzyme encoded by the ptsA-gene has been reduced, preferably by a deletion of the ptsA-gene, in particular by a modification of the ptsA-gene having the nucleic acid sequence according to SEQ ID NO: 3 and encoding for an enzyme having the amino acid sequence according to SEQ ID NO: 4;
in which the activity of the lactate dehydrogenase and the pyruvate formate lyase are reduced, preferably by a modification of the ldhA-gene and the pflA-gene, in particular by a modification of the ldhA-gene having the nucleic acid sequence according to SEQ ID NO: 7 and encoding for LdhA having the amino acid sequence according to SEQ ID NO: 8 and by a modification of the pflA-gene having the nucleic acid sequence according to SEQ ID NO: 9 and encoding for PflA having the amino acid sequence according to SEQ ID NO: 10, or a modification of the ldhA-gene and the pflD-gene, in particular by a modification of the ldhA-gene having the nucleic acid sequence according to SEQ ID NO: 7 and encoding for LdhA having the amino acid sequence according to SEQ ID NO: 8 and by a modification of the pflD-gene having the nucleic acid sequence according to SEQ ID NO: 11 and encoding for PflD having the amino acid sequence according to SEQ ID NO: 12;
in which the wcaJ-gene or at least a part thereof has been deleted or wherein at least one mutation has been introduced in the wcaJ-gene, in particular in the wcaJ-gene having the nucleic acid sequence according to SEQ ID NO: 13 and encoding for a protein having the amino acid sequence according to SEQ ID NO: 14, wherein the introduction of the at least one mutation preferably leads expression of an enzyme in which at least 100 amino acids, preferably at least 125 amino acids, more preferred at least 150 amino acids and most preferred at least 160 amino acids of the wildtype enzyme encoded by the wcaJ-gene are deleted from the C-terminal end;
and
in which at least one mutation has been introduced in the pykA-gene, in particular in the pykA-gene having the nucleic acid sequence according to SEQ ID NO: 15 and encoding for a protein having the amino acid sequence according to SEQ ID NO: 16, preferably at least one mutation the results in the substitution of at least one amino acid in the enzyme encoded by the pykA-gene, most preferred a mutation that results at least in a substitution of glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene.

modified bacterial cells of the family Pasteurellaceae, in particular preferred of the genus *Basfia* and even more preferred of the species *Basfia succiniciproducens*,
in which the activity of the enzyme encoded by the ptsH-gene has been reduced, preferably by a deletion of the ptsH-gene, in particular by a modification of the ptsH-gene having the nucleic acid sequence according to SEQ ID NO: 5 and encoding for an enzyme having the amino acid sequence according to SEQ ID NO: 6;

in which the activity of the lactate dehydrogenase and the pyruvate formate lyase are reduced, preferably by a modification of the IdhA-gene and the pflA-gene, in particular by a modification of the IdhA-gene having the nucleic acid sequence according to SEQ ID NO: 7 and encoding for LdhA having the amino acid sequence according to SEQ ID NO: 8 and by a modification of the pflA-gene having the nucleic acid sequence according to SEQ ID NO: 9 and encoding for PflA having the amino acid sequence according to SEQ ID NO: 10, or a modification of the IdhA-gene and the pflD-gene, in particular by a modification of the IdhA-gene having the nucleic acid sequence according to SEQ ID NO: 7 and encoding for LdhA having the amino acid sequence according to SEQ ID NO: 8 and by a modification of the pflD-gene having the nucleic acid sequence according to SEQ ID NO: 11 and encoding for PflD having the amino acid sequence according to SEQ ID NO: 12;

in which the wcaJ-gene or at least a part thereof has been deleted or wherein at least one mutation has been introduced in the wcaJ-gene, in particular in the wcaJ-gene having the nucleic acid sequence according to SEQ ID NO: 13 and encoding for a protein having the amino acid sequence according to SEQ ID NO: 14, wherein the introduction of the at least one mutation preferably leads expression of an enzyme in which at least 100 amino acids, preferably at least 125 amino acids, more preferred at least 150 amino acids and most preferred at least 160 amino acids of the wildtype enzyme encoded by the wcaJ-gene are deleted from the C-terminal end; and in which at least one mutation has been introduced in the pykA-gene, in particular in the pykA-gene having the nucleic acid sequence according to SEQ ID NO: 15 and encoding for a protein having the amino acid sequence according to SEQ ID NO: 16, preferably at least one mutation the results in the substitution of at least one amino acid in the enzyme encoded by the pykA-gene, most preferred a mutation that results at least in a substitution of glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene.

A contribution to solving the problems mentioned at the outset is furthermore provided by a method of producing an organic compound comprising:

I) cultivating the modified microorganism according to the present invention in a culture medium comprising at least one assimilable carbon source to allow the modified microorganism to produce the organic compound, thereby obtaining a fermentation broth comprising the organic compound;

II) recovering the organic compound from the fermentation broth obtained in process step I).

In process step I) the modified microorganism according to the present invention is cultured in a culture medium comprising at least one assimilable carbon source to allow the modified microorganism to produce the organic compound, thereby obtaining a fermentation broth comprising the organic compound. Preferred organic compounds that can be produced by the process according to the present invention comprise carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof, tricarboxylic acids such as citric acid or salts thereof, alcohols such as methanol or ethanol, amino acids such as L-asparagine, L-aspartic acid, L-arginine, L-isoleucine, L-glycine, L-glutamine, L-glutamic acid, L-cysteine, L-serine, L-tyrosine, L-tryptophan, L-threonine, L-valine, L-histidine, L-proline, L-methionine, L-lysine, L-leucine, etc.

According to a preferred embodiment of the process according to the present invention the organic compound is succinic acid. The term "succinic acid", as used in the context of the present invention, has to be understood in its broadest sense and also encompasses salts thereof (i.e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The modified microorganism according to the present invention is, preferably, incubated in the culture medium at a temperature in the range of about 10 to 60° C. or 20 to 50° C. or 30 to 45° C. at a pH of 5.0 to 9.0 or 5.5 to 8.0 or 6.0 to 7.0.

Preferably, the organic compound, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably selected from sucrose, maltose, maltotriose, maltotetraose, maltopentaose, maltohexaose, maltoheptaose, D-fructose, D-glucose, D-xylose, L-arabinose, D-galactose, D-mannose, glycerol and mixtures thereof or compositions containing at least one of said compounds, or is selected from decomposition products of starch, cellulose, hemicellulose and/or lignocellulose. A preferred assimilable carbon source is sucrose. Further preferred mixtures are a mixture of sucrose and at least one further assimilable carbon source, such as a mixture of sucrose and maltose, sucrose and D-fructose, sucrose and D-glucose, sucrose and D-xylose, sucrose and L-arabinose, sucrose and D-galactose, sucrose and D-mannose.

According to a preferred embodiment of the process according to the present invention at least 50 wt.-%, preferably at least 75 wt.-%, more preferably at least 90 wt.-%, even more preferably at least 95 wt.-% and most preferably at least 99 wt.-% of the assimilable carbon source, based on the total weight of the assimilable carbon source with the exception of carbon dioxide, is sucrose.

The initial concentration of the assimilable carbon source, preferably the initial concentration of sucrose, is preferably adjusted to a value in a range of 5 to 100 g/l, preferably 5 to 75 g/l and more preferably 5 to 50 g/l and may be maintained in said range during cultivation. The pH of the reaction medium may be controlled by addition of suitable bases as for example, gaseous ammonia, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$ and/or mixtures thereof. These alkaline neutralization agents are especially required if the organic compounds that are formed in the course of the fermentation process are carboxylic acids or dicarboxylic acids. In the case of succinic acid as the organic compound, $Mg(OH)_2$ is a particular preferred base.

The fermentation step I) according to the present invention can, for example, be performed in stirred fermenters, bubble columns and loop reactors. A comprehensive overview of the possible method types including stirrer types and geometric designs can be found in Chmiel: "*Bioprozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic acid, especially succinic acid, in process step I) are:

| | |
|---|---|
| Assimilable carbon source: | sucrose |
| Temperature: | 30 to 45° C. |
| pH: | 5.5 to 7.0 |
| Supplied gas: | $CO_2$ |

It is furthermore preferred in process step I) that the assimilable carbon source, preferably sucrose, is converted to the organic compound, preferably to succinic acid, with a carbon yield YP/S of at least 0.5 g/g up to about 1.18 g/g; as for example a carbon yield YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g or of at least 1.1 g/g (organic compound/carbon, preferably succinic acid/carbon).

It is furthermore preferred in process step I) that the assimilable carbon source, preferably sucrose, is converted to the organic compound, preferably to succinic acid, with a specific productivity yield of at least 0.6 g g $DCW^{-1}h^{-1}$ organic compound, preferably succinic acid, or of at least of at least 0.65 g g $DCW^{-1}h^{-1}$, of at least 0.7 g g $DCW^{-1}h^{-1}$, of at least 0.75 g g $DCW^{-1}h^{-1}$ or of at least 0.77 g g $DCW^{-1}h^{-1}$ organic compound, preferably succinic acid.

It is furthermore preferred in process step I) that the assimilable carbon source, preferably sucrose, is converted to the organic compound, preferably to succinic acid, with a space time yield for the organic compound, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic compound, preferably succinic acid. According to another preferred embodiment of the process according to the present invention in process step I) the modified microorganism is converting at least 20 g/L, more preferably at least 25 g/l and even more preferably at least 30 g/l of the assimilable carbon source, preferably sucrose, to at least 20 g/l, more preferably to at least 25 g/l and even more preferably at least 30 g/l of the organic compound, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic compound produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g $DCW^{-1}$ $h^{-1}$). The space-time-yield (STY) is defined as the ratio of the total amount of organic compound formed in the fermentation process to the volume of the culture, regarded over the entire time of cultivation. The space-time yield is also known as the "volumetric productivity".

In process step II) the organic compound is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic compound, preferably succinic acid, is further purified. If, however, the organic compound is converted into a secondary organic product by chemical reactions as described below, a further purification of the organic compound is, depending on the kind of reaction and the reaction conditions, not necessarily required. For the purification of the organic compound obtained in process step II), preferably for the purification of succinic acid, methods known to the person skilled in the art can be used, as for example crystallization, filtration, electrodialysis and chromatography. In the case of succinic acid as the organic compound, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove undesired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i.e. succinic acid), which subsequently can be crystallized by cooling down the acidified medium. Examples of further suitable purification processes are disclosed in EP-A-1 005 562, WO-A-2008/010373, WO-A-2011/082378, WO-A-2011/043443, WO-A-2005/030973, WO-A-2011/123268 and WO-A-2011/064151 and EP-A-2 360 137.

According to a preferred embodiment of the process according to the present invention the process further comprises the process step:

III) conversion of the organic compound contained in the fermentation broth obtained in process step I) or conversion of the recovered organic compound obtained in process step II) into a secondary organic product being different from the organic compound by at least one chemical reaction.

In case of succinic acid as the organic compound preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:
 b1) either the direct catalytic hydrogenation of the succinic acid obtained in process steps I) or II) to THF and/or BDO and/or GBL or
 b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:
 b) the chemical conversion of succinic acid ammonium salts obtained in process steps I) or II) to pyrrolidones in a manner known per se.

For details of preparing these compounds reference is made to US-A-2010/0159543 and WO-A-2010/092155.

A contribution to solving the problems mentioned at the outset is furthermore provided by the use of the modified microorganism according to the present invention for the fermentative production of organic compounds. Preferred organic compounds are those compounds that have already been mentioned in connection with the process according to the present invention, succinic acid being the most preferred organic compound. Furthermore, preferred conditions for the fermentative production of organic compounds, preferably of succinic acid, are those conditions that have already been described in connection with process step I) of the process according to the present invention. The preferred assimilable carbon source that is used for the fermentative production of the organic compound, in particular for the fermentative production of succinic acid, is sucrose.

The invention is now explained in more detail with the aid of figures and non-limiting examples.

EXAMPLES

Example 1: General Method for the Transformation of *Basfia succiniciproducens*

TABLE 1

Nomenclature of the DD1-wildtype and mutants referred to in the examples
Strain

| Wildtype DD1 (deposit DSM18541) |
| DD1 ΔldhA |
| DD1 ΔldhA ΔpflA |
| DD1 ΔldhA ΔpflA pykA1 |
| DD1 ΔldhA ΔpflA pykA1 wcaJ* |
| DD1 ΔldhA ΔpflA pykA1 wcaJ* ΔptsA |
| DD1 ΔldhA ΔpflA pykA1 wcaJ* ΔptsH |

*Basfia succiniciproducens* DD1 (wildtype) was transformed with DNA by electroporation using the following protocol:

For preparing a pre-culture DD1 was inoculated from frozen stock into 40 ml BHI (brain heart infusion; Becton, Dickinson and Company) in 100 ml shake flask. Incubation was performed over night at 37° C.; 200 rpm. For preparing the main-culture 100 ml BHI were placed in a 250 ml shake flask and inoculated to a final OD (600 nm) of 0.2 with the pre-culture. Incubation was performed at 37° C., 200 rpm. The cells were harvested at an OD of approximately 0.5, 0.6 and 0.7, pellet was washed once with 10% cold glycerol at 4° C. and re-suspended in 2 ml 10% glycerol (4° C.).

100 μl of competent cells were the mixed with 2-8 μg Plasmid-DNA and kept on ice for 2 min in an electroporation cuvette with a width of 0.2 cm. Electroporation under the following conditions:

400 Ω; 25 μF; 2.5 kV (Gene Pulser, Bio-Rad). 1 ml of chilled BHI was added immediately after electroporation and incubation was performed for approximately 2 h at 37° C.

Cells were plated on BHI with 5 mg/L chloramphenicol and incubated for 2-5 d at 37° C. until the colonies of the transformants were visible. Clones were isolated and restreaked onto BHI with 5 mg/l chloramphenicol until purity of clones was obtained.

Example 2 a) Generation of Deletion Constructs

Figure 1:
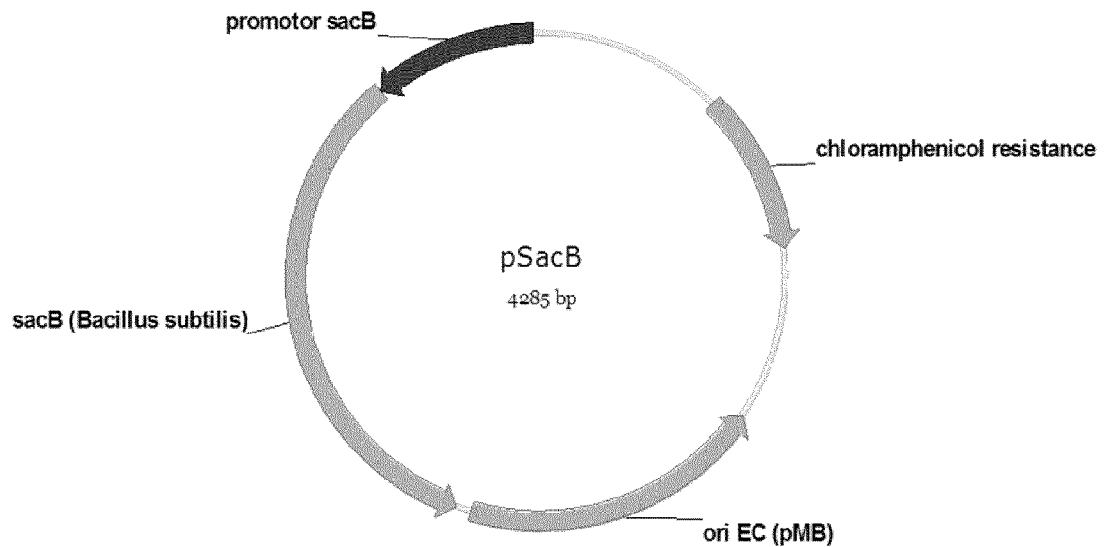
FIG. 1 shows a schematic map of plasmid pSacB (SEQ ID NO: 17).
Figure 2:
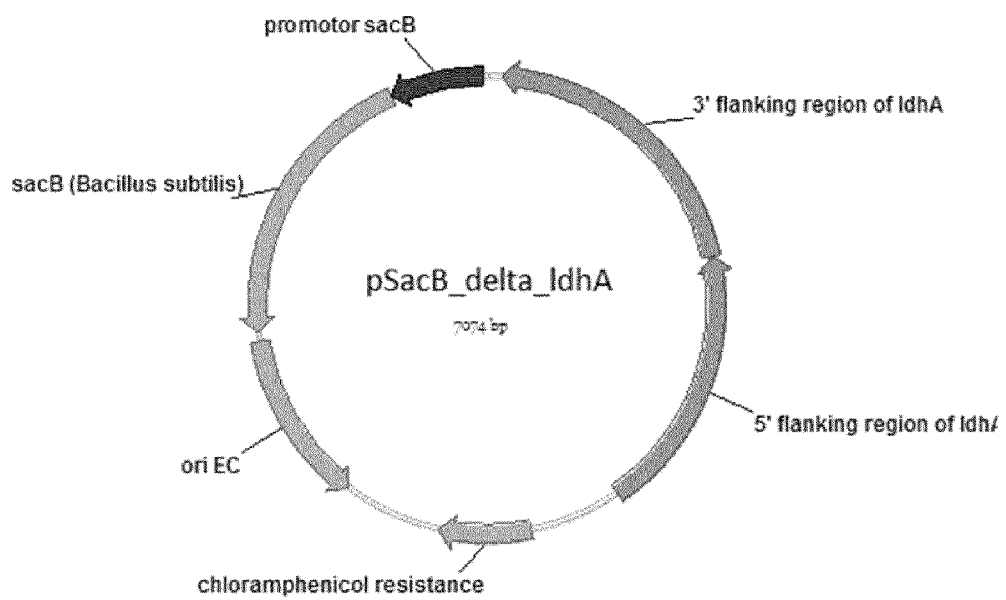
FIG. 2 shows a schematic map of plasmid pSacB ΔIdhA (SEQ ID NO: 18).
Figure 3:
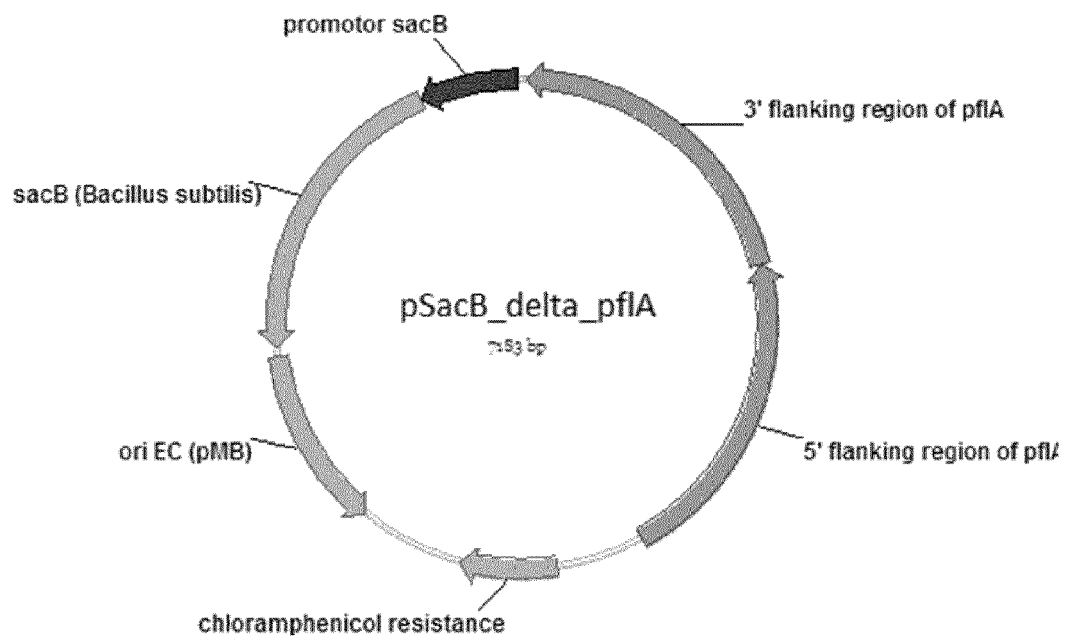
FIG. 3 shows a schematic map of plasmid pSacB ΔpflA (SEQ ID NO: 19).

Deletion plasmids were constructed based on the vector pSacB (SEQ ID NO: 17). FIG. 1 shows a schematic map of plasmid pSacB. 5'- and 3'-flanking regions (approx. 1500 bp each) of the chromosomal fragment, which should be deleted were amplified by PCR from chromosomal DNA of *Basfia succiniciproducens* and introduced into said vector using standard techniques.

Normally, at least 80% of the ORF were targeted for a deletion. In such a way, the deletion plasmids for the lactate dehydrogenase ldhA, pSacB_delta_IdhA (SEQ ID NO: 18), the pyruvate formate lyase activating enzyme pflA, pSacB_delta_ pflA (SEQ ID NO: 19), the ptsA-gene, pSacB_delta_ptsA (SEQ ID NO: 22), and the ptsH-gene, pSacB_delta_ptsH (SEQ ID NO: 23). FIGS. 2, 3, 6 and 7 show schematic maps of plasmid pSacB_delta_IdhA, pSacB_delta_pflA, pSacB_delta_ptsA and pSacB_delta_ptsH, respectively.

In the plasmid sequence of pSacB (SEQ ID NO: 17) the sacB-gene is contained from bases 2380-3801. The sacB-promotor is contained from bases 3802-4264. The chloramphenicol gene is contained from base 526-984. The origin of replication for *E. coli* (ori EC) is contained from base 1477-2337 (see FIG. 1).

In the plasmid sequence of pSacB_delta_IdhA (SEQ ID NO: 18) the 5' flanking region of the IdhA gene, which is homologous to the genome of *Basfia succiniciproducens*, is contained from bases 1519-2850, while the 3' flanking region of the IdhA-gene, which is homologous to the genome of *Basfia succiniciproducens*, is contained from bases 62-151. The sacB-gene is contained from bases 5169-6590. The sacB-promoter is contained from bases 6591-7053. The chloramphenicol gene is contained from base 3315-3773. The origin of replication for *E. coli* (ori EC) is contained from base 4266-5126 (see FIG. 2).

In the plasmid sequence of pSacB_delta_pflA (SEQ ID NO: 19) the 5' flanking region of the pflA-gene, which is homologous to the genome of *Basfia succiniciproducens*, is contained from bases 1506-3005, while the 3' flanking region of the pflA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 3).

In the plasmid sequence of pSacB_delta_ptsA (SEQ ID NO: 22) the 5' flanking region of the ptsA-gene, which is homologous to the genome of *Basfia succiniciproducens*, is contained from bases 1506-3005, while the 3' flanking region of the ptsA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 6).

Figure 4:
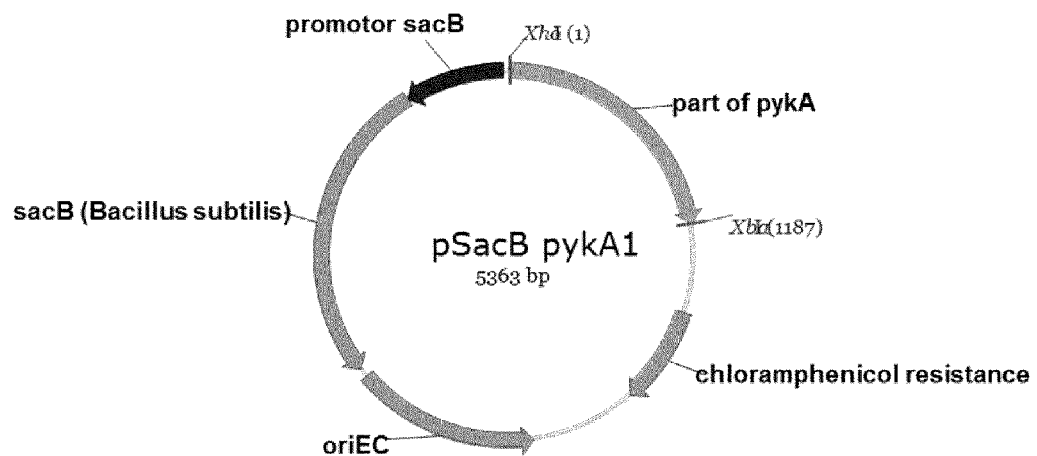
FIG. 4 shows a schematic map of plasmid pSacB pykA1 (SEQ ID NO: 20).

In the plasmid sequence of pSacB_delta_ptsH (SEQ ID NO: 23) the 5' flanking region of the ptsH-gene, which is homologous to the genome of *Basfia succiniciproducens*, is contained from bases 1541-3055, while the 3' flanking region of the ptsH-gene, which is homologous to the genome of *Basfia succiniciproducens*, is contained from bases 6-1540. The sacB-gene is contained from bases 5328-6749. The sacB-promoter is contained from bases 6750-7212. The chloramphenicol gene is contained from base 3474-3932. The origin of replication for *E. coli* (ori EC) is contained from base 4425-5285 (see FIG. 7).

b) Generation of constructs used for introduction of point mutations into the pykA-gene, and into the wcaJ-gene In the plasmid sequence of pSacB_pykA1 (SEQ ID NO: 20) the part of the pykA-gene, which is homologous to the genome of *Basfia succiniciproducens*, is contained from bases 6-1185. The sacB-gene is contained from bases 3458-4879. The sacB-promoter is contained from bases 4880-5342. The chloramphenicol gene is contained from bases 1604-2062. The origin of replication for *E. coli* (ori EC) is contained from bases 2555-3415 (see FIG. 4). The plasmid pSacB_pykA1 introduces G to T mutation in the pykA-gene which finally result in exchange of G (glycine) to C (cysteine) at position 167 in the PykA-protein (SEQ ID NO: 16).

Figure 5:
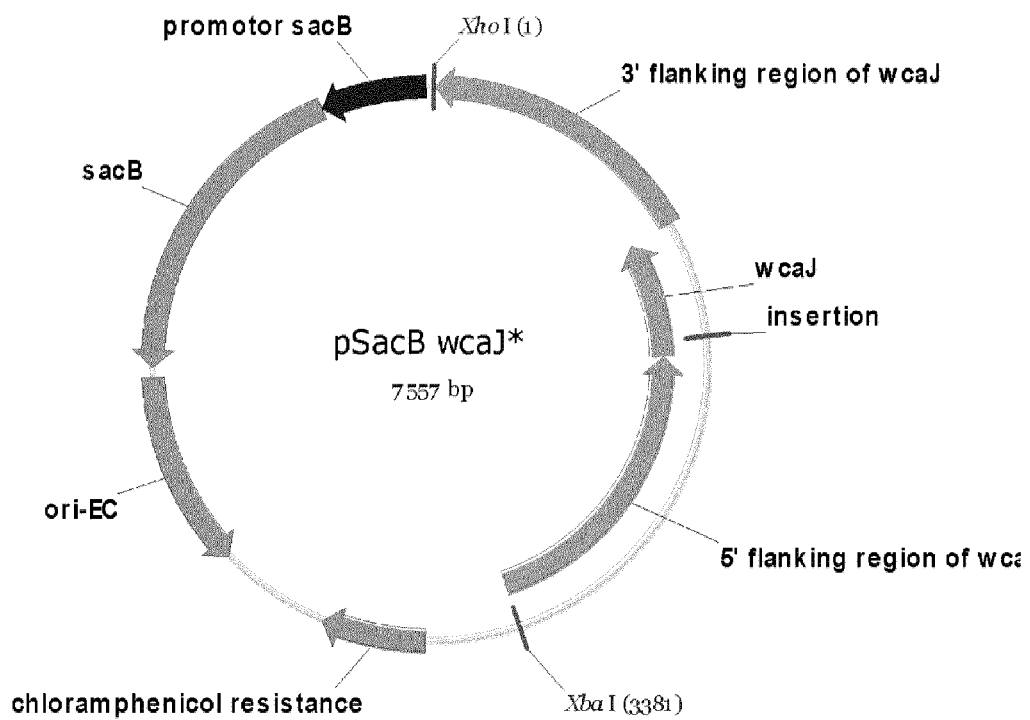
FIG. 5 shows a schematic map of plasmid pSacB wcaJ* (SEQ ID NO: 21).
Figure 6:
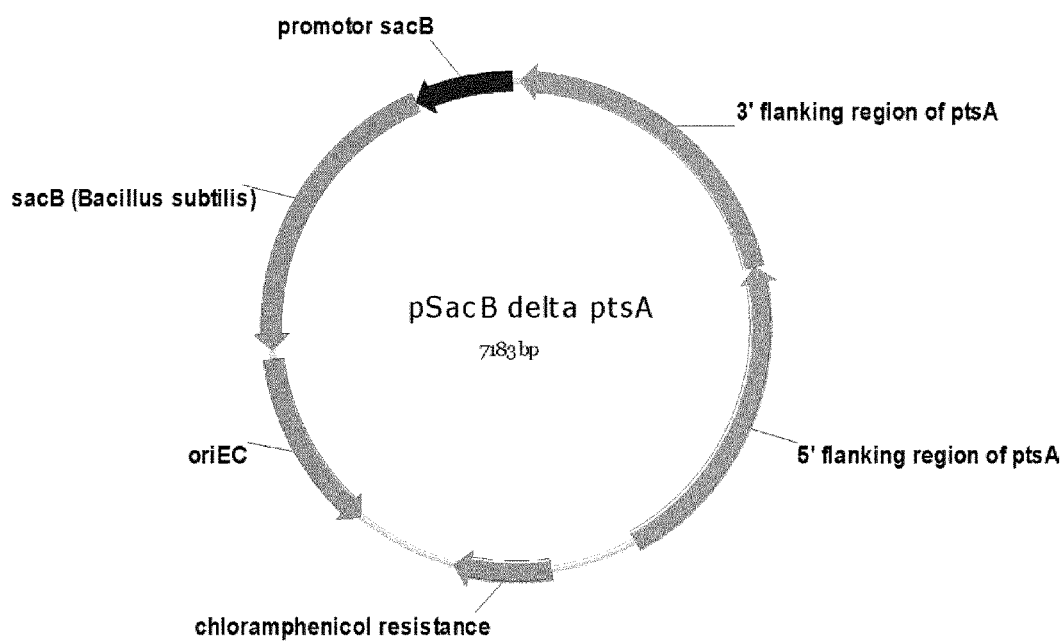
FIG. 6 shows a schematic map of plasmid pSacB ΔptsA (SEQ ID NO: 22).
Figure 7:
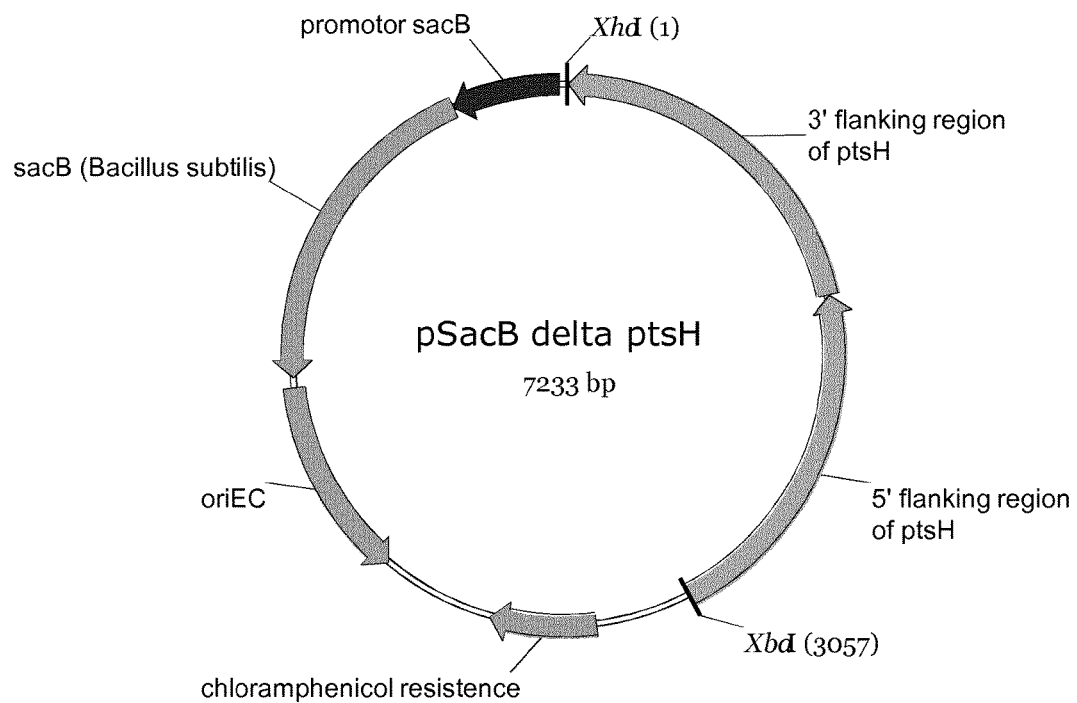
FIG. 7 shows a schematic map of plasmid pSacB ΔptsH (SEQ ID NO: 23).

In the plasmid sequence of pSacB_wcaJ* (SEQ ID NO: 21) the 5' flanking region of the wcaJ-gene, which is homologous to the genome of *Basfia succiniciproducens*, is contained from bases 1838-3379, while the 3' flanking region of the wcaJ-gene, which is homologous to the genome of *Basfia succiniciproducens*, is contained from bases 6-1236. The sacB-gene is contained from bases 5652-7073. The sacB-promoter is contained from bases 7074-7536. The chloramphenicol gene is contained from bases 3798-4256. The origin of replication for *E. coli* (ori EC) is contained from bases 4749-5609. The wcaJ-gene is contained from bases 1237-1837 with an insertion of a nucleotide in the codon that encodes of lysine between thymine at position 81 and adenine at position 82 (which corresponds to position 1756 of plasmid pSacB_wcaJ*, see FIG. 5). This insertion leads to a frame shift mutation, wherein by means of this frame shift mutation a stop codon is introduced, leading to the expression of a truncated enzyme.

Example 3: Generation of Improved Succinate Producing Strains a) *Basfia succiniciproducens* DD1 was transformed as described above with the pSacB_delta_IdhA and "Campbelled in" to yield a "Campbell in" strain. Transformation and integration into the genome of *Basfia succiniciproducens* was confirmed by PCR yielding bands for the integrational event of the plasmid into the genome of *Basfia succiniciproducens*.

The "Campbell in" strain was then "Campbelled out" using agar plates containing sucrose as a counter selection medium, selecting for the loss (of function) of the sacB gene.

Therefore, the "Campbell in" strains were incubated in 25-35 ml of non-selective medium (BHI containing no antibiotic) at 37° C., 220 rpm overnight. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB levan-sucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.

The "Campbelled out" strains containing the mutation/deletion of the IdhA-gene were confirmed by chloramphenicol sensitivity. The mutation/deletion mutants among these strains were identified and confirmed by PCR analysis. This led to the IdhA-deletion mutant *Basfia succiniciproducens* DD1 ΔldhA.

b) *Basfia succiniciproducens* ΔldhA was transformed with pSacB_delta_pflA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the IdhA pflA double deletion mutant *Basfia succiniciproducens* DD1 ΔldhA ΔpflA.

c) *Basfia succiniciproducens* ΔldhA ΔpflA was transformed with pSacB_pykA1 as described above and "Campbelled in" to yield a "Campbell in" strain. The "Campbell in" strain was then "Campbelled out" as described previously. The mutants among these strains were identified and confirmed by PCR analysis. This led to the mutant *Basfia succiniciproducens* DD1 ΔldhA ΔpflA pykA1 in which ldhA and pflA are deleted, and which expresses a pyruvate kinase in which at amino acid at position 167 glycine is substituted by cysteine.

d) *Basfia succiniciproducens* ΔldhA ΔpflA pykA1 was transformed with pSacB_wcaJ* as described above and "Campbelled in" to yield a "Campbell in" strain. The "Campbell in" strain was then "Campbelled out" as described previously. The mutants among these strains were identified and confirmed by PCR analysis. This led to the mutant *Basfia succiniciproducens* DD1 ΔldhA ΔpflA pykA1 wcaJ* in which ldhA and pflA are deleted, which expresses a pyruvate kinase in which at amino acid at position 167 glycine is substituted by cysteine, and which expresses a truncated enzyme encoded by the wcaJ-gene.

e) *Basfia succiniciproducens* ΔldhA ΔpflA pykA1 wcaJ* was transformed with pSacB_delta_ptsA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the mutant *Basfia succiniciproducens* DD1 ΔldhA ΔpflA pykA1 wcaJ* ΔptsA.

f) *Basfia succiniciproducens* ΔldhA ΔpflA pykA1 wcaJ* was transformed with pSacB_delta_hPr as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the mutant *Basfia succiniciproducens* DD1 ΔldhA ΔpflA pykA1 wcaJ* ΔptsH.

Example 4: Cultivation of Various DD1-Strains on Glucose and Sucrose

Productivity was analyzed utilizing media and incubation conditions described below.
1. Medium Preparation
The composition and preparation of the cultivation medium CGM is as described in the following table 2.

TABLE 2

Medium composition for cultivation on glucose (medium CGM)

| Compound | Concentration [g/L] |
| --- | --- |
| Yeast extract (Bio Springer) | 12.5 |
| Succinic acid | 2.5 |

TABLE 2-continued

Medium composition for cultivation on glucose (medium CGM)

| Compound | Concentration [g/L] |
| --- | --- |
| $(NH_4)_2SO_4$ | 0.5 |
| $KH_2PO_4$ | 1.0 |
| $MgCO_3$ | 50.0 |
| $Na_2CO_3$ | 2.0 |
| glucose | 50 |

The composition and preparation of the cultivation medium LSM_3 is as described in the following tables 3, 4, and 5.

TABLE 3

Composition of trace element solution
Trace element solution

| Compound | Final concentration |
| --- | --- |
| citric acid | 10 g/L |
| $ZnSO_4 \times 7\ H_2O$ | 1851 mg/L |
| $CaSO_4 \times 2\ H_2O$ | 10 mg/L |
| $FeSO_4 \times 7\ H_2O$ | 2040 mg/L |
| $CaCl_2 \times 2\ H_2O$ | 12460 mg/L |
| $MnCl_2 \times 4\ H_2O$ | 1200 mg/L |
| $Na_2MoO_4 \times 2\ H_2O$ | 38 mg/L |
| $CuCl_2 \times 2\ H_2O$ | 188 mg/L |
| $NiCl_2 \times 6\ H_2O$ | 32 mg/L |
| $CoCl_2 \times 6\ H_2O$ | 101 mg/L |

TABLE 4

Composition of vitamin solution
Vitamin solution

| Compound | Final concentration |
| --- | --- |
| Thiamin HCl (B1) | 1.0 g/L |
| Nicotinic acid (B3) | 1.0 g/L |
| Riboflavin (B2) | 20 mg/L |
| Biotin (B7) | 50 mg/L |
| Pantothenic acid (B5) | 1.0 g/L |
| Pyridoxine (B6) | 1.0 g/L |
| Cyanocobalamin (B12) | 50 mg/L |
| Lipoic acid | 5 mg/L |

TABLE 5

Composition of LSM_3 medium for cultivation on sucrose

| Compound | Volume/Mass | Stock concentration | Final concentration |
| --- | --- | --- | --- |
| Medium 1 | | | |
| $MgCO_3$ | 2.5 g | 100% | 50.00 g/L |
| Water | 38.6 mL | — | — |
| Medium 2 | | | |
| Succinic acid | 2.5 mL | 50 g/L | 2.50 g/L |
| Sucrose | 3.85 mL | 650 g/L | 50.00 g/L |
| $(NH_4)_2SO_4$ | 0.50 mL | 500 g/L | 5.00 g/L |
| Betain | 0.50 mL | 23 g/L | 0.23 g/L |
| $KH_2PO_4$ | 0.50 mL | 100 g/L | 1.00 g/L |
| $Na_2CO_3$ | 0.50 mL | 200 g/L | 2.00 g/L |
| vitamin solution | 0.50 mL | 4 g/L | 0.04 g/L |
| trace element solution | 0.05 mL | 21 g/L | 0.02 g/L |

2. Cultivations and Analytics

For growing the pre-culture bacteria from a freshly grown BHI-agar plate (incubated overnight at 37° C. under anaerobic conditions) was used to inoculate to OD600=0.75 a 100 ml-serum bottle with gas tight butyl rubber stopper containing 50 ml of the CGM liquid medium described in table 2 with a $CO_2$-atmosphere. The bottles were incubated at 37° C. and 170 rpm (shaking diameter: 2.5 cm). For growing the main culture 2.5 ml of the bacterial culture in the CGM medium (after 10 hours of incubation) was used to inoculate a 100 ml-serum bottle with gas tight butyl rubber stopper containing 50 ml of the LSM_3 liquid medium described in table 5 with a $CO_2$-atmosphere. Production of succinic acid was quantified via HPLC (HPLC methods are described in tables 7 and 8). Cell growth was measured by measuring the absorbance at 600 nm (OD600) using a spectrophotometer (Ultrospec3000, Amersham Biosciences, Uppsala Sweden).

3. Results

The results of the cultivation experiments with different DD1-strains are shown in table 6.

TABLE 6

Cultivation of the DD1ΔldhAΔpflApykA1wcaJ*-strain, the DD1ΔldhAΔpflApykA1wcaJ*ΔptsA-strain and the DD1ΔldhAΔpflApykA1wcaJ*ΔptsH-strain on sucrose (medium LSM_3).

| | DD1ΔldhAΔpflA pykA1wcaJ* | DD1ΔldhAΔpflA pykA1wcaJ*ΔptsA | DD1ΔldhAΔpflA pykA1wcaJ*ΔptsH |
|---|---|---|---|
| SA Yield (SS/S) [g/g][a] | 0.75 | 0.78 | 0.85 |

[a]SA yield (ration of succinic acid per consumed substrate)

TABLE 7

HPLC method (ZX-THF50) for analysis of succinic acid

| | |
|---|---|
| HPLC column | Aminex HPX-87 H, 300 × 7.8 mm (BioRad) |
| Precolumn | Cation H |
| Temperature | 50° C. |
| Eluent flow rate | 0.50 ml/min |
| Injection volume | 5.0 μl |
| Diode array detector | RI-Detector |
| Runtime | 28 min |
| max. pressure | 140 bar |
| Eluent A | 5 mM $H_2SO_4$ |
| Eluent B | 5 mM $H_2SO_4$ |

| Gradient | Time [min] | A[%] | B[%] | Flow [ml/min] |
|---|---|---|---|---|
| | 0.0 | 50 | 50 | 0.50 |
| | 28.0 | 50 | 50 | 0.50 |

TABLE 8

HPLC method (Fast-CH) for analysis of sucrose

| | |
|---|---|
| HPLC column | Fast Carbohydrate, 100 × 7.8 mm (Biorad) |
| Precolumn | Deashing Refill Cartridges (30° C.) |
| Temperature | 75° C. |
| Eluent flow rate | 1.00 ml/min |
| Injection volume | 1.0 μl |
| Diode array detector | RI-Detector |
| Runtime | 8 min |
| max. pressure | 150 bar |
| Eluent A | water |
| Eluent B | water |

| Gradient | Time [min] | A[%] | B[%] | Flow [ml/min] |
|---|---|---|---|---|
| | 0.0 | 50 | 50 | 1.00 |
| | 8.0 | 50 | 50 | 1.00 |

```
SEQUENCES
SEQ ID NO: 1 (nucleotide sequence of 16 S rDNA of strain DD1)
tttgatcctggctcagattgaacgctggcggcaggcttaacacatgcaagtcgaacggtagcgggaggaaagcttgctttctttgccga cgagtggcggacgggtgagtaatgcttggggatctggcttatggaggggggataacgacgggaaactgtcgctaataccgcgtaatat cttcggattaaagggtgggactttcgggccacccgccataagatgagcccaagtgggattaggtagttggtggggtaaaggcctacc aagccgacgatctctagctggtctgagaggatgaccagccacactggaactgagacacggtccagactcctacgggaggcagca gtggggaatattgcacaatgggggaaccctgatgcagccatgccgcgtgaatgaagaaggccttcgggttgtaaagttctttcggtg acgaggaaggtgtttgttttaataggacaagcaattgacgttaatcacagaagaagcaccggctaactccgtgccagcagccgcggt aatacggagggtgcgagcgttaatcggaataactgggcgtaaagggcatgcaggcggacttttaagtgagatgtgaaagcccgg gcttaacctgggaattgcatttcagactgggagtctagagtactttagggaggggtagaattccacgtgtagcggtgaaatgcgtagag atgtggaggaataccgaaggcgaaggcagccccttgggaagatactgacgctcatatgcgaaagcgtggggagcaaacaggatt agataccctggtagtccacgcggtaaacgctgtcgatttggggattgggcttaggcctggtgctcgtagctaacgtgataaatcgacc gcctggggagtacggccgcaaggttaaaactcaaatgaattgacggggcccgcacaagcggtggagcatgtggtttaattcgatg caacgcgaagaaccttacctactcttgacatccagagaatcctgtagagatacgggagtgccttcgggagctctgagacaggtgctg catggctgtcgtcagctcgtgttgtgaaatgttgggttaagtcccgcaacgagcgcaacccttatcctttgttgccagcatgtaaagatgg gaactcaaaggagactgccggtgacaaaccggaggaaggtggggatgacgtcaagtcatcatggcccttacgagtagggctaca cacgtgctacaatggtgcatacagagggcggcgataccgcgaggtagagcgaatctcagaaagtgcatcgtagtccggattggagt ctgcaactcgactccatgaagtcggaatcgctagtaatcgcaaatcagaatgttgcggtgaatacgttcccgggccttgtacacaccg
```

-continued cccgtcacaccatgggagtgggttgtaccagaagtagatagcttaaccttcggggggggcgtttaccacggtatgattcatgactggg gtgaagtcgtaacaaggtaaccgtaggggaacctgcgg SEQ ID NO: 2 (nucleotide sequence of 23 S rDNA of strain DD1)
agtaataacgaacgacacaggtataagaatacttgaggttgtatggttaagtgactaagcgtacaaggtggatgccttggcaatcaga ggcgaagaaggacgtgctaatctgcgaaaagcttgggtgagttgataagaagcgtctaacccaagatatccgaatggggcaaccc agtagatgaagaatctactatcaataaccgaatccataggttattgaggcaaaccgggagaactgaaacatctaagtaccccgagg aaagaaatcaaccgagattacgtcagtagcggcgagcgaaagcgtaagagccggcaagtgatagcatgaggattagaggaat cggctgggaagccgggcggcacagggtgatagccccgtacttgaaaatcattgtgtggtactgagcttgcgagaagtagggcggga cacgagaaatcctgtttgaagaaggggggaccatcctccaaggctaaatactcctgattgaccgatagtgaaccagtactgtgaagg aaaggcgaaaagaaccccggtgaggggagtgaaatagaacctgaaaccttgtacgtacaagcagtgggagcccgcgagggtga ctgcgtaccttttgtataatgggtcagcgacttatattatgtagcgaggttaaccgaataggggagccgaagggaaaccgagtcttaact gggcgtcgagttgcatgatatagacccgaaacccggtgatctagccatgggcaggttgaaggttgggtaacactaactggaggacc gaaccgactaatgttgaaaaattagcggatgacctgtggctgggggtgaaaggccaatcaaaccgggagatagctggttctccccg aaatctatttaggtagagccttatgtgaataccttcggggtagagcactgtttcggctaggggccatcccggcttaccaacccgatgc aaactgcgaataccgaagagtaatgcataggagacacacggcgggtgctaacgttcgtcgtggagagggaaacaacccagacc gccagctaaggtcccaaagtttatattaagtgggaaacgaagtgggaaggcttagacagctaggatgttggcttagaagcagccatc atttaaagaaagcgtaatagctcactagtcgagtcggcctgcgcggaagatgtaacggggctcaaatatagcaccgaagctgcggc atcaggcgtaagcctgttgggtaggggagcgtcgtgtaagcggaagaaggtggttcgagagggctgctggacgtatcacgagtgcg aatgctgacataagtaacgataaaacgggtgaaaaacccgttcgccggaagaccaagggttcctgtccaacgttaatcggggcag ggtgagtcggcccctaaggcgaggctgaagagcgtagtcgatgggaaacgggttaatattcccgtacttgttataattgcgatgtggg gacggagtaggttaggttatcgacctgttggaaaaggtcgtttaagttggtaggtggagcgtttaggcaaatccggacgcttatcaaca ccgagagatgatgacgaggcgctaaggtgccgaagtaaccgataccacacttccaggaaaagccactaagcgtcagattataata aaccgtactataaaccgacacaggtggtcaggtagagaatactcaggcgcttgagagaactcgggtgaaggaactaggcaaaata gcaccgtaacttcgggagaaggtgcgccggcgtagattgtagaggtataccttgaaggttgaaccggtcgaagtgacccgctggct gcaactgttttattaaaaacacagcactctgcaaacacgaaagtggacgtataggtgtgatgcctgcccggtgctggaaggttaattg atggcgttatcgcaagagaagcgcctgatcgaagccccagtaaacggcggccgtaactataacggtcctaaggtagcgaaattcctt gtcgggtaagttccgacctgcacgaatggcataatgatggccaggctgtctccacccgagactcagtgaaattgaaatcgccgtgaa gatgcggtgtacccgcggctagacggaaagacccgtgaacctttactatagcttgacactgaaccttgaattttgatgtgtaggatag gtgggaggctttgaagcggtaacgccagttatcgtggagccatccttgaaataccaccctttaacgtttgatgttctaacgaagtgcccg gaacgggtactcggacagtgtctggtgggtagtttgactggggcggtctcctcccaaagagtaacgaggagcacgaaggtttgcta atgacggtcggacatcgtcaggttagtgcaatggtataagcaagcttaactgcgagacggacaagtcgagcaggtgcgaaagcag gtcatagtgatccggtggttctgaatggaagggccatcgctcaacggataaaaggtactccggggataacaggctgataccgccca agagttcatatcgacggcggtgtttggcacctcgatgtcggctcatcacatcctggggctgaagtaggtcccaagggtatggctgttcgc catttaaagtggtacgcgagctgggtttaaaacgtcgtgagacagtttggtccctatctgccgtgggcgttggagaattgagagggggct gctcctagtacgagaggaccggagtggacgcatcactggtgttccggttgtgtcgccagacgcattgccgggtagctacatgcgaa gagataagtgctgaaagcatctaagcacgaaacttgcctcgagatgagttctcccagtatttaatactgtaagggttgttggagacgac gacgtagataggccgggtgtgtaagcgttgcgagacgttgagctaaccggtactaattgcccgagaggcttagccatacaacgctca agtgtttttggtagtgaaagttattacggaataagtaagtagtcagggaatcggct SEQ ID NO: 3 (nucleotide sequence of ptsA-gene from strain DD1)
atgatttcaggaatcccggcctcaccaggtatcgttttggtaaagcgttagttctgaaagaggaaaaaattgtacttgatatgcaaaaa attgctgaagatcaagttgaaactgaagtagctcgttttttatgaaggccgtacggcggcagtggaacaattaagcgccattagagatc gtgcagagaaaactctcggtgaagaaaaagcggctatcttcgaaggtcatttaatgattcttgaagatgaagagttggaagaagaaa -continued

```
tcattgattatttgcgttcaaacaaagtaaatgcgggcgttgcggcaagtaaaatcattgatcaacaagttgctatgcttgcggatattgat gatgagtacttaaaagaacgtgccggcgatattcgcgatatcggtaaccgtttaattaaaaatatcttaggcatgaaaattgtggatttgg gcgaaatcaatgaagagtcaatcttggttgcttatgacttaacgccatcagaaaccgcacaattgaatttagacaaagtattaggttttat tactgatatcggtggtcgtacttcacatacctctattatgggcccgttcgctggaattaccggcaattgtaggtacaaataatgcaaccgca atgattaacagcggtgattatttagtacttgatgcaatcaataacgctgtttatgtgaatccggctcaagacgtgattgacggcttaaaag cccaacaagcaaaattagcggaagaaaaagcggaattagctaaattaaaagatttaccggcagtaacattggacggtcaccgtgtt gaagtggtggcgaatatcggtacgattcgtgactgtgagggtgcggatcgtaacggtgcggaaggtgtcggtttataccgtaccgagtt cctgttcatggatcgtgaccaactgccttcagaagaagaacaatttatcgcttataaagaagtggtagaagcgatgaacggtcgccag gtggtattacgtaccatggatattggtggagataaagaattaccttatatgaatctgccaaaagaaatgaatccgttcttaggctggcgtg cggttcgtatcgcattggatcgtcgcgaaatcttaaatgctcaattgcgtgcggtattacgtgcttccgcattcggtaaattagcggtaatgt tcccgatgattatttccgttgaagaaattcgcgaattgaaatccgttatcgaaactttaaaacaagaattacgcaccgaaggtaaagcct ttgatgaaaatattcaaatcggtgtaatgtgtgaaacgccgtcagctgcagtaaatgcaaaattcttagcaaaagaagtggacttcttca gtatcggtactaatgatttaactcaatatactttagcggttgaccgtggtaatgaaatgatttcacatttatataatccaatgtcaccttcagta ttaagtttaattaaacaggttattgacgcctctcataccgaaggcaaatggactggtatgtgcggtgagttagccggtgatgaaaaagc cactatttattattaggtatgggattagacgaattcagcatgagcgctatttccgttcctcgtattaaaaaattggttcgtagtgttaattttgc cgaagcaaaagcattagcggataaagccctgcaattaccgactgctgccgaaattgaaaaattagttgctgattttttagctgaaaaaa cattaaattag
```

SEQ ID NO: 4 (amino acid sequence of the enzyme encoded by the above ptsA-gene)
MISGIPASPGIVFGKALVLKEEKIVLDMQKIAEDQVETEVARFYEGRTAAVEQLSAIRDRAEKTLG

EEKAAIFEGHLMILEDEELEEEIIDYLRSNKVNAGVAASKIIDQQVAMLADIDDEYLKERAGDIRDI

GNRLIKNILGMKIVDLGEINEESILVAYDLTPSETAQLNLDKVLGFITDIGGRTSHTSIMARSLELP

AIVGTNNATAMINSGDYLVLDAINNAVYVNPAQDVIDGLKAQQAKLAEEKAELAKLKDLPAVTLD

GHRVEVVANIGTIRDCEGADRNGAEGVGLYRTEFLFMDRDQLPSEEEQFIAYKEVVEAMNGRQ

VVLRTMDIGGDKELPYMNLPKEMNPFLGWRAVRIALDRREILNAQLRAVLRASAFGKLAVMFP

MIISVEEIRELKSVIETLKQELRTEGKAFDENIQIGVMCETPSAAVNAKFLAKEVDFFSIGTNDLTQ

YTLAVDRGNEMISHLYNPMSPSVLSLIKQVIDASHTEGKWTGMCGELAGDEKATILLLGMGLDE

FSMSAISVPRIKKLVRSVNFAEAKALADKALQLPTAAEIEKLVADFLAEKTLN

SEQ ID NO: 5 (nucleotide sequence of ptsH-gene from strain DD1)
atgtattcaaaagatgttgaaattacagctcctaacggcttacacactcgtccggctgcacaatttgtaaaagaagcaaaagcgtttgc atctgatgtaacagtgacttctgccggtaaaagtgcaagtgcgaaagtttattcaaattacaaactttaggcttaactcaaggaactgt aattacaatttcagctgaaggcgaagatgagcaaaatgctgttgaccatttagttgcattaattcctacattagaataa SEQ ID NO: 6 (amino acid sequence of the enzyme encoded by the above ptsH-gene)
MYSKDVEITAPNGLHTRPAAQFVKEAKAFASDVTVTSAGKSASAKSLFKLQTLGLTQGTVITISA

EGEDEQNAVDHLVALIPTLE

SEQ ID NO: 7 (nucleotide sequence of ldhA-gene from strain DD1)
ttgacaaaatcagtatgtttaaataaggagctaactatgaaagttgccgtttacagtactaaaaattatgatcgcaaacatctggatttgg cgaataaaaaatttaattttgagcttcatttcttttgattttttacttgatgaacaaaccgcgaaaatggcggagggcgccgatgccgtctgta ttttcgtcaatgatgatgcgagccgccgtgttaacaaagttggcgcaaatcggagtgaaaattatcgctttacgttgtgccggttttaat aatgtggatttggaggcggcaaaagagctgggattaaaagtcgtacgggtgcctgcgtattcgccggaagccgttgccgagcatgcg atcggattaatgctgactttaaaccgccgtatccataaggcttatcagcgtacccgcgatgcgaattttctctggaaggattggtcggtttt aatatgttcggcaaaaccgccggagtgattggtacgggaaaaatcggcttggcggcattcgcattttaaaggcttcggtatggacgtt ctggcgtttgatccttttaaaaatccggcggcggaagcgttgggcgcaaaatatgtcggtttagacgagctttatgcaaaatcccatgtta
```

-continued tcactttgcattgcccggctacggcggataattatcatttattaaatgaagcggcttttaataaaatgcgcgacggtgtaatgattattaata ccagccgcggcgttttaattgacagccgggcggcaatcgaagcgttaaaacggcagaaaatcggcgctctcggtatggatgtttatg aaaatgaacgggatttgttttcgaggataaatctaacgatgttattacggatgatgtattccgtcgcctttcttcctgtcataatgtgctttttac cggtcatcaggcgttttaacggaagaagcgctgaataatatcgccgatgtgactttatcgaatattcaggcggtttccaaaaatgcaac gtgcgaaaatagcgttgaaggctaa SEQ ID NO: 8 (amino acid sequence of LdhA from strain DD1)
MTKSVCLNKELTMKVAVYSTKNYDRKHLDLANKKFNFELHFFDFLLDEQTAKMAEGADAVCIFV

NDDASRPVLTKLAQIGVKIIALRCAGFNNVDLEAAKELGLKVVRVPAYSPEAVAEHAIGLMLTLN

RRIHKAYQRTRDANFSLEGLVGFNMFGKTAGVIGTGKIGLAAIRILKGFGMDVLAFDPFKNPAAE

ALGAKYVGLDELYAKSHVITLHCPATADNYHLLNEAAFNKMRDGVMIINTSRGVLIDSRAAIEAL

KRQKIGALGMDVYENERDLFFEDKSNDVITDDVFRRLSSCHNVLFTGHQAFLTEEALNNIADVT

LSNIQAVSKNATCENSVEG

SEQ ID NO: 9 (nucleotide sequence of pflA-gene from strain DD1)
atgtcggttttaggacgaattcattcatttgaaacctgcgggacagttgacgggccgggaatccgctttatttttattttacaaggctgcttaa tgcgttgtaaatactgccataatagagacacctgggatttgcacggcggtaaagaaatttccgttgaagaattaatgaaagaagtggtg acctatcgccatttatgaacgcctcgggcggcggagttaccgcttccggcggtgaagctattttacaggcggaatttgtacgggactgg ttcagagcctgccataaagaaggaattaatacttgcttggataccaacggtttcgtccgtcatcatgatcatattattgatgaattgattgat gacacgatcttgtgttgcttgacctgaaagaaatgaatgaacgggttcacgaaagcctgattggcgtgccgaataaaagagtgctcg aattcgcaaaatatttagcggatcgaaatcagcgtacctggatccgccatgttgtagtgccgggttatacagatagtgacgaagatttgc acatgctggggaatttcattaaagatatgaagaatatcgaaaaagtggaattattaccttatcaccgtctaggcgcccataaatgggaa gtactcggcgataaatacgagcttgaagatgtaaaaccgccgacaaaagaattaatggagcatgttaaggggttgcttgcaggctac gggcttaatgtgacatattag SEQ ID NO: 10 (amino acid sequence of PflA from strain DD1)
MSVLGRIHSFETCGTVDGPGIRFILFLQGCLMRCKYCHNRDTWDLHGGKEISVEELMKEVVTY

RHFMNASGGGVTASGGEAILQAEFVRDWFRACHKEGINTCLDTNGFVRHHDHIIDELIDDTDLV

LLDLKEMNERVHESLIGVPNKRVLEFAKYLADRNQRTWIRHVVVPGYTDSDEDLHMLGNFIKD

MKNIEKVELLPYHRLGAHKWEVLGDKYELEDVKPPTKELMEHVKGLLAGYGLNVTY

SEQ ID NO: 11 (nucleotide sequence of pflD-gene from strain DD1)
atggctgaattaacagaagctcaaaaaaaagcatgggaaggattcgttcccggtgaatggcaaaacggcgtaaatttacgtgactttt atccaaaaaaactatactccgtatgaaggtgacgaatcattcttagctgatgcgactcctgcaaccagcgagttgtggaacagcgtga tggaaggcatcaaaatcgaaaacaaaactcacgcacctttagatttcgacgaacatactccgtcaactatcacttctcacaagcctgg ttatatcaataaagatttagaaaaaatcgttggtcttcaaacagacgctccgttaaaaacgtgcaattatgccgtacggcggtatcaaaat gatcaaaggttcttgcgaagtttacggtcgtaaattagatccgcaagtagaatttatttcaccgaatatcgtaaaacccataaccaagg cgtattcgacgtttatacgccggatattttacgctgccgtaaatcaggcgtgttaaccggtttaccggatgcttacggtcgtggtcgtattatc ggtgactaccgtcgtttagcggtatacgtgattgattacctgatgaaagataaaaaagcccaattcgattcattacaaccgcgtttggaa gcgggcgaagacattcaggcaactatccaattacgtgaagaaattgccgaacaacaccgcgctttaggcaaaatcaaagaaatgg cggcatcttacggttacgacatttccggccctgcgacaaacgcacaggaagcaatccaatggacatattttgcttatctggcagcggtt aaatcacaaaacggtgcggcaatgtcattcggtcgtacgtctacattcttagatatctatatcgaacgtgacttaaaacgcggtttaatca ctgaacaacaggcgcaggaattaatggaccacttagtaatgaaattacgtatggttcgtttcttacgtacgccggaatacgatcaattatt ctcaggcgacccgatgtgggcaaccgaaactatcgccggtatgggcttagacggtcgtccgttggtaactaaaaacagcttccgcgt attacatactttatacactatgggtacttctccggaaccaaacttaactattctttggtccgaacaattacctgaagcgttcaaacgtttctgt gcgaaagtatctattgatacttcctccgtacaatacgaaaatgatgacttaatgcgtcctgacttcaacaacgatgactatgcaatcgcat gctgcgtatcaccgatggtcgtaggtaaacaaatgcaattcttcggtgcgcgcgcaaacttagctaaaactatgttatacgcaattaac -continued ggcggtatcgatgagaaaaatggtatgcaagtcggtcctaaaactgcgccgattacagacgaagtattgaatttcgataccgtaatcg aacgtatggacagtttcatggactggttggcgactcaatatgtaaccgcattgaacatcatccacttcatgcacgataaatatgcatatg aagcggcattgatggcgttccacgatcgcgacgtattccgtacaatggcttgcggtatcgcgggtctttccgtggctgcggactcattatc cgcaatcaaatatgcgaaagttaaaccgattcgcggcgacatcaaagataaagacggtaatgtcgtggcctcgaatgttgctatcga cttcgaaattgaaggcgaatatccgcaattcggtaacaatgatccgcgtgttgatgatttagcggtagacttagttgaacgtttcatgaaa aaagttcaaaaacacaaaacttaccgcaacgcaactccgacacaatctatcctgactatcacttctaacgtggtatacggtaagaaa accggtaatactccggacggtcgtcgagcaggcgcgccattcggacccgggtgcaaacccaatgcacggtcgtgaccaaaaaggt gcggttgcttcacttacttctgtggctaaacttccgttcgcttacgcgaaagacggtatttcatataccttctctatcgtaccgaacgcattag gtaaagatgacgaagcgcaaaaacgcaaccttgccggtttaatggacggttatttccatcatgaagcgacagtggaaggcggtcaa cacttgaatgttaacgttcttaaccgtgaaatgttgttagacgcgatggaaaatccggaaaaatacccgcaattaaccattcgtgtttcag gttacgcggttcgtttcaactcattaactaaagagcaacaacaagacgtcatcactcgtacgtttacacaatcaatgtaa SEQ ID NO: 12 (amino acid of PflD from strain DD1)
MAELTEAQKKAWEGFVPGEWQNGVNLRDFIQKNYTPYEGDESFLADATPATSELWNSVMEGI

KIENKTHAPLDFDEHTPSTITSHKPGYINKDLEKIVGLQTDAPLKRAIMPYGGIKMIKGSCEVYGR

KLDPQVEFIFTEYRKTHNQGVFDVYTPDILRCRKSGVLTGLPDAYGRGRIIGDYRRLAVYGIDYL

MKDKKAQFDSLQPRLEAGEDIQATIQLREEIAEQHRALGKIKEMAASYGYDISGPATNAQEAIQ

WTYFAYLAAVKSQNGAAMSFGRTSTFLDIYIERDLKRGLITEQQAQELMDHLVMKLRMVRFLRT

PEYDQLFSGDPMWATETIAGMGLDGRPLVTKNSFRVLHTLYTMGTSPEPNLTILWSEQLPEAF

KRFCAKVSIDTSSVQYENDDLMRPDFNNDDYAIACCVSPMVVGKQMQFFGARANLAKTMLYAI

NGGIDEKNGMQVGPKTAPITDEVLNFDTVIERMDSFMDWLATQYVTALNIIHFMHDKYAYEAAL

MAFHDRDVFRTMACGIAGLSVAADSLSAIKYAKVKPIRGDIKDKDGNVVASNVAIDFEIEGEYPQ

FGNNDPRVDDLAVDLVERFMKKVQHKTYRNATPTQSILTITSNVVYGKKTGNTPDGRRAGAP

FGPGANPMHGRDQKGAVASLTSVAKLPFAYAKDGISYTFSIVPNALGKDDEAQKRNLAGLMDG

YFHHEATVEGGQHLNVNVLNREMLLDAMENPEKYPQLTIRVSGYAVRFNSLTKEQQQDVITRT

FTQSM

SEQ ID NO: 13 (nucleotide sequence of wcaJ-gene from strain DD1)
atgataaaacgccttttcgatattgttgtcgcattgatagcattgattttgttttcgcccttatatttgtttgtggcttataaggtaaaacaaaattt gggatcaccggtgttatttaaacaaacccgccccggattgcatggtaaaccctttgagatgattaagttcagaacaatgaaagacggc gcagatgaaaacggtaatattttgccggatgcggagcgcttaacacctttcggcaaaatgttgcgcgctaccagtctggacgagttgcc ggaactttggaatgtattaaaggtgatatgagtctggtggggccgcgtcctctactgatggaatatttgccgctgtataacgaaagaca ggctaagcgccatgaagtgaaacccggaattaccggttatgcacaggtaaacggtcgcaatgccatcagttgggagcagaaatttg aattggatgcctggtatgttgaacatcaatccttgtggctggatttgaaaattatcgcaaagaccatccaaaaagtgatcgcaaaagac gatattaatgcggcagatgatgccaccatgcctaaatttgaagggaataaaaaatcatga SEQ ID NO: 14 (amino acid sequence of the enzyme encoded by the above wcaJ-gene)
MIKRLFDIVVALIALILFSPLYLFVAYKVKQNLGSPVLFKQTRPGLHGKPFEMIKFRTMKDGADEN

GNILPDAERLTPFGKMLRATSLDELPELWNVLKGDMSLVGPRPLLMEYLPLYNERQAKRHEVK

PGITGYAQVNGRNAISWEQKFELDAWYVEHQSLWLDLKIIAKTIQKVIAKDDINAADDATMPKFE

GNKKS

SEQ ID NO: 15 (nucleotide sequence of pykA-gene from strain DD1)
atgtccagaagattaagaagaacgaaaatcgtatgtacaatggggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat -continued

```
atcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacattaaacttatgc gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa
```

SEQ ID NO: 16 (amino acid sequence of PykA from strain DD1)
MSRRLRRTKIVCTMGPATDKGNNLEKIIAAGANVVRMNFSHGTPEDHIGRAEKVREIAHKLGKH

VAILGDLQGPKIRVSTFKEGKIFLNIGDKFILDAEMPKGEGNQEAVGLDYKTLPQDVVPGDILLLD

DGRVQLKVLATEGAKVFTEVTVGGPLSNNKGINKLGGGLSADALTEKDKADIITAARIGVDYLAV

SFPRSSADLNYARQLAKDAGLDAKIVAKVERAETVETDEAMDDIINAADVIMVARGDLGVEIGDP

ELVGVQKKLIRRSRQLNRVVITATQMMESMISNPMPTRAEVMDVANAVLDGTDAVMLSAETAA

GQYPAETVAAMAKVALGAEKMPSINVSKHRMNVQFESIEESVAMSAMYAANHMRGVAAIITLT

SSGRTARLMSRISSGLPIFALSRNESTLNLCALYRGVTPVHFDKDSRTSEGATAAVQLLKDEGF

LVSGDLVLLTQGDASSSSGTNLCRTLIVE

SEQ ID NO: 17 (complete nucleotide sequence of plasmid pSacB)
```
tcgagaggcctgacgtcgggcccggtaccacgcgtcatatgactagttcggacctagggatatcgtcgacatcgatgctcttctgcgtt aattaacaattgggatcctctagactccataggccgcttcctggctttgcttccagatgtatgctctcctccggagagtaccgtgactttatt ttcggcacaaatacaggggtcgatggataaatacggcgatagtttcctgacggatgatccgtatgtaccggcggaagacaagctgca aacctgtcagatggagattgatttaatggcggatgtgctgagagcaccgccccgtgaatccgcagaactgatccgctatgtgtttgcgg atgattggccggaataaataaagccgggcttaatacagattaagcccgtatagggtattattactgaataccaaacagcttacggagg acggaatgttacccattgagacaaccagactgccttctgattattaatatttttcactattaatcagaaggaataaccatgaatttttacccg gattgacctgaataccctggaatcgcagggaacactttgccctttatcgtcagcagattaaatgcggattcagcctgaccaccaaactcg atattaccgctttgcgtaccgcactggcggagacaggttataagtttatccgctgatgatttacctgatctcccgggctgttaatcagtttcc ggagttccggatggcactgaaagacaatgaacttatttactgggaccagtcagacccggtctttactgtctttcataaagaaaccgaaa cattctctgcactgtcctgccgttatttttccggatctcagtgagtttatggcaggttataatgcggtaacggcagaatatcagcatgatacca gattgtttccgcagggaaatttaccggagaatcacctgaatatatcatcattaccgtgggtgagttttgacgggatttaacctgaacatca ccggaaatgatgattatttttgccccggttttacgatggcaaagtttcagcaggaaggtgaccgcgtattattacctgtttctgtacaggttc atcatgcagtctgtgatggctttcatgcagcacggttattaatacacttcagctgatgtgtgataacatactgaaataaattaattaattctg tatttaagccaccgtatccggcaggaatggtggcttttttttatattttaaccgtaatctgtaatttcgtttcagactggttcaggatgagctcg cttgactcctgttgatagatccagtaatgacctcagaactccatctggatttgttcagaacgctcggttgccgccgggcgttttttattggtg agaatccaagcactagcggcgcgccggccggcccggtgtgaaataccgcacagatgcgtaaggagaaaataccgcatcaggcg ctcttccgcttcctcgctcactgactcgctgcgctcggtcgttcggctgcggcgagcggtatcagctcactcaaaggcggtaatacggtt atccacagaatcaggggataacgcaggaaagaacatgtgagcaaaaggccagcaaaaggccaggaaccgtaaaaaggccgc
```

```
gttgctggcgttttccataggctccgcccccctgacgagcatcacaaaaatcgacgctcaagtcagaggtggcgaaacccgacagg
actataaagataccaggcgtttccccctggaagctccctcgtgcgctctcctgttccgaccctgccgcttaccggatacctgtccgcctttc
tcccttcgggaagcgtggcgctttctcatagctcacgctgtaggtatctcagttcggtgtaggtcgttcgctccaagctgggctgtgtgcac
gaaccccccgttcagcccgaccgctgcgccttatccggtaactatcgtcttgagtccaacccggtaagacacgacttatcgccactgg
cagcagccactggtaacaggattagcagagcgaggtatgtaggcggtgctacagagttcttgaagtggtggcctaactacggctaca
ctagaaggacagtatttggtatctgcgctctgctgaagccagttaccttcggaaaaagagttggtagctcttgatccggcaaacaaacc
accgctggtagcggtggttttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatccttttaaagg
ccggccgcggccgccatcggcatttt ctttt gcgtttt tatttgttaactgttaattgtccttgttcaaggatgctgtcttt gacaacagatgttttct
tgcctttgatgttcagcaggaagctcggcgcaaacgttgattgtttgtctgcgtagaatcctctgtttgtcatatagcttgtaatcacgacatt
gtttcctttcgcttgaggtacagcgaagtgtgagtaagtaaaggttacatcgttaggatcaagatccatttttaacacaaggccagttttgtt
cagcggcttgtatgggccagttaaagaattagaaacataaccaagcatgtaaatatcgttagacgtaatgccgtcaatcgtcatttttgat
ccgcgggagtcagtgaacaggtaccatttgccgttcattt aaagacgttcgcgcgttcaatttcatctgttactgtgttagatgcaatcagc
ggtttcatcactttttt cagtgtgtaatcatcgtttagctcaatcataccgagagcgccgtttgctaactcagccgtgcgttttttatcgctttgca
gaagttttt gactttcttgacggaagaatgatgtgcttttgccatagtatgctttgttaaataaagattcttcgccttggtagccatcttcagttcc
agtgtttgcttcaaatactaagtatttgtggcctttatcttctacgtagtgaggatctctcagcgtatggttgtcgcctgagctgtagttgccttc
atcgatgaactgctgtacattttgatacgttttccgtcaccgtcaaagattgatttataatcctctacaccgttgatgttcaaagagctgtctg
atgctgatacgttaacttgtgcagttgtcagtgtttgtttgccgtaatgtttaccggagaaatcagtgtagaataaacggatttttccgtcaga
tgtaaatgtggctgaacctgaccattcttgtgtttggtcttttaggatagaatcatttgcatcgaatttgtcgctgtctttaaagacgcggccag
cgttttt ccagctgtcaatagaagtttcgccgacttttt gatagaacatgtaaatcgatgtgtcatccgcattttt aggatctccggctaatgc
aaagacgatgtggtagccgtgatagtttgcgacagtgccgtcagcgttttgtaatggccagctgtcccaaacgtccaggcctttt gcaga
agagatatttttaattgtggacgaatcaaattcagaaacttgatatttttcattttttt gctgttcagggatttgcagcatatcatggcgtgtaata
tgggaaatgccgtatgtttccttatatggcttttggttcgttt ctttcgcaaacgcttgagttgcgcctcctgccagcagtgcggtagtaaagg
ttaatactgttgcttgttttgcaaacttttt gatgttcatcgttcatgtctccttttttatgtactgtgttagcggtctgcttcttccagccctcctgtttga
agatggcaagttagttacgcacaataaaaaaagacctaaaatatgtaaggggtgacgccaaagtatacactttgcccttt acacatttt
aggtcttgcctgctttatcagtaacaaacccgcgcgatttactttt cgacctcattctattagactctcgtttggattgcaactggtctatttt cct
cttttgtttgatagaaaatcataaaaggatttgcagactacgggcctaaagaactaaaaaatctatctgtttcttttcattctctgtatttt tata
gtttctgttgcatgggcataaagttgccttttt aatcacaattcagaaaatatcataatatctcatttcactaaataatagtgaacggcaggt
atatgtgatgggttaaaaaggatcggcggccgctcgatttaaatc
```

SEQ ID NO: 18 (complete nucleotide sequence of plasmid pSacB_delta_ldhA)

```
tcgagaggcctgacgtcgggcccggtaccacgcgtcatatgactagttcggacctagggatgggtcagcctgaacgaaccgcactt
gtatgtaggtagttttgaccgcccgaatattcgttataccttggtggaaaaattcaaaccgatggagcaattatacaattttgtggcggcgc
aaaaaggtaaagcggtatcgtctattgcaacagccgtagcaaagtggagcgcattgcggaagccctgaagaaaagaggcatttc
cgcagccgcttatcatgcgggcatggaccgtcgcagcgggaagcggtgcaacaggcgtttcaacgggataatattcaagtggtgg
tggcgaccattgctttggtatggggatcaacaaatctaatgtgcgttttgtggcgcatttt gatttatctcgcagcattgaggcgtattatcag
gaaaccgggcgcgcggggcgggacgacctgccggcggaagcggtactgttttacgagccggcggattatgcctggttgcataaaat
tttattggaagagccggaaagcccgcaacgggatattaaacggcataagctggaagccatcggcgaatttgccgaaagccagacc
tgccgtcgtttagtgctgttaaattattt cggcgaaaaccgccaaacgccatgtaataactgtgatatctgcctcgatccgccgaaaaat
atgacggattattagacgcgcagaaaatcctttcgaccatttatcgcaccgggcaacgtttcggcacgcaatacgtaatcggcgtaatg
cgcggtttgcagaatcagaaaataaaagaaaatcaacatgatgagttgaaagtctacggaattggcaaagataaaagcaaagaat
actggcaatcggtaattcgtcagctgattcatttgggctttgtgcaacaaatcatcagcgatttcggcatggggaccagattacagctcac
```

-continued

```
cgaaagcgcgcgtcccgtgctgcgcggcgaagtgtctttggaactggccatgccgagattatcttccattaccatggtacaggctccgc aacgcaatgcggtaaccaactacgacaaagatttatttgcccgcctgcgtttcctgcgcaaacagattgccgacaaagaaaacattc cgccttatattgtgttcagtgacgcgaccttgcaggaaatgtcgttgtatcagccgaccagcaaagtggaaatgctgcaaatcaacggt gtcggcgccatcaaatggcagcgcttcggacagccttttatggcgattattaaagaacatcaggctttgcgtaaagcgggtaagaatc cgttggaattgcaatcttaaaattttttaacttttttgaccgcacttttaaggttagcaaattccaataaaaagtgcggtgggttttcgggaattttt aacgcgctgatttcctcgtcttttcaatttyttcgyctccatttgttcggyggttgccggatcctttcttgactgagatccataagagagtagaa tagcgccgcttatattttaatagcgtacctaatcgggtacgcttttttttatgcggaaaatccatatttttctaccgcacttttctttaaagatttat acttaagtctgtttgattcaatttatttggaggttttatgcaacacattcaactggctcccgatttaacattcagtcgcttaattcaaggattctg gcggttaaaaagctggcggaaatcgccgcaggaattgcttacattcgttaagcaaggattagaattaggcgttgatacgctggatcat gccgcttgttacggggcttttacttccgaggcggaattcggacgggcgctggcgctggataaatccttgcgcgcacagcttactttggtg accaaatgcgggattttgtatcctaatgaagaattacccgatataaaatcccatcactatgacaacagctaccgccatattatgtggtcg gcgcaacgttccattgaaaaactgcaatgcgactatttagatgtattgctgattcaccgwctttctccctgtgcggatcccgaacaaatcg cgcgggcttttgatgaactttatcaaaccggraaagtacgttatttcggggtatctaactatacgccggctaagttcgccatgttgcaatctt atgtgaatcagccgttaatcactaatcaaattgagatttcgcctcttcatcgtcaggcttttgatgacggtaccctggattttttactggaaaa acgtattcaaccgatggcatggtcgccacttgccggcggtcgtttattcaatcaggatgagaacagtcgggcggtgcaaaaaacatta ctcgaaatcggtgaaacgaaaggagaaacccgtttagatacattggcttatgcctggttattggcgcatccggcaaaaattatgccggt tatggggtccggtaaaattgaacgggtaaaaagcgcggcggatgcgttacgaatttccttcactgaggaagaatggattaaggtttatg ttgccgcacagggacgggatattccgtaacatcatccgtctaatcctgcgtatctggggaaagatgcgtcatcgtaagaggtctataat attcgtcgttttgataagggtgccatatccggcacccgttaaaatcacattgcgttcgcaacaaaattattccttacgaatagcattcacct cttttaacagatgttgaatatccgtatcggcaaaaatatcctctatatttgcggttaaacggcgccgccagttagcatattgagtgctggttc ccggaatattgacgggttcggtcataccgagccagtcttcaggttggaatccccatcgtcgacatcgatgctcttctgcgttaattaacaa ttgggatcctctagactccataggccgctttcctggctttgcttccagatgtatgctctcctccggagagtaccgtgactttattttcggcaca aatacaggggtcgatggataaatacgcgatagtttcctgacggatgatccgtatgtaccggcggaagacaagctgcaaacctgtca gatggagattgatttaatggcggatgtgctgagagcaccgccccgtgaatccgcagaactgatccgctatgtgtttgcggatgattggc cggaataaataaagccgggcttaatacagattaagcccgtatagggtattattactgaataccaaacagcttacggaggacggaatg ttacccattgagacaaccagactgccttctgattattaatatttttcactattaatcagaaggaataaccatgaattttacccggattgacct gaatacctggaatcgcagggaacactttgcccttatcgtcagcagattaaatgcggattcagcctgaccaccaaactcgatattaccg ctttgcgtaccgcactggcggagacaggttataagttttatccgctgatgatttacctgatctcccgggctgttaatcagtttccggagttcc ggatggcactgaaagacaatgaacttatttactgggaccagtcagacccggtctttactgtctttcataaagaaaccgaaacattctctg cactgtcctgccgttattttccggatctcagtgagtttatggcaggttataatgcggtaacggcagaatatcagcatgataccagattgtttc cgcagggaaatttaccggagaatcacctgaatatatcatcattaccgtgggtgagttttgacgggattttaacctgaacatcaccggaaa tgatgattattttgccccggttttttacgatggcaaagtttcagcaggaaggtgaccgcgtattattacctgtttctgtacaggttcatcatgca gtctgtgatggctttcatgcagcacggtttattaatacacttcagctgatgtgtgataacatactgaaataaattaattaattctgtatttaagc caccgtatccggcaggaatggtggcttttttttatattttaaccgtaatctgtaatttcgtttcagactggttcaggatgagctcgcttggactc ctgttgatagatccagtaatgacctcagaactccatctgatttgttcagaacgctcggttgccgccgggcgttttttattggtgagaatcca agcactagcggcgcgccggccggcccggtgtgaaataccgcacagatgcgtaaggagaaaataccgcatcaggcgctcttccgct tcctcgctcactgactcgctgcgctcggtcgttcggctgcggcgagcggtatcagctcactcaaaggcggtaatacggttatccacaga atcaggggataacgcaggaaagaacatgtgagcaaaaggccagcaaaaggccaggaaccgtaaaaaggccgcgttgctggcg ttttcataggctccgcccccctgacgagcatcacaaaaatcgacgctcaagtcagaggtggcgaaacccgacaggactataaag ataccaggcgtttccccctggaagctccctcgtgcgctctcctgttccgaccctgccgcttaccggatacctgtccgcctttctcccttcgg
```

-continued

```
gaagcgtggcgctttctcatagctcacgctgtaggtatctcagttcggtgtaggtcgttcgctccaagctgggctgtgtgcacgaaccccc cgttcagcccgaccgctgcgccttatccggtaactatcgtcttgagtccaacccggtaagacacgacttatcgccactggcagcagcc actggtaacaggattagcagagcgaggtatgtaggcggtgctacagagttcttgaagtggtggcctaactacggctacactagaagg acagtatttggtatctgcgctctgctgaagccagttaccttcggaaaaagagttggtagctcttgatccggcaaacaaaccaccgctggt agcggtggttttttttgtttgcaagcagcagattacgcgcagaaaaaaaggatctcaagaagatcctttgatcttttctacggggtctgacg ctcagtggaacgaaaactcacgttaagggattttggtcatgagattatcaaaaaggatcttcacctagatccttttaaaggccggccgc ggccgccatcggcattttcttttgcgttttatttgttaactgttaattgtccttgttcaaggatgctgtctttgacaacagatgttttcttgcctttgat gttcagcaggaagctcggcgcaaacgttgattgtttgtctgcgtagaatcctctgtttgtcatatagcttgtaatcacgacattgtttcctttcg cttgaggtacagcgaagtgtgagtaagtaaaggttacatcgttaggatcaagatccattttaacacaaggccagttttgttcagcggctt gtatgggccagttaaagaattagaaacataaccaagcatgtaaatatcgttagacgtaatgccgtcaatcgtcatttttgatccgcggga gtcagtgaacaggtaccatttgccgttcattttaaagacgttcgcgcgttcaatttcatctgttactgtgttagatgcaatcagcggtttcatc actttttttcagtgtgtaatcatcgtttagctcaatcataccgagagcgccgtttgctaactcagccgtgcgttttttatcgctttgcagaagttttt gactttcttgacggaagaatgatgtgcttttgccatagtatgctttgttaaataaagattcttcgccttggtagccatcttcagttccagtgtttg cttcaaatactaagtatttgtggcctttatcttctacgtagtgaggatctctcagcgtatggttgtcgcctgagctgtagttgccttcatcgatg aactgctgtacattttgatacgttttccgtcaccgtcaaagattgatttataatcctctacaccgttgatgttcaaagagctgtctgatgctga tacgttaacttgtgcagttgtcagtgtttgtttgccgtaatgtttaccggagaaatcagtgtagaataaacggattttccgtcagatgtaaat gtggctgaacctgaccattcttgtgtttggtcttttaggatagaatcatttgcatcgaatttgtcgctgtctttaaagacgcggccagcgttttc cagctgtcaatagaagtttcgccgacttttgatagaacatgtaaatcgatgtgtcatccgcattttaggatctccggctaatgcaaagac gatgtggtagccgtgatagtttgcgacagtgccgtcagcgttttgtaatggccagctgtcccaaacgtccaggccttttgcagaagagat atttttaattgtggacgaatcaaattcagaaacttgatattttcattttttgctgttcagggatttgcagcatatcatggcgtgtaatatgggaa atgccgtatgtttccttatatggcttttggttcgtttctttcgcaaacgcttgagttgcgcctcctgccagcagtgcggtagtaaaggttaatact gttgcttgttttgcaaacttttttgatgttcatcgttcatgtctccttttttatgtactgtgttagcggtctgcttcttccagccctcctgtttgaagatgg caagttagttacgcacaataaaaaagacctaaaatatgtaagggtgacgccaaagtatacactttgccctttacacatttttaggtctt gcctgctttatcagtaacaaacccgcgcgatttacttttcgacctcattctattagactctcgtttggattgcaactggtctattttcctcttttgttt gatagaaaatcataaaaggatttgcagactacggggcctaaagaactaaaaaatctatctgttttcttttcattctctgtatttttttatagtttctgt tgcatgggcataaagttgccttttaatcacaattcagaaaatatcataatatctcatttcactaaataatagtgaacggcaggtatatgtg atgggttaaaaaggatcggcggccgctcgatttaaatc
```

SEQ ID NO: 19 (complete nucleotide sequence of plasmid pSacB_delta_pflA)

```
tcgagtcaatgcggatttgacttatgatgtggcaaacaaccgatttccgattattactacacgtaaaagttattggaaagcggcgattgcg gagtttctgggttatatccgcggctacgataatgcggcggatttccgtaaattaggagcaaaaacctgggatgccaacgctaatgaaa atcaggtatggctgaataaccctcatcgcaaaggcaccgacgacatggggcgcgtttacggcgtacagggcagagcctggcgtaa gcctaacggcgaaaccgttgatcaattacgcaaaattgtcaacaatttaagtcgcggcattgatgatcgcggcgaaattctgaccttttt aaacccgggcgaattcgatctcggttgtctgcgcccttgtatgtacaatcacacgttttctttgctgggcgatacgctttatttaaccagttat caacgctcctgacgtacctttaggcttgaatttcaatcaaattcaagtatttacattcttagctttaatggcgcagattaccggtaaaaaa gccggtcaggcatatcacaaaatcgtcaatgcgcatatttacgaagaccagctggaactaatgcgcgacgtgcagttaaaacgcga accgttcccgtcgccaaaactggaaattaatccggacattaaacccttgaagatttagaaacctgggtaaccatggatgatttcaacg tcgttggttaccaatgccacgaaccgataaaatatccgttctcggtataaaccgacaaaagtgcggtcaaaaatttaatattttcatctgtt atagaaaatattttttcaacataaaatctagggatgcctgtttggcgtccgtaaatacgcagaaaaatattaaattttttgaccgcactttttttc atctcaattaacagcctgataattcttatggatcaacaaattagctttgacgaaaaaatgatgaatcgagctcttttccttgccgacaagg cggaagcttagggggaaattcccgtaggtgccgtattggtggatgaacggggcaatatcattggtgaaggctggaacctctctattgtg aactcggatcccaccgcccatgccgaaattattgcgttgcgtaacgccgcgcagaaaatccaaaattaccgcctgctcaataccactt
```

-continued

```
tatacgtgactttagaaccctgcaccatgtgcgccggcgcgattttacacagccgaatcaaacgcttggtattcggggcgtccgattac aaaaccggtgcggtgggttccagatttcatttttttgaggattataaaatgaatcatgggggttgagatcacaagcggtgtcttacaggatc aatgcagtcagaagttaagccgcttttccaaaagcgcagggaacagaaaaaacaacaaaaagctaccgcacttttacaacaccc ccggcttaactcctctgaaaaatagtgacaaaaaaccgtcataatgtttacgacggttttttattctcttaatatgcccttaaataatcaac aaaatatagcaagaagattatagcaaagaatttcgttttttcagagaatagtcaaatcttcgcaaaaaactaccgcacttttatccgcttt aatcaggggaattaaaacaaaaaaattccgcctattgaggcggaatttattaagcaataagacaaactctcaattacattgattgtgta aacgtacgagtgatgacgtcttgttgttgctctttagttaatgagttgaaacgaaccgcgtaacctgaaacacgaatggttaattgcgggt attttttccggattttccatcgcgtctaacaacatttcacggttaagaacgttaacattcaagtgttgaccgccttccactgtcgcttcatgatg gaaataaccgtccattaaaccggcaaggttgcgttttttgcgcttcgtcatctttacctaatgcgttcggtacgatagagaaggtatatgaa ataccgtctttcgcgtaagcgaacggaagtttagccacagaagtaagtgaagcaaccgcaccttttttggtcacgaccgtgcattgggttt gcacccggtccgaatggcgcgcctgctcgacgaccgtccggagtattaccggttttcttaccgtataccacgttagaagtgatagtcag gatagattgtgtcggagttgcgttgcggtaagttttgtgttttttgaacttttttcatgaaacgttcaactaagtctaccgctaaatcatcaacac gcggatcattgttaccgaattgcggatattcgccttcaatttcgaagtcgatagcaacattcgaggccacgacattaccgtctttatctttga tgtcgccgcgaatcggtttaacttcgcatatttgattgcggataatgagtccgcagccacggaaagacccgcgataccgcaagccatt gtacggaatacgtcgcgatcgtggaacgccatcaatgccgcttcatatgcatatttatcgtgcatgaagtggatgatgttcaatgcggtta catattgagtcgccaaccagtccatgaaactgtccatacgttcgattacggtatcgaaattcaatacttcgtctgtaatcggcgcagtttta ggaccgacttgcataccattttctcatcgataccgccgttaattgcgtataacatagttttagctaagtttgcgcgcgcaccgaagaattg catttgtttacctacgaccatcggtgatacgcagcatgcgattgcatagtcatcgttgttgaagtcaggacgcattaagtcatcattttcgta ttgtacggaggaagtatcaatagatacttcgcacagaaacgtttgaacgcttcaggtaattgttcggaccaaagaatagttaagtttggt tccggagaagtacccatagtgtataaagtatgtaatacgcggaagctgttttttagttaccaacggacgaccgtctaagcccataccggc gatagtttcggttgccctctagactccataggccgctttcctggctttgcttccagatgtatgctctcctccggagagtaccgtgactttattttc ggcacaaatacagggggtcgatggataaatacggcgatagtttcctgacggatgatccgtatgtaccggcggaagacaagctgcaaa cctgtcagatggagattgatttaatggcggatgtgctgagagcaccgccccgtgaatccgcagaactgatccgctatgtgtttgcggat gattggccggaataaataaagccgggcttaatacagattaagcccgtataggtattattactgaataccaaacagcttacggaggac ggaatgttacccattgagacaaccagactgccttctgattattaatattttcactattaatcagaaggaataaccatgaattttacccggat tgacctgaatacctggaatcgcagggaacactttgccctttatcgtcagcagattaaatgcggattcagcctgaccaccaaactcgata ttaccgctttgcgtaccgcactggcggagacaggttataagttttatccgctgatgatttacctgatctcccgggctgttaatcagtttccgg agttccggatggcactgaaagacaatgaacttatttactgggaccagtcagacccggtctttactgtctttcataaagaaaccgaaaca ttctctgcactgtcctgccgttattttccggatctcagtgagtttatggcaggttataatgcggtaacggcagaatatcagcatgataccag attgtttccgcagggaaatttaccggagaatcacctgaatatatcatcattaccgtgggtgagttttgacgggatttaacctgaacatcac cggaaatgatgattattttgccccggttttttacgatggcaaagtttcagcaggaaggtgaccgcgtattattacctgtttctgtacaggttcat catgcagtctgtgatggctttcatgcagcacggtttattaatacacttcagctgatgtgtgataacatactgaaataaattaattaattctgta tttaagccaccgtatccggcaggaatggtggcttttttttatattttaaccgtaatctgtaatttcgtttcagactggttcaggatgagctcgctt ggactcctgttgatagatccagtaatgacctcagaactccatctggatttgttcagaacgctcggttgccgccgggcgttttttattggtgag aatccaagcactagcggcgcgccggccggcccggtgtgaaataccgcacagatgcgtaaggagaaaataccgcatcaggcgctc ttccgcttcctcgctcactgactcgctgcgctcggtcgttcggctgcggcgagcggtatcagctcactcaaaggcggtaatacggttatc cacagaatcaggggataacgcaggaaagaacatgtgagcaaaaggccagcaaaaggccaggaaccgtaaaaaggccgcgtt gctggcgttttccataggctccgcccccctgacgagcatcacaaaaatcgacgctcaagtcagaggtggcgaaacccgacaggac tataaagataccaggcgtttccccctggaagctccctcgtgcgctctcctgttccgaccctgccgcttaccggatacctgtccgcctttctc ccttcggaagcgtggcgctttctcatagctcacgctgtaggtatctcagttcggtgtaggtcgttcgctccaagctgggctgtgtgcacg aaccccccgttcagcccgaccgctgcgccttatccggtaactatcgtcttgagtccaacccggtaagacacgacttatcgccactggc
``` agcagccactggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccggcaaacaaacca ccgctggtagcggtggttttttttgtttgcaagcagcagattacgcgcagaaaaaaaggatctcaagaagatcctttgatcttttctacggg gtctgacgctcagtggaacgaaaactcacgttaagggattttggtcatgagattatcaaaaaggatcttcacctagatccttttaaaggc cggccgcggccgccatcggcattttcttttgcgttttatttgttaactgttaattgtccttgttcaaggatgctgtctttgacaacagatgttttctt gcctttgatgttcagcaggaagctcggcgcaaacgttgattgtttgtctgcgtagaatcctctgtttgtcatatagcttgtaatcacgacattg tttcctttcgcttgaggtacagcgaagtgtgagtaagtaaaggttacatcgttaggatcaagatccattttaacacaaggccagttttgttc agcggcttgtatgggccagttaaagaattagaaacataaccaagcatgtaaatatcgttagacgtaatgccgtcaatcgtcattttgatc cgcgggagtcagtgaacaggtaccatttgccgttcattttaaagacgttcgcgcgttcaatttcatctgttactgtgttagatgcaatcagc ggtttcatcactttttcagtgtgtaatcatcgtttagctcaatcataccgagagcgccgtttgctaactcagccgtgcgttttttatcgctttgca gaagttttgactttcttgacggaagaatgatgtgcttttgccatagtatgctttgttaaataaagattcttcgccttggtagccatcttcagttcc agtgtttgcttcaaatactaagtatttgtggcctttatcttctacgtagtgaggatctctcagcgtatggttgtcgcctgagctgtagttgccttc atcgatgaactgctgtacattttgatacgttttccgtcaccgtcaaagattgatttataatcctctacaccgttgatgttcaaagagctgtctg atgctgatacgttaacttgtgcagttgtcagtgtttgtttgccgtaatgtttaccggagaaatcagtgtagaataaacggattttttccgtcaga tgtaaatgtggctgaacctgaccattcttgtgtttggtcttttaggatagaatcatttgcatcgaatttgtcgctgtctttaaagacgcggccag cgtttttccagctgtcaatagaagtttcgccgacttttttgatagaacatgtaaatcgatgtgtcatccgcatttttaggatctccggctaatgc aaagacgatgtggtagccgtgatagtttgcgacagtgccgtcagcgttttgtaatggccagctgtcccaaacgtccaggccttttgcaga agagatattttaattgtggacgaatcaaattcagaaacttgatattttttcatttttttgctgttcagggatttgcagcatatcatggcgtgtaata tgggaaatgccgtatgtttccttatatggcttttggttcgtttctttcgcaaacgcttgagttgcgcctcctgccagcagtgcggtagtaaagg ttaatactgttgcttgttttgcaaactttttgatgttcatcgttcatgtctcctttttatgtactgtgttagcggtctgcttcttccagccctcctgtttga agatggcaagttagttacgcacaataaaaaaagacctaaaatatgtaaggggtgacgccaaagtatacactttgcccttacacattt aggtcttgcctgctttatcagtaacaaacccgcgcgatttacttttcgacctcattctattagactctcgtttggattgcaactggtctatttttcct cttttgtttgatagaaaatcataaaaggatttgcagactacgggcctaaagaactaaaaaatctatctgttcttttcattctctgtatttttata gtttctgttgcatgggcataaagttgcctttttaatcacaattcagaaaatatcataatatctcatttcactaaataatagtgaacggcaggt atatgtgatgggttaaaaaggatcggcggccgctcgatttaaatc SEQ ID NO: 20 (complete nucleotide sequence of plasmid pSacB_pykA1)
tcgagcagaagattaagaagaacgaaaatcgtatgtacaatggggcctgcaacagacaaaggcaataatttagaaaaaatcattg ctgccggtgcaaacgttgtacgtatgaacttctcccacggtacgcccgaagatcatatcggtcgtgctgaaaaagtacgtgaaatcgct cataaattaggtaaacacgtagcaatcttaggtgacttacaaggccctaaaatccgtgtttctacttttaaagaaggcaaaattttcttaaa tatcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctagactccataggccgcttcctggctttgcttccagatgtatgctctcctccggagagtac cgtgactttattttcggcacaaatacaggggtcgatggataaatacggcgatagtttcctgacggatgatccgtatgtaccggcggaag -continued

```
acaagctgcaaacctgtcagatggagattgatttaatggcggatgtgctgagagcaccgccccgtgaatccgcagaactgatccgct
atgtgtttgcggatgattggccggaataaataaagccgggcttaatacagattaagcccgtatagggtattattactgaataccaaaca
gcttacggaggacggaatgttacccattgagacaaccagactgccttctgattattaatattttttcactattaatcagaaggaataaccat
gaattttacccggattgacctgaatacctggaatcgcagggaacactttgccctttatcgtcagcagattaaatgcggattcagcctgac
caccaaactcgatattaccgctttgcgtaccgcactggcggagacaggttataagttttatccgctgatgatttacctgatctcccgggct
gttaatcagtttccggagttccggatggcactgaaagacaatgaacttatttactgggaccagtcagacccggtctttactgtctttcataa
agaaaccgaaacattctctgcactgtcctgccgttattttccggatctcagtgagtttatggcaggttataatgcggtaacggcagaatat
cagcatgataccagattgtttccgcagggaaatttaccggagaatcacctgaatatatcatcattaccgtgggtgagttttgacgggattt
aacctgaacatcaccggaaatgatgattattttgccccggttttacgatggcaaagtttcagcaggaaggtgaccgcgtattattacctg
tttctgtacaggttcatcatgcagtctgtgatggctttcatgcagcacggtttattaatacacttcagctgatgtgtgataacatactgaaata
aattaattaattctgtatttaagccaccgtatccggcaggaatggtggctttttttttatattttaaccgtaatctgtaatttcgtttcagactggttc
aggatgagctcgcttggactcctgttgatagatccagtaatgacctcagaactccatctggatttgttcagaacgctcggttgccgccgg
gcgttttttattggtgagaatccaagcactagcggcgcgccggccggcccggtgtgaaataccgcacagatgcgtaaggagaaaat
accgcatcaggcgctcttccgcttcctcgctcactgactcgctgcgctcggtcgttcggctgcggcgagcggtatcagctcactcaaag
gcggtaatacggttatccacagaatcagggggataacgcaggaaagaacatgtgagcaaaaggccagcaaaaggccaggaacc
gtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccgg
atacctgtccgcctttctcccttcgggaagcgtggcgctttctcatagctcacgctgtaggtatctcagttcggtgtaggtcgttcgctccaa
gctgggctgtgtgcacgaaccccccgttcagcccgaccgctgcgccttatccggtaactatcgtcttgagtccaacccggtaagacac
gactatcgccactggcagcagccactggtaacaggattagcagagcgaggtatgtaggcggtgctacagagttcttgaagtggtgg
cctaactacggctacactagaaggacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagat
cctttgatcttttctacggggtctgacgctcagtggaacgaaaactcacgttaagggattttggtcatgagattatcaaaaaggatcttcac
ctagatccttttaaaggccggccgcggccgccatcggcattttcttttgcgtttttatttgttaactgttaattgtccttgttcaaggatgctgtcttt
gacaacagatgttttcttgcctttgatgttcagcaggaagctcggcgcaaacgttgattgtttgtctgcgtagaatcctctgtttgtcatatag
cttgtaatcacgacattgtttcctttcgcttgaggtacagcgaagtgtgagtaagtaaaggttacatcgttaggatcaagatccattttttaac
acaaggccagttttgttcagcggcttgtatgggccagttaaagaattagaaacataaccaagcatgtaaatatcgttagacgtaatgcc
gtcaatcgtcatttttgatccgcgggagtcagtgaacaggtaccatttgccgttcattttaaagacgttcgcgcgttcaatttcatctgttactg
tgttagatgcaatcagcggtttcatcactttttttcagtgtgtaatcatcgtttagctcaatcataccgagagcgccgtttgctaactcagccgt
gcgttttttatcgctttgcagaagttttgacttcttgacggaagaatgatgtgcttttgccatagtatgctttgttaaataaagattcttcgcctt
ggtagccatcttcagttccagtgtttgcttcaaatactaagtatttgtgccctttatcttctacgtagtgaggatctctcagcgtatggttgtcgc
ctgagctgtagttgccttcatcgatgaactgctgtacattttgatacgttttccgtcaccgtcaaagattgatttataatcctctacaccgttga
tgttcaaagagctgtctgatgctgatacgttaacttgtgcagttgtcagtgtttgttgccgtaatgttaccggagaaatcagtgtagaataa
acggattttccgtcagatgtaaatgtggctgaacctgaccattcttgtgtttggtcttttaggatagaatcatttgcatcgaatttgtcgctgtct
ttaaagacgcggccagcgttttccagctgtcaatagaagtttcgccgacttttttgatagaacatgtaaatcgatgtgtcatccgcatttttta
ggatctccggctaatgcaaagacgatgtggtagccgtgatagtttgcgacagtgccgtcagcgttttgtaatggccagctgtcccaaac
gtccaggccttttgcagaagagatatttttaattgtggacgaatcaaattcagaaacttgatattttttcattttttttgctgttcagggatttgcag
catatcatggcgtgtaatatgggaaatgccgtatgtttccttatatggcttttggttcgtttcttcgcaaacgcttgagttgcgcctcctgccag
cagtgcggtagtaaaggttaatactgttgcttgttttgcaaacttttttgatgttcatcgttcatgtctccttttttatgtactgtgttagcggtctgctt
cttccagcccctcctgtttgaagatggcaagttagttacgcacaataaaaaaagacctaaaatatgtaaggggtgacgccaaagtatac
```

-continued actttgcccttacacatttaggtcttgcctgctttatcagtaacaaacccgcgcgatttacttttcgacctcattctattagactctcgtttggat tgcaactggtctatttcctcttttgtttgatagaaaatcataaaggatttgcagactacgggcctaaagaactaaaaaatctatctgtttctt ttcattctctgtatttttatagtttctgttgcatgggcataaagttgccttttaatcacaattcagaaaatatcataatatctcatttcactaaata atagtgaacggcaggtatatgtgatgggttaaaaaggatcggcggccgctcgatttaaatc SEQ ID NO: 21 (complete nucleotide sequence of plasmid pSacB_wcaJ*)
tcgagtaagccgattcagctgatccgccacatggggaaaaagcctaatctgcggaatatgaaaccgataccagtccagtaaagttg acaaatcgacatcatattgctcaaccaagtattgaaaagcgttttcaccgcgatgatacaattcgaccagccggttaaataacgtttcac tccgttccggtgccaaacgagacgcaatatgcttataggcggaatacagaaaatcgatttccgcataaagcgtatcgtccaaatctaa aaccaacgctttatttttcataatgatgagccagtacttccgcgtcataccgcaacattaataaatccgcttcccagtcttcgaacgcagg aatcggctgattaaacaaatattcctgaatcaaccaacggggataattggctcccgccagataactcaacggataaccgccgccga acctaggggttaatttcaataccaagaatttcagccggtggattccttataaaatacttggattgttaagcaaccgcgcgccccggtaaac gggacaattttccgataattgcgtcacgatggcatttttctggtcacacctttgttaatttccccccgctctgacaaaattctctttctcggta ccgcacttttcagttcggaattttttatcaaaataacaatccacggtatattcgtcgtattccgccggcgaaatatattgcataaacattaattc gggattttccaattgctccggtgaaatatcttccggtttctccgccacaaaaattcctttacttaaactaccgttgtaaggcttcacaaaaac aggatattcaaattgaccttttcaaactgcttcggtaccgcaatatatgttcaataaacagttgattggttaatcgtttgtcgcgacatttttct gacaaactctgtatcactaacggaaataaaaataccttttctttaaaccgttgcagatgttcgcttaaaataagcaattccgtatcaatag tcggaataatcaattttcacgttattttcttcacagattttaagtaaggtcggaatatactccgcatcagtgacccggggtacaggaaaatgt ccgtcggccacataacaagccggcgccaactcgggatttaaatctacggttaacacttttccgtcacttactaactgcgataattccttttt aaacgcctgaacgagagaaacacgttgtccggccgatgtaacaagaatattcatgatttttattcccttcaaatttaggcatggtggcat catctgccgcattaatatcgtcttttgcgatcacttttggatggtctttgcgataattttcaaatccagccacaaggattgatgttcaacatac caggcatccaattcaaatttctgctcccaactgatggcattgcgaccgtttacctgtgcataaccggtaattccgggtttcacttcatggcg cttagcctgtctttcgttatacagcggcaaatattccatcagtagaggacgcggccccaccagactctatatcaccttttaatacattccaa agttccggcaactcgtccagactggtagcgcgcaacattttgccgaaaggtgttaagcgctccgcatccggcaaaatattaccgttttc atctgcgccgtctttcattgttctgaacttaatcatctcaaagggtttaccatgcaatccggggcgggtttgtttaaataacaccggtgatcc caaattttgttttaccttgataagccacaaacaaatataagggcgaaaacaaaatcaatgctatcaatgcgacaacaatatcgaaaag gcgtttatcatgaaaatctcctacgaccgaccaatttggggctgacaaaagtgccgttttcaccagaaccgtataaactaaaaccag gaaaagcggataccagactaacggcagtcttaatatggaagacggcacccaaacgatccaacaaaaattaataaaaataaataa aataaatatacgttctttccacgccaacaattgggtattcatcacatagataattgaatttaataaaaaatatataaatgccaaaaatgca aaaatgccaaatgccaaataaagttctataaagaagctatgcggattagtgtaacccaaagggaaacttaactttatttgatcgaaata ctgaatgtagtcccgcggtccataacccaaccataaaattttaaaattatctaaaaatgtcgtataaatttccgtccggtaacctacggac ttatcatcgcccatagaaaatattaccaatgaaaaacgttcaatcggacgctccagccaatcaattttggcgagcagaataaacacttc ctgtaaccaagaaagattaaatataaataatgcgatcacgcaggcgaaaacagatataccgccttaaaataggtagatgcgtttaa aaacaagatcagcatcaacataatcaaatagctcagtaataccgaacgggaggcactgatcacaatagctaacccataataaaa ataagagcatagccgattaacttaattttccagttgttttctctgatgatgtaaaaaaatcccaccgccaccgcaagagaaatcataatta cggactggtcattggtattaaagaaaaaacctttaaacgccttatcagttacggttaattcttcattacccgaaaccaactggaacccca ataaagcctcaataaaaagcccgccagcacaattaatgatattcccaacaaaaggtgcctaatccctgcttctccatcacccggtt aaacgtcaaaaagaataatgaaataaaaacatcacaattccgaagaaaaacaaatcaactaatttttctgtagaaaacgcatttaa taccgataaaaagccgaagaaaaacaacacgtacaccggaaactgtaatttaaaaaaatcagtttccatatcccttaaaaagggg ttattaccgctaagaaaaagaacaaaaaacacaacgcactatctaacctcggcactcctatttgtgtcgatagtgcgggagaaagtat caccagtcccaacgcaaagagtaatagcaacttaaaaatgctgataacattaatattcatatcaaataatattttgattaatttctcaattt ctttataagaacgctcgcgcagaaacttctcttttgccagcgataaattcacttgcgacattttgtctaaaaccgttctgtcttcggccaattt -continued

```
attcaacgtctcagccaactcccgataatctcccgccgtatattgaattccaccgcctttcgccagtagttttttccacttcaggatgtttctga cagcttacaatcggtaatgcgcaacagatataatcggatctagactccataggccgcttcctggctttgcttccagatgtatgctctcctc cggagagtaccgtgactttattttcggcacaaatacaggggtcgatggataaatacggcgatagtttcctgacgatgatccgtatgtac cggcggaagacaagctgcaaacctgtcagatggagattgatttaatggcggatgtgctgagagcaccgcccgtgaatccgcaga actgatccgctatgtgtttgcggatgattggccggaataaataaagccgggcttaatacagattaagcccgtatagggtattattactga ataccaaacagcttacggaggacggaatgttacccattgagacaaccagactgccttctgattattaatattttcactattaatcagaag gaataaccatgaattttacccggattgacctgaatacctggaatcgcagggaacactttgccctttatcgtcagcagattaaatgcggat tcagcctgaccaccaaactcgatattaccgctttgcgtaccgcactggcggagacaggttataagtttttatccgctgatgatttacctgat ctcccgggctgttaatcagtttccggagttccggatggcactgaaagacaatgaacttatttactgggaccagtcagacccggtctttact gtctttcataaagaaaccgaaacattctctgcactgtcctgccgttattttccggatctcagtgagtttatggcaggttataatgcggtaacg gcagaatatcagcatgataccagattgtttccgcagggaaatttaccggagaatcacctgaatatatcatcattaccgtgggtgagttttg acgggatttaacctgaacatcaccggaaatgatgattattttgccccggttttttacgatggcaaagtttcagcaggaaggtgaccgcgta ttattacctgtttctgtacaggttcatcatgcagtctgtgatggcttcatgcagcacggtttattaatacacttcagctgatgtgtgataacata ctgaaataaattaattaattctgtatttaagccaccgtatccggcaggaatggtggctttttttttatatttttaaccgtaatctgtaatttcgtttca gactggttcaggatgagctcgcttggactcctgttgatagatccagtaatgacctcagaactccatctggatttgttcagaacgctcggttg ccgccgggcgttttttattggtgagaatccaagcactagcggcgcgccggccggcccggtgtgaaataccgcacagatgcgtaagg agaaaataccgcatcaggcgctcttccgcttcctcgctcactgactcgctgcgctcggtcgttcggctgcggcgagcggtatcagctca ctcaaaggcggtaatacggttatccacagaatcaggggataacgcaggaaagaacatgtgagcaaaaggccagcaaaaggcca ggaaccgtaaaaaggccgcgttgctggcgtttttccataggctccgcccccctgacgagcatcacaaaaatcgacgctcaagtcaga ggtggcgaaacccgacaggactataaagataccaggcgtttccccctggaagctccctcgtgcgctctcctgttccgaccctgccgctt accggatacctgtccgcctttctcccttcgggaagcgtggcgctttctcatagctcacgctgtaggtatctcagttcggtgtaggtcgttcgc tccaagctgggctgtgtgcacgaaccccccgttcagcccgaccgctgcgccttatccggtaactatcgtcttgagtccaacccggtaag acacgacttatcgccactggcagcagccactggtaacaggattagcagagcgaggtatgtaggcggtgctacagagttcttgaagtg gtggcctaactacggctacactagaaggacagtatttggtatctgcgctctgctgaagccagttaccttcggaaaaagagttggtagct cttgatccggcaaacaaaccaccgctggtagcggtggtttttttgtttgcaagcagcagattacgcgcagaaaaaaaggatctcaaga agatcctttgatcttttctacggggtctgacgctcagtggaacgaaaactcacgttaagggattttggtcatgagattatcaaaaaggatct tcacctagatccttttaaaggccggccgcggccgccatcggcattttcttttgcgttttatttgttaactgttaattgtccttgttcaaggatgct gtctttgacaacagatgttttcttgcctttgatgttcagcaggaagctcggcgcaaacgttgattgtttgtctgcgtagaatcctctgtttgtcat atagcttgtaatcacgacattgtttcctttcgcttgaggtacagcgaagtgtgagtaagtaaaggttacatcgttaggatcaagatccatttt taacacaaggccagttttgttcagcggcttgtatgggccagttaaagaattagaaacataaccaagcatgtaaatatcgttagacgtaa tgccgtcaatcgtcattttttgatccgcggagtcagtgaacaggtaccatttgccgttcattttaaagacgttcgcgcgttcaatttcatctgtt actgtgttagatgcaatcagcggtttcatcacttttttcagtgtgtaatcatcgtttagctcaatcataccgagagcgccgtttgctaactcag ccgtgcgttttttatcgctttgcagaagttttgactttcttgacggaagaatgatgtgcttttgccatagtatgctttgttaaataaagattcttcg ccttggtagccatcttcagttccagtgtttgcttcaaatactaagtatttgtggcctttatcttctacgtagtgaggatctctcagcgtatggttgt cgcctgagctgtagttgccttcatcgatgaactgctgtacattttgatacgttttccgtcaccgtcaaagattgatttataatcctctacaccg ttgatgttcaaagagctgtctgatgctgatacgttaacttgtgcagttgtcagtgtttgtttgccgtaatgtttaccggagaaatcagtgtaga ataaacggattttccgtcagatgtaaatgtggctgaacctgaccattcttgtgtttggtcttttaggatagaatcatttgcatcgaatttgtcgc tgtctttaaagacgcggccagcgttttccagctgtcaatagaagtttcgccgactttttgatagaacatgtaaatcgatgtgtcatccgcat ttttaggatctccggctaatgcaaagacgatgtggtagccgtgatagtttgcgacagtgccgtcagcgttttgtaatggccagctgtccca aacgtccaggccttttgcagaagagatatttttaattgtggacgaatcaaattcagaaacttgatatttttcattttttttgctgttcagggatttg cagcatatcatggcgtgtaatatgggaaatgccgtatgtttccttatatggcttttggttcgtttctttcgcaaacgcttgagttgcgcctcctgc
```

-continued cagcagtgcggtagtaaaggttaatactgttgcttgttttgcaaactttttgatgttcatcgttcatgtctccttttttatgtactgtgttagcggtct gcttcttccagccctcctgtttgaagatggcaagttagttacgcacaataaaaaagacctaaaatatgtaaggggtgacgccaaagt atacactttgccctttacacatttttaggtcttgcctgctttatcagtaacaaacccgcgcgatttacttttcgacctcattctattagactctcgttt ggattgcaactggtctattttcctcttttgtttgatagaaaatcataaaaggatttgcagactacgggcctaaagaactaaaaaatctatct gtttcttttcattctctgtattttttatagtttctgttgcatgggcataaagttgccttttaatcacaattcagaaaatatcataatatctcatttcact aaaataatagtgaacggcaggtatatgtgatgggttaaaaaggatcggcggccgctcgatttaaatc SEQ ID NO: 22 (complete nucleotide sequence of plasmid pSacB_delta_ptsA)
tcgagtcgcaatgtcctattttagacatagcctccgtaagcgcatgggctaaattcataccgccgctgcgatcccgttgcaaaagatgat atgccatacgctgtgcggatttcggcccgacaccgggcaaacagcgtaaactttcgattaaattttctaataaaggactggtttgcataa gactctaaaaataacaaaaaacaaaccgcacttttaaaagtgcggtcttatttcataaaattttacttaaaacggcattttaaaacccgg aggaatcggcataccagcggtaactgacgccattttctcttttgtaactcatccgcgcggcgagcggcatcattaaatgcggcggcga tgagatcttccaacatatccttatcgtcttccattaatgaaggatcaatttccacgcgacggcaattatgcgcaccgttaattgttactttaac taaccccgcaccggactcaccggttacttcaagtgggcaatttcttcctgcatttttgcatacgctcttgcatttgctgagcttgtttcattaa attgcctaagccaccttttccaaacataattcttcttccatttttgagcgtataaaatatacgaataaattaaataaaaagtccgctctaaac aaagcgaactttctaacaattataatgagactaatcagcttttattttttagtgataaaaccactgaatcgccggcaacaacctggccta ctttttatccaacgcactaatttcatccatatttgaaattactaccggagtaagaatagatttcgcttttgttctaaaagtggtaaatcaaact caataatagtatcaccacgtttcacagactgaccctcttgtgcaacacgggtaaaaccttcacctttaagttcaacggtatcaataccga agtgaacaaataattcaataccttcttttgattccattgaaaatgcatgatttgtttcaaaaatcttgccaatcacgccgtccaccggtgcaa caattttgtcaccgttcggacgaatcgcaataccgtcgccaacgattttttcagaaaaaaccacatccggtacatcttcaatattaacaat ttcacctgaaagcggcgcataaatgtccacttctacggttttactatttttgaaccaaataatttatcaaataagcccatttttttaatctcctga atcgacaattttccgtattctacatgaaaaacatgaatttgtatctaatttaatgttttttcagctaaaaaatcagcaactaattttttcaatttcg gcagcagtcggtaattgcagggctttatccgctaatgcttttgcttcggcaaaattaacactacgaaccaattttttaatacgaggaacgg aaatagcgctcatgctgaattcgtctaatcccatacctaataataaaatagtggcttttttcatcaccggctaactcaccgcacataccagt ccatttgccttcggtatgagaggcgtcacgccgtacggccttcataaaaacgagctacttcagtttcaacttgatcttcagcaattttttgca tatcaagtacaattttttcctcttttcagaactaacgcttaccaaaaacgatacctggtgaggccgggattcctgaaatcatgtgtaaccttc cgataataatttaattaaaaaaatctaactatgataaacgacatagccataaaactcttttattaacagtgataaatcaataagaaagttttt atggccagacaaattattctaatgtaggaattaatgcaactaaatggtcaacagcatttgctcatcttcgccttcagctgaaattgtaatta cagttccttgagttaagcctaaagtttgtaatttgaataaactttttcgcacttgcacttttaccggcagaagtcactgttacatcagatgcaa acgcttttgcttcttttacaaattgtgcagccggacgagtgtgtaagccgttaggagctgtaatttcaacatcttttgaatacataattttacct ctaatagtaatgttttttgttttaatgtggagcaaacaggtaaacggttaacttttgacctgcctactaaaatttaattattcataaaccacag cggacactctaaaccattttgtctgatagttcaaaataaatcttatttagtatcaagattattcctaattaattcaagttaaatcctataaaaac ttgagctagttcatcttttttgtcaaccgatagattaattttttaataaaaatgtaacaaattagtaataaaaaataaccgaattaccttatatcct gctccataaaatggcgttgcgatttatttttcttcccggcttgaaatcaagcgatggtaattatcaaatctgacggggtggattttcccgagct ccacagcttcccgtaaggcgcagcccggatcatcaatatgtttgcagtctctgaatttgcaggtccctaagaaatattggaattcccgat aaccgttggtgatttgtgcaggttccaaatgccataaaccgaactctcgaatgcccggcgaatcaatcagatttccgccctgaggtaaa tgatataaacggggaagacgtggtggtatgctgtcccaatcccgaagtttcgctgatttcaccggtttgcgcattaacttccggtaaaatat agttgattaaactggcttccctaccccggattgcccgacgaaaatcgacgtaccatccgctaaaagtgcggtcagttttttccatattttt ccactaatcgccgaaatcattaatgtttcatagccgattttcggtagatttccagttgttcttccgcttccgccactgttcgtccgttaataaa tcaaccttattcaacaagataacggcaggaatattagcgttttcacaaataaccaaataacgatcaataatattcagggataacgccg gtagcaccgacgaaacaataataatgcgatcgatattcgatgccattctagactccataggccgctttcctggctttgcttccagatgtat gctctcctccggagagtaccgtgactttatttttcggcacaaatacaggggtcgatggataaatacggcgatagtttcctgacggatgatc -continued

```
cgtatgtaccggcggaagacaagctgcaaacctgtcagatggagattgatttaatggcggatgtgctgagagcaccgccccgtgaat
ccgcagaactgatccgctatgtgtttgcggatgattggccggaataaataaagccgggcttaatacagattaagcccgtatagggtatt
attactgaataccaaacagcttacggaggacggaatgttacccattgagacaaccagactgccttctgattattaatattttttcactattaa
tcagaaggaataaccatgaattttacccggattgacctgaatacctggaatcgcagggaacactttgcccttttatcgtcagcagattaa
atgcggattcagcctgaccaccaaactcgatattaccgctttgcgtaccgcactggcggagacaggttataagttttatccgctgatgatt
tacctgatctcccgggctgttaatcagtttccggagttccggatggcactgaaagacaatgaacttatttactgggaccagtcagacccg
gtctttactgtctttcataaagaaaccgaaacattctctgcactgtcctgccgttattttccggatctcagtgagtttatggcaggttataatgc
ggtaacggcagaatatcagcatgataccagattgtttccgcagggaaatttaccggagaatcacctgaatatatcatcattaccgtggg
tgagttttgacgggatttaacctgaacatcaccggaaatgatgattattttgccccggttttttacgatggcaaagtttcagcaggaaggtg
accgcgtattattacctgtttctgtacaggttcatcatgcagtctgtgatgctttcatgcagcacggtttattaatacacttcagctgatgtgt
gataacatactgaaataaattaattaattctgtatttaagccaccgtatccggcaggaatggtggctttttttttatattttaaccgtaatctgta
atttcgtttcagactggttcaggatgagctcgcttggactcctgttgatagatccagtaatgacctcagaactccatctggatttgttcagaa
cgctcggttgccgccgggcgttttttattggtgagaatccaagcactagcggcgcgccggccggccggtgtgaaataccgcacagat
gcgtaaggagaaaataccgcatcaggcgctcttccgcttcctcgctcactgactcgctgcgctcggtcgttcggctgcggcgagcggt
atcagctcactcaaaggcggtaatacggttatccacagaatcaggggataacgcaggaaagaacatgtgagcaaaaggccagca
aaaggccaggaaccgtaaaaaggccgcgttgctggcgttttttccataggctccgcccccctgacgagcatcacaaaaatcgacgct
caagtcagaggtggcgaaacccgacaggactataaagataccaggcgtttccccctggaagctccctcgtgcgctctcctgttccga
ccctgccgcttaccggatacctgtccgcctttctcccttcgggaagcgtggcgctttctcatagctcacgctgtaggtatctcagttcggtgt
aggtcgttcgctccaagctgggctgtgtgcacgaaccccccgttcagcccgaccgctgcgccttatccggtaactatcgtcttgagtcca
acccggtaagacacgacttatcgccactggcagcagccactggtaacaggattagcagagcgaggtatgtaggcggtgctacaga
gttcttgaagtggtggcctaactacggctacactagaaggacagtatttggtatctgcgctctgctgaagccagttaccttcggaaaaag
agttggtagctcttgatccggcaaacaaaccaccgctggtagcggtggtttttttgtttgcaagcagcagattacgcgcagaaaaaaag
gatctcaagaagatcctttgatcttttctacggggtctgacgctcagtggaacgaaaactcacgttaagggattttggtcatgagattatca
aaaaggatcttcacctagatcctttaaaggccggccgcggccgccatcggcatttttcttttgcgttttatttgttaactgttaattgtccttgtt
caaggatgctgtctttgacaacagatgttttcttgcctttgatgttcagcaggaagctcggcgcaaacgttgattgtttgtctgcgtagaatc
ctctgtttgtcatatagcttgtaatcacgacattgtttccttcgcttgaggtacagcgaagtgtgagtaagtaaaggttacatcgttaggatc
aagatccatttttaacacaaggccagttttgttcagcggcttgtatgggccagttaaagaattagaaacataaccaagcatgtaaatatc
gttagacgtaatgccgtcaatcgtcattttgatccgcgggagtcagtgaacaggtaccatttgccgttcattttaaagacgttcgcgcgttc
aatttcatctgttactgtgttagatgcaatcagcggtttcatcacttttttcagtgtgtaatcatcgtttagctcaatcataccgagagcgccgtt
tgctaactcagccgtgcgttttttatcgctttgcagaagttttgactttcttgacggaagaatgatgtgcttttgccatagtatgctttgttaaata
aagattcttcgccttggtagccatcttcagttccagtgtttgcttcaaatactaagtatttgtgccctttatcttctacgtagtgaggatctctcag
cgtatggttgtcgcctgagctgtagttgccttcatcgatgaactgctgtacattttgatacgttttccgtcaccgtcaaagattgatttataatc
ctctacaccgttgatgttcaaagagctgtctgatgctgatacgttaacttgtgcagttgtcagtgtttgtttgccgtaatgtttaccggagaaat
cagtgtagaataaacggattttccgtcagatgtaaatgtggctgaacctgaccattcttgtgtttggtcttttaggatagaatcatttgcatc
gaatttgtcgctgtctttaaagacgcggcagcgttttttccagctgtcaatagaagtttcgccgacttttttgatagaacatgtaaatcgatgt
gtcatccgcatttttaggatctccggctaatgcaaagacgatgtggtagccgtgatagtttgcgacagtgccgtcagcgttttgtaatggc
cagctgtcccaaacgtccaggccttttgcagaagagatattttaattgtggacgaatcaaattcagaaacttgatattttttcatttttttgctgt
tcagggatttgcagcatatcatggcgtgtaatatgggaaatgccgtatgtttccttatatggcttttggttcgtttctttcgcaaacgcttgagtt
gcgcctcctgccagcagtgcggtagtaaaggttaatactgttgcttgttttgcaaacttttttgatgttcatcgttcatgtctccttttttatgtactg
tgttagcggtctgcttcttccagccctcctgtttgaagatggcaagttagttacgcacaataaaaaaagacctaaaatatgtaaggggtg
```

-continued acgccaaagtatacactttgcccttttacacatttttaggtcttgcctgctttatcagtaacaaacccgcgcgatttacttttcgacctcattctatt agactctcgtttggattgcaactggtctattttcctcttttgtttgatagaaaatcataaaaggatttgcagactacgggcctaaagaactaa aaaatctatctgtttcttttcattctctgtattttttatagtttctgttgcatgggcataaagttgccttttttaatcacaattcagaaaatatcataata tctcatttcactaaataatagtgaacggcaggtatatgtgatgggttaaaaaggatcggcggccgctcgatttaaatc SEQ ID NO: 23 (complete nucleotide sequence of plasmid pSacB_delta_ptsH)
tcgagccgatactgaagaagtccacttcttttgctaagaattttgcatttactgcagctgacggcgtttcacacattacaccgatttgaatatt ttcatcaaaggctttaccttcggtgcgtaattcttgttttaaagtttcgataacggatttcaattcgcgaatttcttcaacggaaataatcatcg ggaacattaccgctaatttaccgaatgcggaagcacgtaataccgcacgcaattgagcatttaagatttcgcgacgatccaatgcgat acgaaccgcacgccagcctaagaacggattcatttcttttggcagattcatataaggtaattctttatctccaccaatatccatggtacgta ataccacctggcgaccgttcatcgcttctaccacttctttataagcgataaattgttcttcttctgaaggcagttggtcacgatccatgaaca ggaactcggtacggtataaaccgacaccttccgcaccgttacgatccgcaccctcacagtcacgaatcgtaccgatattcgccacca cttcaacacggtgaccgtccaatgttactgccggtaaatcttttaatttagctaattccgcttttcttccgctaattttgcttgttgggcttttaag ccgtcaatcacgtcttgagccggattcacataaacagcgttattgattgcatcaagtactaaataatcaccgctgttaatcattgcggttgc attatttgtacctacaattgccggtaattccagcgaacgggccataatagaggtatgtgaagtacgaccaccgatatcagtaataaaac ctaatactttgtctaaattcaattgtgcggtttctgatggcgttaagtcataagcaaccaagattgactcttcattgatttcgcccaaatccac aattttcatgcctaagatatttttaattaaacggttaccgatatcgcgaatatcgccggcacgttcttttaagtactcatcatcaatatccgca agcatagcaacttgttgatcaatgatttttacttgccgcaacgcccgcatttactttgtttgaacgcaaataatcaatgatttcttcttccaactc ttcatcttcaagaatcattaaatgaccttcgaagatagccgctttttcttcaccgagagttttctctgcacgatctctaatggcgcttaattgttc cactgccgccgtacggccttcataaaaacgagctacttcagtttcaacttgatcttcagcaatttttttgcatatcaagtacaattttttcctctttt cagaactaacgctttaccaaaaacgatacctggtgaggccgggattcctgaaatcatgtgtaaccttccgataataatttaattaaaaa aatctaactatgataaacgacatagccataaaactcttttattaacagtgataaatcaataagaaagttttatggccagacaaattattct aatgtaggaattaatgcaactaaatggtcaacagcattttgctcatcttcgccttcaacctctaatagtaatgttttttgttttaatgtggagca aacaggtaaacggttaacttttgacctgcctactaaaatttaattattcataaaccacagcggacactctaaaccattttgtctgatagttc aaaataaatcttatttagtatcaagattattcctaattaattcaagttaaatcctataaaaacttgagctagttcatcttttttgtcaaccgatag attaattttaataaaaatgtaacaaattagtaataaaaaataaccgaattaccttatatcctgctccataaaatggcgttgcgatttattttct tcccggcttgaaatcaagcgatggtaattatcaaatctgacggggtggattttcccgagctccacagcttcccgtaaggcgcagcccg gatcatcaatatgtttgcagtctctgaatttgcaggtccctaagaaatattggaattcccgataaccgttggtgatttgtgcaggttccaaat gccataaaccgaactctcgaatgcccggcgaatcaatcagatttccgccctgaggtaaatgatataaacgggaagacgtggtggtat gctgtcccaatcccgaagtttcgctgatttcaccggtttgcgcattaacttccggtaaaatatagttgattaaactggacttccctaccccgg attgcccgacgaaaatcgacgtaccatccgctaaaagtgcggtcagttttttccatatttttttccactaatcgccgaaatcattaatgtttcat agccgatttttcggtagatttccagttgttcttccgcttcccgccactgttcgtccgttaataaatcaaccttattcaacaagataacggcag gaatattagcgttttcacaaataaccaaataacgatcaataatattcagggataacgccggtagcaccgacgaaacaataataatgc gatcgatattcgatgccatgactttcagtccgtcataataatccgggcgggcaatttcattttcacgcggtttaatcgcctcaatgaccccg ctaatacccctgtagtttttcatgccctcggcgccacactacgtgatctcccaccaccacattggctaatgtgcgacgtaaattacaacgg aaaatctcgccttgactattctccacatccgcatgcatagaataacgagtgacgacaacgccgtcttgcgtatcgccaagcatttcttcct gccaatcaatctctttttttactcttcggtgatgacgatccaatgcttttacattatttgaatgaattcgacgttttttgattttgagttaatttacgctt agtcaaacagaagtccttaaagtgcggtagattttcgtataatattacgggtcaacaaatcagttaacgtataaatgcttataggatactc caaattatgcaattagataaccaaaatctaatctggatcgacttagaaatgacccgggttagaccctgaaaacagagccgcattattgaaat cgccaccatctagactccataggccgctttcctggctttgcttccagatgtatgctctcctccggagagtaccgtgactttattttcggcaca aatacagggtcgatggataaatacgcgatagtttcctgacggatgatccgtatgtaccggcggaagacaagctgcaaacctgtca gatggagattgatttaatggcggatgtgctgagagcaccgccccgtgaatccgcagaactgatccgctatgtgtttgcggatgattggc -continued

```
cggaataaataaagccgggcttaatacagattaagcccgtatagggtattattactgaataccaaacagcttacggaggacggaatg ttacccattgagacaaccagactgccttctgattattaatattttttcactattaatcagaaggaataaccatgaattttacccggattgacct gaatacctggaatcgcagggaacactttgccctttatcgtcagcagattaaatgcggattcagcctgaccaccaaactcgatattaccg ctttgcgtaccgcactggcggagacaggttataagttttatccgctgatgatttacctgatctcccgggctgttaatcagtttccggagttcc ggatggcactgaaagacaatgaacttatttactgggaccagtcagacccggtctttactgtctttcataaagaaaccgaaacattctctg cactgtcctgccgttattttccggatctcagtgagtttatggcaggttataatgcggtaacggcagaatatcagcatgataccagattgtttc cgcagggaaatttaccggagaatcacctgaatatatcatcattaccgtgggtgagttttgacgggatttaacctgaacatcaccggaaa tgatgattattttgccccggttttacgatggcaaagtttcagcaggaaggtgaccgcgtattattacctgtttctgtacaggttcatcatgca gtctgtgatggctttcatgcagcacggtttattaatacacttcagctgatgtgtgataacatactgaaataaattaattaattctgtatttaagc caccgtatccggcaggaatggtggcttttttttttatattttaaccgtaatctgtaatttcgtttcagactggttcaggatgagctcgcttggactc ctgttgatagatccagtaatgacctcagaactccatctggatttgttcagaacgctcggttgccgccgggcgttttttattggtgagaatcca agcactagcggcgcgccggccggcccggtgtgaaataccgcacagatgcgtaaggagaaaataccgcatcaggcgctcttccgct tcctcgctcactgactcgctgcgctcggtcgttcggctgcggcgagcggtatcagctcactcaaaggcggtaatacggttatccacaga atcaggggataacgcaggaaagaacatgtgagcaaaaggccagcaaaaggccaggaaccgtaaaaaggccgcgttgctggcg tttttccataggctccgcccccctgacgagcatcacaaaaatcgacgctcaagtcagaggtggcgaaacccgacaggactataaag ataccaggcgtttccccctggaagctccctcgtgcgctctcctgttccgaccctgccgcttaccggatacctgtccgcctttctcccttcgg gaagcgtggcgctttctcatagctcacgctgtaggtatctcagttcggtgtaggtcgttcgctccaagctgggctgtgtgcacgaacccccc gttcagcccgaccgctgcgccttatccggtaactatcgtcttgagtccaacccggtaagacacgacttatcgccactggcagcagcc actggtaacaggattagcagagcgaggtatgtaggcggtgctacagagttcttgaagtggtggcctaactacggctacactagaagg acagtatttggtatctgcgctctgctgaagccagttaccttcggaaaaagagttggtagctcttgatccggcaaacaaaccaccgctggt agcggtggtttttttgtttgcaagcagcagattacgcgcagaaaaaaaggatctcaagaagatcctttgatcttttctacggggtctgacg ctcagtggaacgaaaactcacgttaagggattttggtcatgagattatcaaaaaggatcttcacctagatccttttaaaggccggccgc ggccgccatcggcattttcttttgcgttttatttgttaactgttaattgtccttgttcaaggatgctgtctttgacaacagatgttttcttgcctttgat gttcagcaggaagctcggcgcaaacgttgattgtttgtctgcgtagaatcctctgtttgtcatatagcttgtaatcacgacattgtttcctttcg cttgaggtacagcgaagtgtgagtaagtaaaggttacatcgttaggatcaagatccattttttaacacaaggccagttttgttcagcggctt gtatgggccagttaaagaattagaaacataaccaagcatgtaaatatcgttagacgtaatgccgtcaatcgtcattttgatccgcggga gtcagtgaacaggtaccatttgccgttcattttaaagacgttcgcgcgttcaatttcatctgttactgtgttagatgcaatcagcggtttcatc actttttttcagtgtgtaatcatcgtttagctcaatcataccgagagcgccgtttgctaactcagccgtgcgttttttatcgctttgcagaagttttt gactttcttgacggaagaatgatgtgcttttgccatagtatgctttgttaaataaagattcttcgccttggtagccatcttcagttccagtgtttg cttcaaatactaagtatttgtggcctttatcttctacgtagtgaggatctctcagcgtatggttgtcgcctgagctgtagttgccttcatcgatg aactgctgtacattttgatacgttttttccgtcaccgtcaaagattgatttataatcctctacaccgttgatgttcaaagagctgtctgatgctga tacgttaacttgtgcagttgtcagtgtttgtttgccgtaatgtttaccggagaaatcagtgtagaataaacggattttccgtcagatgtaaat gtggctgaacctgaccattcttgtgtttggtcttttaggatagaatcatttgcatcgaatttgtcgctgtctttaaagacgcggccagcgttttc cagctgtcaatagaagtttcgccgacttttgatagaacatgtaaatcgatgtgtcatccgcatttttaggatctccggctaatgcaaagac gatgtggtagccgtgatagtttgcgacagtgccgtcagcgttttgtaatggccagctgtcccaaacgtccaggccttttgcagaagagat atttttaattgtggacgaatcaaattcagaaacttgatatttttcatttttttgctgttcagggatttgcagcatatcatggcgtgtaatatgggaa atgccgtatgtttccttatatggcttttggttcgtttctttcgcaaacgcttgagttgcgcctcctgccagcagtgcggtagtaaaggttaatact gttgcttgttttgcaaacttttttgatgttcatcgttcatgtctccttttttatgtactgtgttagcggtctgcttcttccagccctcctgtttgaagatgg caagttagttacgcacaataaaaaaagacctaaaatgtgaagggggtgacgccaaagtatacactttgccctttacacattttaggtctt
```

-continued gcctgctttatcagtaacaaacccgcgcgatttacttttcgacctcattctattagactctcgtttggattgcaactggtctattttcctcttttgttt gatagaaaatcataaaaggatttgcagactacgggcctaaagaactaaaaaatctatctgtttcttttcattctctgtatttttttatagtttctgt tgcatgggcataaagttgccttttaatcacaattcagaaaatatcataatatctcatttcactaaataatagtgaacggcaggtatatgtg atgggttaaaaaggatcggcggccgctcgatttaaatc

SEQUENCE LISTING

<160> NUMBER OF SEQ ID NOS: 23

<210> SEQ ID NO 1
<211> LENGTH: 1517
<212> TYPE: DNA
<213> ORGANISM: Basfia succiniciproducens
<220> FEATURE:
<221> NAME/KEY: misc_feature
<222> LOCATION: (1)..(1517)
<223> OTHER INFORMATION: 16 S rDNA of strain DD1

<400> SEQUENCE: 1

```
tttgatcctg gctcagattg aacgctggcg gcaggcttaa cacatgcaag tcgaacggta      60
gcgggaggaa agcttgcttt ctttgccgac gagtggcgga cgggtgagta atgcttgggg     120
atctggctta tggaggggga taacgacggg aaactgtcgc taataccgcg taatatcttc     180
ggattaaagg gtgggacttt cgggccaccc gccataagat gagcccaagt gggattaggt     240
agttggtggg gtaaaggcct accaagccga cgatctctag ctggtctgag aggatgacca     300
gccacactgg aactgagaca cggtccagac tcctacggga ggcagcagtg gggaatattg     360
cacaatgggg ggaaccctga tgcagccatg ccgcgtgaat gaagaaggcc ttcgggttgt     420
aaagttcttt cggtgacgag gaaggtgttt gttttaatag gacaagcaat tgacgttaat     480
cacagaagaa gcaccggcta actccgtgcc agcagccgcg gtaatacgga gggtgcgagc     540
gttaatcgga taactgggc gtaaagggca tgcaggcgga cttttaagtg agatgtgaaa     600
gccccgggct taacctggga attgcatttc agactgggag tctagagtac tttagggagg     660
ggtagaattc cacgtgtagc ggtgaaatgc gtagagatgt ggaggaatac cgaaggcgaa     720
ggcagcccct tgggaagata ctgacgctca tatgcgaaag cgtggggagc aaacaggatt     780
agataccctg gtagtccacg cggtaaacgc tgtcgatttg gggattgggc tttaggcctg     840
gtgctcgtag ctaacgtgat aaatcgaccg cctggggagt acggccgcaa ggttaaaact     900
caaatgaatt gacgggggcc cgcacaagcg gtggagcatg tggtttaatt cgatgcaacg     960
cgaagaacct tacctactct tgacatccag agaatcctgt agagatacgg gagtgccttc    1020
gggagctctg agacaggtgc tgcatggctg tcgtcagctc gtgttgtgaa atgttgggtt    1080
aagtcccgca acgagcgcaa cccttatcct tgttgccag catgtaaaga tgggaactca     1140
aaggagactg ccggtgacaa accggaggaa ggtgggggatg acgtcaagtc atcatggccc    1200
ttacgagtag ggctacacac gtgctacaat ggtgcataca gagggcggcg ataccgcgag    1260
gtagagcgaa tctcagaaag tgcatcgtag tccggattgg agtctgcaac tcgactccat    1320
gaagtcggaa tcgctagtaa tcgcaaatca gaatgttgcg gtgaatacgt tcccgggcct    1380
tgtacacacc gcccgtcaca ccatgggagt gggttgtacc agaagtagat agcttaacct    1440
tcggggggg cgtttaccac ggtatgattc atgactgggg tgaagtcgta acaaggtaac    1500
cgtaggggaa cctgcgg                                                   1517
```

<210> SEQ ID NO 2

<211> LENGTH: 3008
<212> TYPE: DNA
<213> ORGANISM: Basfia succiniciproducens
<220> FEATURE:
<221> NAME/KEY: misc_feature
<222> LOCATION: (1)..(3008)
<223> OTHER INFORMATION: 23 S rDNA of strain DD1

<400> SEQUENCE: 2

| | | | | | |
|---|---|---|---|---|---|
| agtaataacg | aacgacacag | gtataagaat | acttgaggtt | gtatggttaa | gtgactaagc | 60 |
| gtacaaggtg | gatgccttgg | caatcagagg | cgaagaagga | cgtgctaatc | tgcgaaaagc | 120 |
| ttgggtgagt | tgataagaag | cgtctaaccc | aagatatccg | aatggggcaa | cccagtagat | 180 |
| gaagaatcta | ctatcaataa | ccgaatccat | aggttattga | ggcaaaccgg | gagaactgaa | 240 |
| acatctaagt | accccgagga | aaagaaatca | accgagatta | cgtcagtagc | ggcgagcgaa | 300 |
| agcgtaagag | ccggcaagtg | atagcatgag | gattagagga | atcggctggg | aagccgggcg | 360 |
| gcacagggtg | atagccccgt | acttgaaaat | cattgtgtgg | tactgagctt | gcgagaagta | 420 |
| gggcgggaca | cgagaaatcc | tgtttgaaga | agggggacc | atcctccaag | gctaaatact | 480 |
| cctgattgac | cgatagtgaa | ccagtactgt | gaaggaaagg | cgaaaagaac | cccggtgagg | 540 |
| ggagtgaaat | agaacctgaa | accttgtacg | tacaagcagt | gggagcccgc | gagggtgact | 600 |
| gcgtaccttt | tgtataatgg | gtcagcgact | tatattatgt | agcgaggtta | accgaatagg | 660 |
| ggagccgaag | ggaaaccgag | tcttaactgg | gcgtcgagtt | gcatgatata | gacccgaaac | 720 |
| ccggtgatct | agccatgggc | aggttgaagg | ttgggtaaca | ctaactggag | gaccgaaccg | 780 |
| actaatgttg | aaaaattagc | ggatgacctg | tggctggggg | tgaaaggcca | atcaaaccgg | 840 |
| gagatagctg | gttctccccg | aaatctattt | aggtagagcc | ttatgtgaat | accttcgggg | 900 |
| gtagagcact | gtttcggcta | gggggccatc | ccggcttacc | aacccgatgc | aaactgcgaa | 960 |
| taccgaagag | taatgcatag | gagacacacg | gcgggtgcta | acgttcgtcg | tggagaggga | 1020 |
| aacaacccag | accgccagct | aaggtcccaa | agtttatatt | aagtgggaaa | cgaagtggga | 1080 |
| aggcttagac | agctaggatg | ttggcttaga | agcagccatc | atttaaagaa | agcgtaatag | 1140 |
| ctcactagtc | gagtcggcct | gcgcggaaga | tgtaacgggg | ctcaaatata | gcaccgaagc | 1200 |
| tgccggcatca | ggcgtaagcc | tgttgggtag | gggagcgtcg | tgtaagcgga | agaaggtggt | 1260 |
| tcgagagggc | tgctggacgt | atcacgagtg | cgaatgctga | cataagtaac | gataaaacgg | 1320 |
| gtgaaaaacc | cgttcgccgg | aagaccaagg | gttcctgtcc | aacgttaatc | ggggcagggt | 1380 |
| gagtcggccc | ctaaggcgag | gctgaagagc | gtagtcgatg | ggaaacgggt | taatattccc | 1440 |
| gtacttgtta | taattgcgat | gtggggacgg | agtaggttag | gttatcgacc | tgttggaaaa | 1500 |
| ggtcgtttaa | gttggtaggt | ggagcgttta | ggcaaatccg | gacgcttatc | aacaccgaga | 1560 |
| gatgatgacg | aggcgctaag | gtgccgaagt | aaccgatacc | acacttccag | gaaaagccac | 1620 |
| taagcgtcag | attataataa | accgtactat | aaaccgacac | aggtggtcag | gtagagaata | 1680 |
| ctcaggcgct | tgagagaact | cggggtgaagg | aactaggcaa | aatagcaccg | taacttcggg | 1740 |
| agaaggtgcg | ccggcgtaga | ttgtagaggt | ataccttga | aggttgaacc | ggtcgaagtg | 1800 |
| acccgctggc | tgcaactgtt | tattaaaaac | acagcactct | gcaaacacga | aagtggacgt | 1860 |
| atagggtgtg | atgcctgccc | ggtgctggaa | ggttaattga | tggcgttatc | gcaagagaag | 1920 |
| cgcctgatcg | aagccccagt | aaacggcggc | cgtaactata | acggtcctaa | ggtagcgaaa | 1980 |
| ttccttgtcg | ggtaagttcc | gacctgcacg | aatggcataa | tgatggccag | gctgtctcca | 2040 |
| cccgagactc | agtgaaattg | aaatcgccgt | gaagatgcgg | tgtacccgcg | gctagacgga | 2100 |

-continued

```
aagaccccgt gaacctttac tatagcttga cactgaacct tgaattttga tgtgtaggat    2160
aggtgggagg ctttgaagcg gtaacgccag ttatcgtgga gccatccttg aaataccacc    2220
ctttaacgtt tgatgttcta acgaagtgcc cggaacgggt actcggacag tgtctggtgg    2280
gtagtttgac tggggcggtc tcctcccaaa gagtaacgga ggagcacgaa ggtttgctaa    2340
tgacggtcgg acatcgtcag gttagtgcaa tggtataagc aagcttaact gcgagacgga    2400
caagtcgagc aggtgcgaaa gcaggtcata gtgatccggt ggtctgaat ggaagggcca     2460 tcgctcaacg gataaaaggt actccgggga taacaggctg ataccgccca agagttcata    2520 tcgacggcg tgtttggcac ctcgatgtcg gctcatcaca tcctggggct gaagtaggtc     2580
ccaagggtat ggctgttcgc catttaaagt ggtacgcgag ctgggtttaa aacgtcgtga    2640
gacagtttgg tccctatctg ccgtgggcgt tggagaattg agaggggctg ctcctagtac    2700
gagaggaccg gagtggacgc atcactggtg ttccggttgt gtcgccagac gcattgccgg    2760
gtagctacat gcggaagaga taagtgctga aagcatctaa gcacgaaact gcctcgaga     2820 tgagttctcc cagtatttaa tactgtaagg gttgttggag acgacgacgt agataggccg    2880
ggtgtgtaag cgttgcgaga cgttgagcta accggtacta attgcccgag aggcttagcc    2940
atacaacgct caagtgtttt tggtagtgaa agttattacg gaataagtaa gtagtcaggg    3000
aatcggct                                                             3008
```

<210> SEQ ID NO 3
<211> LENGTH: 1728
<212> TYPE: DNA
<213> ORGANISM: Basfia succiniciproducens
<220> FEATURE:
<221> NAME/KEY: misc_feature
<222> LOCATION: (1)..(1728)
<223> OTHER INFORMATION: nucleotide sequence of ptsA-gene from strain
      DD1

<400> SEQUENCE: 3

```
atgatttcag gaatcccggc ctcaccaggt atcgttttg gtaaagcgtt agttctgaaa       60
gaggaaaaaa ttgtacttga tatgcaaaaa attgctgaag atcaagttga aactgaagta     120
gctcgttttt atgaaggccg tacggcggca gtggaacaat aagcgccat tagagatcgt      180 gcagagaaaa ctctcggtga agaaaaagcg gctatcttcg aaggtcattt aatgattctt     240
gaagatgaag agttggaaga agaaatcatt gattatttgc gttcaaacaa agtaaatgcg    300
ggcgttgcgg caagtaaaat cattgatcaa caagttgcta tgcttgcgga tattgatgat    360
gagtacttaa agaacgtgc cggcgatatt cgcgatatcg gtaaccgttt aattaaaaat    420
atcttaggca tgaaaattgt ggatttgggc gaaatcaatg aagagtcaat cttggttgct    480
tatgacttaa cgccatcaga aaccgcacaa ttgaatttag acaaagtatt aggttttatt    540
actgatatcg gtggtcgtac ttcacatacc tctattatgg cccgttcgct ggaattaccg    600
gcaattgtag gtacaaataa tgcaaccgca atgattaaca gcggtgatta tttagtactt    660
gatgcaatca ataacgctgt ttatgtgaat ccggctcaag acgtgattga cggcttaaaa    720
gcccaacaag caaattagc ggaagaaaaa gcggaattag ctaaattaaa agatttaccg    780
gcagtaacat ggacggtca ccgtgttgaa gtggtggcga atatcggtac gattcgtgac    840
tgtgagggtg cggatcgtaa cggtgcggaa ggtgtcggtt tataccgtac cgagttcctg    900
ttcatggatc gtgaccaact gccttcagaa gaagaacaat ttatcgctta taagaagtg    960 gtagaagcga tgaacggtcg ccaggtggta ttacgtacca tggatattgg tggagataaa   1020
```

```
gaattacctt atatgaatct gccaaaagaa atgaatccgt tcttaggctg gcgtgcggtt    1080
cgtatcgcat tggatcgtcg cgaaatctta aatgctcaat tgcgtgcggt attacgtgct    1140
tccgcattcg gtaaattagc ggtaatgttc ccgatgatta tttccgttga agaaattcgc    1200
gaattgaaat ccgttatcga aactttaaaa caagaattac gcaccgaagg taaagccttt    1260
gatgaaaata ttcaaatcgg tgtaatgtgt gaaacgccgt cagctgcagt aaatgcaaaa    1320
ttcttagcaa aagaagtgga cttcttcagt atcggtacta atgatttaac tcaatatact    1380
ttagcggttg accgtggtaa tgaaatgatt tcacatttat ataatccaat gtcaccttca    1440
gtattaagtt taattaaaca ggttattgac gcctctcata ccgaaggcaa atggactggt    1500
atgtgcggtg agttagccgg tgatgaaaaa gccactattt tattattagg tatgggatta    1560
gacgaattca gcatgagcgc tatttccgtt cctcgtatta aaaaattggt tcgtagtgtt    1620
aattttgccg aagcaaaagc attagcggat aaagccctgc aattaccgac tgctgccgaa    1680
attgaaaaat tagttgctga tttttttagct gaaaaaacat taaattag                1728
```

```
<210> SEQ ID NO 4
<211> LENGTH: 575
<212> TYPE: PRT
<213> ORGANISM: Basfia succinicproducens
<220> FEATURE:
<221> NAME/KEY: SITE
<222> LOCATION: (1)..(575)
<223> OTHER INFORMATION: amino acid sequence of the enzyme encoded by
      the above ptsA-gene

<400> SEQUENCE: 4

Met Ile Ser Gly Ile Pro Ala Ser Pro Gly Ile Val Phe Gly Lys Ala
1               5                   10                  15

Leu Val Leu Lys Glu Glu Lys Ile Val Leu Asp Met Gln Lys Ile Ala
            20                  25                  30

Glu Asp Gln Val Glu Thr Glu Val Ala Arg Phe Tyr Glu Gly Arg Thr
        35                  40                  45

Ala Ala Val Glu Gln Leu Ser Ala Ile Arg Asp Arg Ala Glu Lys Thr
    50                  55                  60

Leu Gly Glu Glu Lys Ala Ala Ile Phe Glu Gly His Leu Met Ile Leu
65                  70                  75                  80

Glu Asp Glu Glu Leu Glu Glu Glu Ile Ile Asp Tyr Leu Arg Ser Asn
                85                  90                  95

Lys Val Asn Ala Gly Val Ala Ala Ser Lys Ile Ile Asp Gln Gln Val
            100                 105                 110

Ala Met Leu Ala Asp Ile Asp Asp Glu Tyr Leu Lys Glu Arg Ala Gly
        115                 120                 125

Asp Ile Arg Asp Ile Gly Asn Arg Leu Ile Lys Asn Ile Leu Gly Met
    130                 135                 140

Lys Ile Val Asp Leu Gly Glu Ile Asn Glu Glu Ser Ile Leu Val Ala
145                 150                 155                 160

Tyr Asp Leu Thr Pro Ser Glu Thr Ala Gln Leu Asn Leu Asp Lys Val
                165                 170                 175

Leu Gly Phe Ile Thr Asp Ile Gly Gly Arg Thr Ser His Thr Ser Ile
            180                 185                 190

Met Ala Arg Ser Leu Glu Leu Pro Ala Ile Val Gly Thr Asn Asn Ala
        195                 200                 205

Thr Ala Met Ile Asn Ser Gly Asp Tyr Leu Val Leu Asp Ala Ile Asn
    210                 215                 220
```

Asn Ala Val Tyr Val Asn Pro Ala Gln Asp Val Ile Asp Gly Leu Lys
225                 230                 235                 240

Ala Gln Gln Ala Lys Leu Ala Glu Glu Lys Ala Glu Leu Ala Lys Leu
            245                 250                 255

Lys Asp Leu Pro Ala Val Thr Leu Asp Gly His Arg Val Glu Val Val
        260                 265                 270

Ala Asn Ile Gly Thr Ile Arg Asp Cys Glu Gly Ala Asp Arg Asn Gly
    275                 280                 285

Ala Glu Gly Val Gly Leu Tyr Arg Thr Glu Phe Leu Phe Met Asp Arg
290                 295                 300

Asp Gln Leu Pro Ser Glu Glu Gln Phe Ile Ala Tyr Lys Glu Val
305                 310                 315                 320

Val Glu Ala Met Asn Gly Arg Gln Val Val Leu Arg Thr Met Asp Ile
                325                 330                 335

Gly Gly Asp Lys Glu Leu Pro Tyr Met Asn Leu Pro Lys Glu Met Asn
                340                 345                 350

Pro Phe Leu Gly Trp Arg Ala Val Arg Ile Ala Leu Asp Arg Arg Glu
            355                 360                 365

Ile Leu Asn Ala Gln Leu Arg Ala Val Leu Arg Ala Ser Ala Phe Gly
370                 375                 380

Lys Leu Ala Val Met Phe Pro Met Ile Ile Ser Val Glu Glu Ile Arg
385                 390                 395                 400

Glu Leu Lys Ser Val Ile Glu Thr Leu Lys Gln Glu Leu Arg Thr Glu
                405                 410                 415

Gly Lys Ala Phe Asp Glu Asn Ile Gln Ile Gly Val Met Cys Glu Thr
            420                 425                 430

Pro Ser Ala Ala Val Asn Ala Lys Phe Leu Ala Lys Glu Val Asp Phe
        435                 440                 445

Phe Ser Ile Gly Thr Asn Asp Leu Thr Gln Tyr Thr Leu Ala Val Asp
    450                 455                 460

Arg Gly Asn Glu Met Ile Ser His Leu Tyr Asn Pro Met Ser Pro Ser
465                 470                 475                 480

Val Leu Ser Leu Ile Lys Gln Val Ile Asp Ala Ser His Thr Glu Gly
                485                 490                 495

Lys Trp Thr Gly Met Cys Gly Glu Leu Ala Gly Asp Glu Lys Ala Thr
            500                 505                 510

Ile Leu Leu Leu Gly Met Gly Leu Asp Glu Phe Ser Met Ser Ala Ile
    515                 520                 525

Ser Val Pro Arg Ile Lys Lys Leu Val Arg Ser Val Asn Phe Ala Glu
530                 535                 540

Ala Lys Ala Leu Ala Asp Lys Ala Leu Gln Leu Pro Thr Ala Ala Glu
545                 550                 555                 560

Ile Glu Lys Leu Val Ala Asp Phe Leu Ala Glu Lys Thr Leu Asn
                565                 570                 575

<210> SEQ ID NO 5
<211> LENGTH: 258
<212> TYPE: DNA
<213> ORGANISM: Basfia succiniciproducens
<220> FEATURE:
<221> NAME/KEY: misc_feature
<222> LOCATION: (1)..(258)
<223> OTHER INFORMATION: nucleotide sequence of ptsH-gene from strain
      DD1

<400> SEQUENCE: 5

```
atgtattcaa aagatgttga aattacagct cctaacggct tacacactcg tccggctgca    60
caatttgtaa aagaagcaaa agcgtttgca tctgatgtaa cagtgacttc tgccggtaaa   120
agtgcaagtg cgaaaagttt attcaaatta caaactttag cttaactca aggaactgta   180 attacaattt cagctgaagg cgaagatgag caaaatgctg ttgaccattt agttgcatta   240
attcctacat tagaataa                                                258
```

```
<210> SEQ ID NO 6
<211> LENGTH: 85
<212> TYPE: PRT
<213> ORGANISM: Basfia succiniciproducens
<220> FEATURE:
<221> NAME/KEY: SITE
<222> LOCATION: (1)..(85)
<223> OTHER INFORMATION: amino acid sequence of the enzyme encoded by
      the above ptsH-gene

<400> SEQUENCE: 6
```

```
Met Tyr Ser Lys Asp Val Glu Ile Thr Ala Pro Asn Gly Leu His Thr
 1               5                  10                  15

Arg Pro Ala Ala Gln Phe Val Lys Glu Ala Lys Ala Phe Ala Ser Asp
            20                  25                  30

Val Thr Val Thr Ser Ala Gly Lys Ser Ala Ser Ala Lys Ser Leu Phe
        35                  40                  45

Lys Leu Gln Thr Leu Gly Leu Thr Gln Gly Thr Val Ile Thr Ile Ser
    50                  55                  60

Ala Glu Gly Glu Asp Glu Gln Asn Ala Val Asp His Leu Val Ala Leu
65                  70                  75                  80

Ile Pro Thr Leu Glu
                85
```

```
<210> SEQ ID NO 7
<211> LENGTH: 1029
<212> TYPE: DNA
<213> ORGANISM: Basfia succiniciproducens
<220> FEATURE:
<221> NAME/KEY: misc_feature
<222> LOCATION: (1)..(1029)
<223> OTHER INFORMATION: nucleotide sequence of ldhA-gene from strain
      DD1

<400> SEQUENCE: 7
```

```
ttgacaaaat cagtatgttt aaataaggag ctaactatga aagttgccgt ttacagtact    60
aaaaattatg atcgcaaaca tctggatttg gcgaataaaa aatttaattt tgagcttcat   120
ttctttgatt ttttacttga tgaacaaacc gcgaaaatgg cggagggcgc cgatgccgtc   180 tgtatttcg tcaatgatga tgcgagccgc ccggtgttaa caaagttggc gcaaatcgga   240
gtgaaaatta tcgctttacg ttgtgccggt tttaataatg tggatttgga ggcggcaaaa   300
gagctgggat taaagtcgt acgggtgcct gcgtattcgc cggaagccgt tgccgagcat   360
gcgatcggat taatgctgac tttaaaccgc cgtatccata aggcttatca gcgtacccgc   420
gatgcgaatt tttctctgga aggattggtc ggttttaata tgttcggcaa aaccgccgga   480
gtgattggta cgggaaaaat cggcttggcg gctattcgca tttttaaagg cttcggtatg   540
gacgttctgg cgtttgatcc ttttaaaaat ccggcggcgg aagcgttggg cgcaaaatat   600
gtcggtttag acgagcttta tgcaaaatcc catgttatca ctttgcattg cccggctacg   660
gcggataatt atcatttatt aaatgaagcg gcttttaata aatgcgcga cggtgtaatg   720
```

-continued

```
attattaata ccagccgcgg cgttttaatt gacagccggg cggcaatcga agcgttaaaa    780
cggcagaaaa tcggcgctct cggtatggat gtttatgaaa atgaacggga tttgtttttc    840
gaggataaat ctaacgatgt tattacggat gatgtattcc gtcgcctttc ttcctgtcat    900
aatgtgcttt ttaccggtca tcaggcgttt ttaacggaag aagcgctgaa taatatcgcc    960
gatgtgactt tatcgaatat tcaggcggtt tccaaaaatg caacgtgcga aaatagcgtt   1020
gaaggctaa                                                           1029
```

<210> SEQ ID NO 8
<211> LENGTH: 342
<212> TYPE: PRT
<213> ORGANISM: Basfia succiniciproducens
<220> FEATURE:
<221> NAME/KEY: SITE
<222> LOCATION: (1)..(342)
<223> OTHER INFORMATION: amino acid sequence of LdhA from strain DD1

<400> SEQUENCE: 8

```
Met Thr Lys Ser Val Cys Leu Asn Lys Glu Leu Thr Met Lys Val Ala
  1               5                  10                  15

Val Tyr Ser Thr Lys Asn Tyr Asp Arg Lys His Leu Asp Leu Ala Asn
             20                  25                  30

Lys Lys Phe Asn Phe Glu Leu His Phe Phe Asp Phe Leu Leu Asp Glu
         35                  40                  45

Gln Thr Ala Lys Met Ala Glu Gly Ala Asp Ala Val Cys Ile Phe Val
     50                  55                  60

Asn Asp Asp Ala Ser Arg Pro Val Leu Thr Lys Leu Ala Gln Ile Gly
 65                  70                  75                  80

Val Lys Ile Ile Ala Leu Arg Cys Ala Gly Phe Asn Asn Val Asp Leu
                 85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
    130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
    210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
```

```
                290              295              300
Thr Gly His Gln Ala Phe Leu Thr Glu Glu Ala Leu Asn Asn Ile Ala
305              310              315              320

Asp Val Thr Leu Ser Asn Ile Gln Ala Val Ser Lys Asn Ala Thr Cys
                325              330              335

Glu Asn Ser Val Glu Gly
            340

<210> SEQ ID NO 9
<211> LENGTH: 741
<212> TYPE: DNA
<213> ORGANISM: Basfia succiniciproducens
<220> FEATURE:
<221> NAME/KEY: misc_feature
<222> LOCATION: (1)..(741)
<223> OTHER INFORMATION: nucleotide sequence of pflA-gene from strain
      DD1

<400> SEQUENCE: 9
atgtcggttt taggacgaat tcattcattt gaaacctgcg ggacagttga cgggccggga      60
atccgcttta ttttattttt acaaggctgc ttaatgcgtt gtaaatactg ccataataga     120
gacacctggg atttgcacgg cggtaaagaa atttccgttg aagaattaat gaagaagtg     180 gtgacctatc gccattttat gaacgcctcg ggcggcggag ttaccgcttc ggcggtgaa     240 gctatttac aggcggaatt tgtacgggac tggttcagag cctgccataa agaaggaatt     300
aatacttgct tggataccaa cggtttcgtc cgtcatcatg atcatattat tgatgaattg     360
attgatgaca cggatcttgt gttgcttgac ctgaaagaaa tgaatgaacg ggttcacgaa     420
agcctgattg gcgtgccgaa taaaagagtg ctcgaattcg caaatatttt agcggatcga     480
aatcagcgta cctggatccg ccatgttgta gtgcccggtt atacagatag tgacgaagat     540
ttgcacatgc tggggaattt cattaaagat atgaagaata tcgaaaagt ggaattatta     600 ccttatcacc gtctaggcgc ccataaatgg gaagtactcg gcgataaata cgagcttgaa     660
gatgtaaaac cgccgacaaa agaattaatg gagcatgtta aggggttgct tgcaggctac     720
gggcttaatg tgacatatta g                                              741

<210> SEQ ID NO 10
<211> LENGTH: 246
<212> TYPE: PRT
<213> ORGANISM: Basfia succiniciproducens
<220> FEATURE:
<221> NAME/KEY: SITE
<222> LOCATION: (1)..(246)
<223> OTHER INFORMATION: amino acid sequence of PflA from strain DD1

<400> SEQUENCE: 10

Met Ser Val Leu Gly Arg Ile His Ser Phe Glu Thr Cys Gly Thr Val
1               5                  10                  15

Asp Gly Pro Gly Ile Arg Phe Ile Leu Phe Leu Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Val Val Thr Tyr Arg
    50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys His
                85                  90                  95
```

Lys Glu Gly Ile Asn Thr Cys Leu Asp Thr Asn Gly Phe Val Arg His
              100                 105                 110

His Asp His Ile Ile Asp Glu Leu Ile Asp Asp Thr Asp Leu Val Leu
          115                 120                 125

Leu Asp Leu Lys Glu Met Asn Glu Arg Val His Glu Ser Leu Ile Gly
130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
              165                 170                 175

Ser Asp Glu Asp Leu His Met Leu Gly Asn Phe Ile Lys Asp Met Lys
          180                 185                 190

Asn Ile Glu Lys Val Glu Leu Leu Pro Tyr His Arg Leu Gly Ala His
              195                 200                 205

Lys Trp Glu Val Leu Gly Asp Lys Tyr Glu Leu Glu Asp Val Lys Pro
          210                 215                 220

Pro Thr Lys Glu Leu Met Glu His Val Lys Gly Leu Leu Ala Gly Tyr
225                 230                 235                 240

Gly Leu Asn Val Thr Tyr
              245

<210> SEQ ID NO 11
<211> LENGTH: 2313
<212> TYPE: DNA
<213> ORGANISM: Basfia succiniciproducens
<220> FEATURE:
<221> NAME/KEY: misc_feature
<222> LOCATION: (1)..(2313)
<223> OTHER INFORMATION: nucleotide sequence of pflD-gene from strain
      DD1

<400> SEQUENCE: 11
atggctgaat taacagaagc tcaaaaaaaa gcatgggaag gattcgttcc cggtgaatgg      60
caaaacggcg taaatttacg tgactttatc caaaaaaact atactccgta tgaaggtgac     120
gaatcattct tagctgatgc gactcctgca accagcgagt tgtggaacag cgtgatggaa     180
ggcatcaaaa tcgaaaacaa aactcacgca cctttagatt tcgacgaaca tactccgtca     240
actatcactt ctcacaagcc tggttatatc aataaagatt tagaaaaaat cgttggtctt     300
caaacagacg ctccgttaaa acgtgcaatt atgccgtacg gcggtatcaa aatgatcaaa     360
ggttcttgcg aagtttacgg tcgtaaatta gatccgcaag tagaatttat tttcaccgaa     420
tatcgtaaaa cccataacca aggcgtattc gacgtttata cgccggatat tttacgctgc     480
cgtaaatcag gcgtgttaac cggtttaccg gatgcttacg gtcgtggtcg tattatcggt     540
gactaccgtc gtttagcggt atacggtatt gattacctga tgaaagataa aaaagcccaa     600
ttcgattcat acaaccgcg tttggaagcg ggcgaagaca ttcaggcaac tatccaatta     660
cgtgaagaaa ttgccgaaca cacccgcgct ttaggcaaaa tcaaagaaat ggcggcatct     720
tacggttacg acatttccgg ccctgcgaca aacgcacagg aagcaatcca atggacatat     780
tttgcttatc tggcagcggt taaatcacaa aacggtgcgg caatgtcatt cggtcgtacg     840
tctacattct tagatatcta tatcgaacgt gacttaaaac gcggtttaat cactgaacaa     900
caggcgcagg aattaatgga ccacttagta atgaaattac gtatggttcg tttcttacgt     960
acgccggaat acgatcaatt attctcaggc gaccgatgt gggcaaccga actatcgcc    1020 ggtatgggct tagacggtcg tccgttggta actaaaaaca gcttccgcgt attacatact    1080

```
ttatacacta tgggtacttc tccggaacca aacttaacta ttctttggtc cgaacaatta    1140
cctgaagcgt tcaaacgttt ctgtgcgaaa gtatctattg atacttcctc cgtacaatac    1200
gaaaatgatg acttaatgcg tcctgacttc aacaacgatg actatgcaat cgcatgctgc    1260
gtatcaccga tggtcgtagg taaacaaatg caattcttcg gtgcgcgcgc aaacttagct    1320
aaaactatgt tatacgcaat taacggcggt atcgatgaga aaatggtat gcaagtcggt     1380 cctaaaactc gccgattac agacgaagta ttgaatttcg ataccgtaat cgaacgtatg    1440
gacagtttca tggactggtt ggcgactcaa tatgtaaccg cattgaacat catccacttc    1500
atgcacgata aatatgcata tgaagcggca ttgatggcgt tccacgatcg cgacgtattc    1560
cgtacaatgg cttgcggtat cgcgggtctt tccgtggctg cggactcatt atccgcaatc    1620
aaatatgcga aagttaaacc gattcgcggc gacatcaaag ataaagacgg taatgtcgtg    1680
gcctcgaatg ttgctatcga cttcgaaatt gaaggcgaat atccgcaatt cggtaacaat    1740
gatccgcgtg ttgatgattt agcggtagac ttagttgaac gtttcatgaa aaaagttcaa    1800
aaacacaaaa cttaccgcaa cgcaactccg acacaatcta tcctgactat cacttctaac    1860
gtggtatacg gtaagaaaac cggtaatact ccggacggtc gtcgagcagg cgcgccattc    1920
ggaccgggtg caaacccaat gcacggtcgt gaccaaaaag gtgcggttgc ttcacttact    1980
tctgtggcta aacttccgtt cgcttacgcg aaagacggta tttcatatac cttctctatc    2040
gtaccgaacg cattaggtaa agatgacgaa gcgcaaaaac gcaaccttgc cggtttaatg    2100
gacggttatt tccatcatga agcgacagtg gaaggcggtc aacacttgaa tgttaacgtt    2160
cttaaccgtg aaatgttgtt agacgcgatg gaaaatccgg aaaaataccc gcaattaacc    2220
attcgtgttt caggttacgc ggttcgtttc aactcattaa ctaaagagca acaacaagac    2280
gtcatcactc gtacgtttac acaatcaatg taa                                 2313
```

<210> SEQ ID NO 12
<211> LENGTH: 770
<212> TYPE: PRT
<213> ORGANISM: Basfia succiniciproducens
<220> FEATURE:
<221> NAME/KEY: SITE
<222> LOCATION: (1)..(770)
<223> OTHER INFORMATION: amino acid of PflD from strain DD1

<400> SEQUENCE: 12

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125
```

-continued

```
Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
            165                 170                 175

Arg Ile Ile Gly Asp Tyr Arg Arg Leu Ala Val Tyr Gly Ile Asp Tyr
        180                 185                 190

Leu Met Lys Asp Lys Ala Gln Phe Asp Ser Leu Gln Pro Arg Leu
    195                 200                 205

Glu Ala Gly Glu Asp Ile Gln Ala Thr Ile Gln Leu Arg Glu Glu Ile
210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
            245                 250                 255

Gln Trp Thr Tyr Phe Ala Tyr Leu Ala Ala Val Lys Ser Gln Asn Gly
        260                 265                 270

Ala Ala Met Ser Phe Gly Arg Thr Ser Thr Phe Leu Asp Ile Tyr Ile
    275                 280                 285

Glu Arg Asp Leu Lys Arg Gly Leu Ile Thr Glu Gln Gln Ala Gln Glu
290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
            325                 330                 335

Glu Thr Ile Ala Gly Met Gly Leu Asp Gly Arg Pro Leu Val Thr Lys
        340                 345                 350

Asn Ser Phe Arg Val Leu His Thr Leu Tyr Thr Met Gly Thr Ser Pro
    355                 360                 365

Glu Pro Asn Leu Thr Ile Leu Trp Ser Glu Gln Leu Pro Glu Ala Phe
370                 375                 380

Lys Arg Phe Cys Ala Lys Val Ser Ile Asp Thr Ser Ser Val Gln Tyr
385                 390                 395                 400

Glu Asn Asp Asp Leu Met Arg Pro Asp Phe Asn Asn Asp Asp Tyr Ala
            405                 410                 415

Ile Ala Cys Cys Val Ser Pro Met Val Val Gly Lys Gln Met Gln Phe
        420                 425                 430

Phe Gly Ala Arg Ala Asn Leu Ala Lys Thr Met Leu Tyr Ala Ile Asn
    435                 440                 445

Gly Gly Ile Asp Glu Lys Asn Gly Met Gln Val Gly Pro Lys Thr Ala
450                 455                 460

Pro Ile Thr Asp Glu Val Leu Asn Phe Asp Thr Val Ile Glu Arg Met
465                 470                 475                 480

Asp Ser Phe Met Asp Trp Leu Ala Thr Gln Tyr Val Thr Ala Leu Asn
            485                 490                 495

Ile Ile His Phe Met His Asp Lys Tyr Ala Tyr Glu Ala Ala Leu Met
        500                 505                 510

Ala Phe His Asp Arg Asp Val Phe Arg Thr Met Ala Cys Gly Ile Ala
    515                 520                 525

Gly Leu Ser Val Ala Ala Asp Ser Leu Ser Ala Ile Lys Tyr Ala Lys
530                 535                 540

Val Lys Pro Ile Arg Gly Asp Ile Lys Asp Lys Asp Gly Asn Val Val
```

```
                545                 550                 555                 560
Ala Ser Asn Val Ala Ile Asp Phe Glu Ile Glu Gly Glu Tyr Pro Gln
                    565                 570                 575

Phe Gly Asn Asn Asp Pro Arg Val Asp Asp Leu Ala Val Asp Leu Val
                580                 585                 590

Glu Arg Phe Met Lys Lys Val Gln Lys His Lys Thr Tyr Arg Asn Ala
            595                 600                 605

Thr Pro Thr Gln Ser Ile Leu Thr Ile Thr Ser Asn Val Val Tyr Gly
        610                 615                 620

Lys Lys Thr Gly Asn Thr Pro Asp Gly Arg Arg Ala Gly Ala Pro Phe
625                 630                 635                 640

Gly Pro Gly Ala Asn Pro Met His Gly Arg Asp Gln Lys Gly Ala Val
                    645                 650                 655

Ala Ser Leu Thr Ser Val Ala Lys Leu Pro Phe Ala Tyr Ala Lys Asp
                660                 665                 670

Gly Ile Ser Tyr Thr Phe Ser Ile Val Pro Asn Ala Leu Gly Lys Asp
            675                 680                 685

Asp Glu Ala Gln Lys Arg Asn Leu Ala Gly Leu Met Asp Gly Tyr Phe
        690                 695                 700

His His Glu Ala Thr Val Gly Gly Gln His Leu Asn Val Asn Val
705                 710                 715                 720

Leu Asn Arg Glu Met Leu Leu Asp Ala Met Glu Asn Pro Glu Lys Tyr
                    725                 730                 735

Pro Gln Leu Thr Ile Arg Val Ser Gly Tyr Ala Val Arg Phe Asn Ser
                740                 745                 750

Leu Thr Lys Glu Gln Gln Gln Asp Val Ile Thr Arg Thr Phe Thr Gln
            755                 760                 765

Ser Met
    770

<210> SEQ ID NO 13
<211> LENGTH: 600
<212> TYPE: DNA
<213> ORGANISM: Basfia succiniciproducens
<220> FEATURE:
<221> NAME/KEY: misc_feature
<222> LOCATION: (1)..(600)
<223> OTHER INFORMATION: nucleotide sequence of wcaJ-gene from strain
      DD1

<400> SEQUENCE: 13
atgataaaac gccttttcga tattgttgtc gcattgatag cattgatttt gttttcgccc      60
ttatatttgt ttgtggctta taaggtaaaa caaaatttgg gatcaccggt gttatttaaa     120
caaacccgcc ccggattgca tggtaaaccc tttgagatga ttaagttcag aacaatgaaa     180
gacggcgcag atgaaaacgg taatattttg ccggatgcgg agcgcttaac acctttcggc     240
aaaatgttgc gcgctaccag tctggacgag ttgccggaac tttggaatgt attaaaaggt     300
gatatgagtc tggtggggcc gcgtcctcta ctgatggaat atttgccgct gtataacgaa     360
agacaggcta agcgccatga agtgaaaccc ggaattaccg ttatgcaca ggtaaacggt      420 cgcaatgcca tcagttggga gcagaaattt gaattggatg cctggtatgt tgaacatcaa     480
tccttgtggc tggatttgaa aattatcgca agaccatcc aaaaagtgat cgcaaaagac      540
gatattaatg cggcagatga tgccaccatg cctaaatttg aagggaataa aaaatcatga     600
```

<210> SEQ ID NO 14

```
<211> LENGTH: 199
<212> TYPE: PRT
<213> ORGANISM: Basfia succiniciproducens
<220> FEATURE:
<221> NAME/KEY: SITE
<222> LOCATION: (1)..(199)
<223> OTHER INFORMATION: amino acid sequence of the enzyme encoded by
      the above wcaJ-gene

<400> SEQUENCE: 14
```

| | | | | | | | | | | | | | | |
|---|---|---|---|---|---|---|---|---|---|---|---|---|---|---|
| Met | Ile | Lys | Arg | Leu | Phe | Asp | Ile | Val | Val | Ala | Leu | Ile | Ala | Leu | Ile |
| 1 | | | | 5 | | | | | 10 | | | | | 15 | |

Leu Phe Ser Pro Leu Tyr Leu Phe Val Ala Tyr Lys Val Lys Gln Asn
             20                  25                  30

Leu Gly Ser Pro Val Leu Phe Lys Gln Thr Arg Pro Gly Leu His Gly
         35                  40                  45

Lys Pro Phe Glu Met Ile Lys Phe Arg Thr Met Lys Asp Gly Ala Asp
     50                  55                  60

Glu Asn Gly Asn Ile Leu Pro Asp Ala Glu Arg Leu Thr Pro Phe Gly
65                  70                  75                  80

Lys Met Leu Arg Ala Thr Ser Leu Asp Glu Leu Pro Glu Leu Trp Asn
                 85                  90                  95

Val Leu Lys Gly Asp Met Ser Leu Val Gly Pro Arg Pro Leu Leu Met
            100                 105                 110

Glu Tyr Leu Pro Leu Tyr Asn Glu Arg Gln Ala Lys Arg His Glu Val
        115                 120                 125

Lys Pro Gly Ile Thr Gly Tyr Ala Gln Val Asn Gly Arg Asn Ala Ile
    130                 135                 140

Ser Trp Glu Gln Lys Phe Glu Leu Asp Ala Trp Tyr Val Glu His Gln
145                 150                 155                 160

Ser Leu Trp Leu Asp Leu Lys Ile Ile Ala Lys Thr Ile Gln Lys Val
                165                 170                 175

Ile Ala Lys Asp Asp Ile Asn Ala Ala Asp Asp Ala Thr Met Pro Lys
            180                 185                 190

Phe Glu Gly Asn Lys Lys Ser
        195

```
<210> SEQ ID NO 15
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of pykA-gene from strain
      DD1

<400> SEQUENCE: 15
atgtccagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa     180
ttaggtaaac acgtagcaat cttaggtgac ttacaaggcc ctaaaatccg tgtttctact     240 tttaagaag gcaaaatttt cttaaatatc ggtgataaat tcattttaga cgcagagatg     300
cctaaaggtg aagtaaccca ggaagcggtt ggtttagact ataaaacatt accgcaagat     360
gtggttccgg gcgatatctt attattagat gacggtcgag ttcaattgaa gtattggca     420 accgaaggtg caaagtatt caccgaagta acggtcggtg ccccactatc aaataataaa     480
```

```
ggcattaaca aattaggcgg cggtttatct gccgatgcat taaccgaaaa agataaagcg    540
gatatcatta ctgcggcgcg tatcggtgtg gattaccttg ccgtatcttt cccgcgttca    600
agcgcggatt taaactacgc ccgtcaatta gcaaagatg cgggcttgga tgcgaaaatc     660
gttgcgaaag tagaacgtgc cgaaacagtt gaaacggacg aagcaatgga cgatatcatc    720
aatgcggcgg acgtaatcat ggttgcgcgc ggtgacttag gtgttgaaat cggtgatccg    780
gaattagtcg gtgttcagaa aaaattaatc cgtcgttcac gtcagttaaa tcgtgttgtt    840
attaccgcaa ctcaaatgat ggaatcaatg attagtaatc ctatgccgac tcgtgcggaa    900
gtaatggacg tagctaacgc agtattggac ggtaccgatg cggtaatgct ttctgctgaa    960
accgcggctg gtcaatatcc ggcggaaact gttgcggcga tggcgaaagt tgcgttaggt   1020
gcggagaaaa tgccaagcat taatgtgtct aaacaccgta tgaacgttca attcgagtct   1080
attgaagaat ctgttgcgat gtctgcaatg tatgcggcaa accacatgag aggcgtagcg   1140
gcgattatca cattaacaag tagcggtcgt actgctcgtt taatgtctcg cattagttcc   1200
ggtttaccaa tctttgcatt gtcacgtaac gaatctacat taaacttatg cgcattatat   1260
cgtggtgtga caccggttca ttttgataaa gacagccgta cctcagaagg tgcgacagcg   1320
gcggttcaat tattaaaaga cgaaggtttc ttagtgtctg gcgatttagt gttattaact   1380
cagggcgacg caagcagttc tagcggtact aacctttgcc gtacattgat tgttgaataa   1440
```

<210> SEQ ID NO 16
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence of PykA from strain DD1

<400> SEQUENCE: 16

```
Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
        35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
            100                 105                 110

Asp Tyr Lys Thr Leu Pro Gln Asp Val Val Pro Gly Asp Ile Leu Leu
        115                 120                 125

Leu Asp Asp Gly Arg Val Gln Leu Lys Val Leu Ala Thr Glu Gly Ala
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Asp Ala Leu Thr Glu
                165                 170                 175

Lys Asp Lys Ala Asp Ile Ile Thr Ala Ala Arg Ile Gly Val Asp Tyr
            180                 185                 190
```

Leu Ala Val Ser Phe Pro Arg Ser Ser Ala Asp Leu Asn Tyr Ala Arg
                195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
                260                 265                 270

Ser Arg Gln Leu Asn Arg Val Val Ile Thr Ala Thr Gln Met Met Glu
            275                 280                 285

Ser Met Ile Ser Asn Pro Met Pro Thr Arg Ala Glu Val Met Asp Val
            290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
                325                 330                 335

Val Ala Leu Gly Ala Glu Lys Met Pro Ser Ile Asn Val Ser Lys His
            340                 345                 350

Arg Met Asn Val Gln Phe Glu Ser Ile Glu Glu Ser Val Ala Met Ser
            355                 360                 365

Ala Met Tyr Ala Ala Asn His Met Arg Gly Val Ala Ala Ile Ile Thr
            370                 375                 380

Leu Thr Ser Ser Gly Arg Thr Ala Arg Leu Met Ser Arg Ile Ser Ser
385                 390                 395                 400

Gly Leu Pro Ile Phe Ala Leu Ser Arg Asn Glu Ser Thr Leu Asn Leu
                405                 410                 415

Cys Ala Leu Tyr Arg Gly Val Thr Pro Val His Phe Asp Lys Asp Ser
            420                 425                 430

Arg Thr Ser Glu Gly Ala Thr Ala Val Gln Leu Leu Lys Asp Glu
            435                 440                 445

Gly Phe Leu Val Ser Gly Asp Leu Val Leu Leu Thr Gln Gly Asp Ala
    450                 455                 460

Ser Ser Ser Ser Gly Thr Asn Leu Cys Arg Thr Leu Ile Val Glu
465                 470                 475

<210> SEQ ID NO 17
<211> LENGTH: 4285
<212> TYPE: DNA
<213> ORGANISM: Artificial Sequence
<220> FEATURE:
<223> OTHER INFORMATION: complete nucleotide sequence of plasmid pSacB

<400> SEQUENCE: 17
tcgagaggcc tgacgtcggg cccggtacca cgcgtcatat gactagttcg gacctaggga      60
tatcgtcgac atcgatgctc ttctgcgtta attaacaatt gggatcctct agactccata     120
ggccgctttc ctggctttgc ttccagatgt atgctctcct ccggagagta ccgtgacttt     180
attttcggca caaatacagg ggtcgatgga taaatacggc gatagtttcc tgacggatga     240
tccgtatgta ccggcggaag acaagctgca aacctgtcag atggagattg atttaatggc     300
ggatgtgctg agagcaccgc cccgtgaatc gcagaactg atccgctatg tgtttgcgga      360
tgattggccg gaataaataa agccgggctt aatacagatt aagcccgtat aggtattat     420

```
tactgaatac caaacagctt acggaggacg gaatgttacc cattgagaca accagactgc    480
cttctgatta ttaatatttt tcactattaa tcagaaggaa taaccatgaa ttttacccgg    540
attgacctga atacctggaa tcgcagggaa cactttgccc tttatcgtca gcagattaaa    600
tgcggattca gcctgaccac caaactcgat attaccgctt tgcgtaccgc actggcggag    660
acaggttata agttttatcc gctgatgatt tacctgatct cccgggctgt taatcagttt    720
ccggagttcc ggatggcact gaaagacaat gaacttattt actgggacca gtcagacccg    780
gtctttactg tctttcataa agaaaccgaa acattctctg cactgtcctg ccgttatttt    840
ccggatctca gtgagtttat ggcaggttat aatgcggtaa cggcagaata tcagcatgat    900
accagattgt ttccgcaggg aaatttaccg gagaatcacc tgaatatatc atcattaccg    960
tgggtgagtt ttgacgggat taacctgaa catcaccgga aatgatgatt attttgcccc     1020 ggttttacg atggcaaagt tcagcagga aggtgaccgc gtattattac ctgtttctgt       1080
acaggttcat catgcagtct gtgatggctt tcatgcagca cggtttatta atacacttca    1140
gctgatgtgt gataacatac tgaaataaat taattaattc tgtatttaag ccaccgtatc    1200
cggcaggaat ggtggctttt tttttatatt ttaaccgtaa tctgtaattt cgtttcagac    1260
tggttcagga tgagctcgct tggactcctg ttgatagatc cagtaatgac ctcagaactc    1320
catctggatt tgttcagaac gctcggttgc cgccgggcgt tttttattgg tgagaatcca    1380
agcactagcg cgcgccggc cggcccggtg tgaaataccg cacagatgcg taaggagaaa     1440
ataccgcatc aggcgctctt ccgcttcctc gctcactgac tcgctgcgct cggtcgttcg    1500
gctgcggcga gcggtatcag ctcactcaaa ggcggtaata cggttatcca gaatcagg     1560 ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta cactagaagg acagtatttg gtatctgcgc    2100
tctgctgaag ccagttacct tcggaaaaag agttggtagc tcttgatccg gcaaacaaac    2160
caccgctggt agcggtggtt ttttgtttg caagcagcag attacgcgca gaaaaaaagg     2220
atctcaagaa gatcctttga tcttttctac ggggtctgac gctcagtgga acgaaaactc    2280
acgttaaggg attttggtca tgagattatc aaaaaggatc ttcacctaga tccttttaaa    2340
ggccggccgc ggccgccatc ggcattttct tttgcgtttt tatttgttaa ctgttaattg    2400
tccttgttca aggatgctgt ctttgacaac agatgttttt ttgcctttga tgttcagcag    2460
gaagctcggc gcaaacgttg attgtttgtc tgcgtagaat cctctgtttg tcatatagct    2520
tgtaatcacg acattgtttc ctttcgcttg aggtacagcg aagtgtgagt aagtaaaggt    2580
tacatcgtta ggatcaagat ccatttttaa cacaaggcca gttttgttca gcggcttgta    2640
tgggccagtt aaagaattag aaacataacc aagcatgtaa atatcgttag acgtaatgcc    2700
gtcaatcgtc attttgatc cgcgggagtc agtgaacagg taccatttgc cgttcatttt    2760
aaagacgttc gcgcgttcaa tttcatctgt tactgtgtta gatgcaatca gcggtttcat    2820
```

```
cactttttc   agtgtgtaat   catcgtttag   ctcaatcata   ccgagagcgc   cgtttgctaa     2880
ctcagccgtg   cgtttttat    cgctttgcag   aagtttttga   ctttcttgac   ggaagaatga     2940
tgtgcttttg   ccatagtatg   ctttgttaaa   taaagattct   tcgccttggt   agccatcttc     3000
agttccagtg   tttgcttcaa   atactaagta   tttgtggcct   ttatcttcta   cgtagtgagg     3060
atctctcagc   gtatggttgt   cgcctgagct   gtagttgcct   tcatcgatga   actgctgtac     3120
attttgatac   gtttttccgt   caccgtcaaa   gattgattta   taatcctcta   caccgttgat     3180
gttcaaagag   ctgtctgatg   ctgatacgtt   aacttgtgca   gttgtcagtg   tttgtttgcc     3240
gtaatgttta   ccgagaaat    cagtgtagaa   taaacggatt   tttccgtcag   atgtaaatgt     3300
ggctgaacct   gaccattctt   gtgtttggtc   ttttaggata   gaatcatttg   catcgaattt     3360
gtcgctgtct   ttaaagacgc   ggccagcgtt   tttccagctg   tcaatagaag   tttcgccgac     3420
tttttgatag   aacatgtaaa   tcgatgtgtc   atccgcattt   ttaggatctc   cggctaatgc     3480
aaagacgatg   tggtagccgt   gatagtttgc   gacagtgccg   tcagcgtttt   gtaatggcca     3540
gctgtcccaa   acgtccaggc   cttttgcaga   agagatattt   ttaattgtgg   acgaatcaaa     3600
ttcagaaact   tgatattttt   catttttttg   ctgttcaggg   atttgcagca   tatcatggcg     3660
tgtaatatgg   gaaatgccgt   atgtttcctt   atatggcttt   tggttcgttt   ctttcgcaaa     3720
cgcttgagtt   gcgcctcctg   ccagcagtgc   ggtagtaaag   gttaatactg   ttgcttgttt     3780
tgcaaacttt   ttgatgttca   tcgttcatgt   ctccttttt    atgtactgtg   ttagcggtct     3840
gcttcttcca   gccctcctgt   ttgaagatgg   caagttagtt   acgcacaata   aaaaagacc      3900 taaaatatgt   aagggtgac    gccaaagtat   acactttgcc   ctttacacat   tttaggtctt     3960
gcctgcttta   tcagtaacaa   acccgcgcga   tttactttc    gacctcattc   tattagactc     4020
tcgtttggat   tgcaactggt   ctattttcct   cttttgtttg   atagaaaatc   ataaaggat      4080 ttgcagacta   cgggcctaaa   gaactaaaaa   atctatctgt   ttcttttcat   tctctgtatt     4140
ttttatagtt   tctgttgcat   gggcataaag   ttgcctttt    aatcacaatt   cagaaaatat     4200
cataatatct   catttcacta   aataatagtg   aacggcaggt   atatgtgatg   ggttaaaaag     4260
gatcggcggc   cgctcgattt   aaatc                                                 4285
```

<210> SEQ ID NO 18
<211> LENGTH: 7074
<212> TYPE: DNA
<213> ORGANISM: Artificial Sequence
<220> FEATURE:
<223> OTHER INFORMATION: complete nucleotide sequence of plasmid
   pSacB_delta_ldhA

<400> SEQUENCE: 18

```
tcgagaggcc   tgacgtcggg   cccggtacca   cgcgtcatat   gactagttcg   gacctaggga      60
tgggtcagcc   tgaacgaacc   gcacttgtat   gtaggtagtt   ttgaccgccc   gaatattcgt     120
tataccttgg   tggaaaaatt   caaaccgatg   gagcaattat   acaattttgt   ggcggcgcaa     180
aaaggtaaaa   gcggtatcgt   ctattgcaac   agccgtagca   agtggagcg    cattgcggaa     240 gccctgaaga   aaagaggcat   tccgcagcc    gcttatcatg   cgggcatgga   gccgtcgcag     300
cgggaagcgg   tgcaacaggc   gtttcaacgg   gataatattc   aagtggtggt   ggcgaccatt     360
gcttttggta   tggggatcaa   caaatctaat   gtgcgttttg   tggcgcatt    tgatttatct     420 cgcagcattg   aggcgtatta   tcaggaaacc   gggcgcgcgg   ggcgggacga   cctgccggcg     480
gaagcggtac   tgttttacga   gccggcggat   tatgcctggt   tgcataaaat   tttattggaa     540
```

```
gagccggaaa gcccgcaacg ggatattaaa cggcataagc tggaagccat cggcgaattt    600
gccgaaagcc agacctgccg tcgtttagtg ctgttaaatt atttcggcga aaaccgccaa    660
acgccatgta ataactgtga tatctgcctc gatccgccga aaaaatatga cggattatta    720
gacgcgcaga aaatcctttc gaccatttat cgcaccgggc aacgtttcgg cacgcaatac    780
gtaatcggcg taatgcgcgg tttgcagaat cagaaaataa aagaaaatca acatgatgag    840
ttgaaagtct acggaattgg caaagataaa agcaaagaat actggcaatc ggtaattcgt    900
cagctgattc atttgggctt tgtgcaacaa atcatcagcg atttcggcat ggggaccaga    960
ttacagctca ccgaaagcgc gcgtcccgtg ctgcgcggcg aagtgtcttt ggaactggcc   1020
atgccgagat tatcttccat taccatggta caggctccgc aacgcaatgc ggtaaccaac   1080
tacgacaaag atttatttgc ccgcctgcgt ttcctgcgca aacagattgc cgacaaagaa   1140
aacattccgc cttatattgt gttcagtgac gcgaccttgc aggaaatgtc gttgtatcag   1200
ccgaccagca aagtggaaat gctgcaaatc aacggtgtcg cgccatcaa atggcagcgc    1260 ttcggacagc cttttatggc gattattaaa gaacatcagg ctttgcgtaa agcgggtaag   1320
aatccgttgg aattgcaatc ttaaaatttt taactttttg accgcacttt taaggttagc   1380
aaattccaat aaaaagtgcg gtgggttttc gggaattttt aacgcgctga tttcctcgtc   1440
ttttcaattt yttcgyctcc atttgttcgg yggttgccgg atcctttctt gactgagatc   1500
cataagagag tagaatagcg ccgcttatat ttttaatagc gtacctaatc gggtacgctt   1560
tttttatgcg gaaaatccat atttttctac cgcacttttt cttttaaagat ttatacttaa   1620 gtctgtttga ttcaatttat ttggaggttt tatgcaacac attcaactgg ctcccgattt   1680
aacattcagt cgcttaattc aaggattctg gcggttaaaa agctggcgga atcgccgca    1740 ggaattgctt acattcgtta agcaaggatt agaattaggc gttgatacgc tggatcatgc   1800
cgcttgttac ggggcttta cttccgaggc ggaattcgga cgggcgctgg cgctggataa    1860
atccttgcgc gcacagctta cttttggtgac caaatgcggg attttgtatc ctaatgaaga   1920
attacccgat ataaaatccc atcactatga caacagctac cgccatatta tgtggtcggc   1980
gcaacgttcc attgaaaaac tgcaatgcga ctatttagat gtattgctga ttcaccgwct   2040
ttctccctgt gcggatcccg aacaaatcgc gcgggctttt gatgaacttt atcaaaccgg   2100
raaagtacgt tatttcgggg tatctaacta tacgccggct aagttcgcca tgttgcaatc   2160
ttatgtgaat cagccgttaa tcactaatca aattgagatt cgcctcttc atcgtcaggc    2220 ttttgatgac ggtaccctgg attttttact ggaaaaacgt attcaaccga tggcatggtc   2280
gccacttgcc ggcggtcgtt tattcaatca ggatgagaac agtcgggcgg tgcaaaaaac   2340
attactcgaa atcggtgaaa cgaaaggaga aaccgtttta gatacattgg cttatgcctg   2400
gttattggcg catccggcaa aaattatgcc ggttatgggg tccggtaaaa ttgaacgggt   2460
aaaaagcgcg gcggatgcgt tacgaatttc cttcactgag gaagaatgga ttaaggttta   2520
tgttgccgca cagggacggg atattccgta acatcatccg tctaatcctg cgtatctggg   2580
gaaagatgcg tcatcgtaag aggtctataa tattcgtcgt tttgataagg gtgccatatc   2640
cggcacccgt taaaatcaca ttgcgttcgc aacaaaatta ttccttacga atagcattca   2700 cctctttttaa cagatgttga atatccgtat cggcaaaaat atcctctata tttgcggtta   2760
aacggcgccg ccagttagca tattgagtgc tggttcccgg aatattgacg ggttcggtca   2820
taccgagcca gtcttcaggt tggaatcccc atcgtcgaca tcgatgctct tctgcgttaa   2880
```

```
ttaacaattg ggatcctcta gactccatag gccgctttcc tggctttgct tccagatgta   2940
tgctctcctc cggagagtac cgtgacttta ttttcggcac aaatacaggg gtcgatggat   3000
aaatacggcg atagtttcct gacggatgat ccgtatgtac cggcggaaga caagctgcaa   3060
acctgtcaga tggagattga tttaatggcg gatgtgctga gagcaccgcc ccgtgaatcc   3120
gcagaactga tccgctatgt gttttgcggat gattggccgg aataaataaa gccgggctta   3180
atacagatta agcccgtata gggtattatt actgaatacc aaacagctta cggaggacgg   3240
aatgttaccc attgagacaa ccagactgcc ttctgattat taatattttt cactattaat   3300
cagaaggaat aaccatgaat tttacccgga ttgacctgaa tacctggaat cgcagggaac   3360
actttgccct ttatcgtcag cagattaaat gcggattcag cctgaccacc aaactcgata   3420
ttaccgcttt gcgtaccgca ctggcggaga caggttataa gttttatccg ctgatgattt   3480
acctgatctc ccgggctgtt aatcagtttc cggagttccg gatggcactg aaagacaatg   3540
aacttattta ctgggaccag tcagacccgg tctttactgt cttccataaa gaaaccgaaa   3600
cattctctgc actgtcctgc cgttattttc cggatctcag tgagtttatg gcaggttata   3660
atgcggtaac ggcagaatat cagcatgata ccagattgtt ccgcagggga aatttaccgg   3720
agaatcacct gaatatatca tcattaccgt gggtgagttt tgacgggatt taacctgaac   3780
atcaccggaa atgatgatta ttttgccccg gttttacga tggcaaagtt tcagcaggaa   3840
ggtgaccgcg tattattacc tgtttctgta caggttcatc atgcagtctg tgatggcttt   3900
catgcagcac ggtttattaa tacacttcag ctgatgtgtg ataacatact gaaataaatt   3960
aattaattct gtatttaagc caccgtatcc ggcaggaatg gtggcttttt ttttatattt   4020
taaccgtaat ctgtaatttc gtttcagact ggttcaggat gagctcgctt ggactcctgt   4080
tgatagatcc agtaatgacc tcagaactcc atctggattt gttcagaacg ctcggttgcc   4140
gccgggcgtt ttttattggt gagaatccaa gcactagcgg cgcgccggcc ggcccggtgt   4200
gaaataccgc acagatgcgt aaggagaaaa taccgcatca ggcgctcttc cgcttcctcg   4260
ctcactgact cgctgcgctc ggtcgttcgg ctgcggcgag cggtatcagc tcactcaaag   4320
gcggtaatac ggttatccac agaatcaggg gataacgcag gaaagaacat gtgagcaaaa   4380
ggccagcaaa aggccaggaa ccgtaaaaag gccgcgttgc tggcgttttt ccataggctc   4440 cgccccctg acgagcatca caaaaatcga cgctcaagtc agaggtggcg aaacccgaca   4500
ggactataaa gataccaggc gtttccccct ggaagctccc tcgtgcgctc tcctgttccg   4560
accctgccgc ttaccggata cctgtccgcc tttctccctt cgggaagcgt ggcgctttct   4620
catagctcac gctgtaggta tctcagttcg gtgtaggtcg ttcgctccaa gctgggctgt   4680
gtgcacgaac ccccgttca gcccgaccgc tgcgccttat ccggtaacta tcgtcttgag   4740
tccaacccgg taagacacga cttatcgcca ctggcagcag ccactggtaa caggattagc   4800
agagcgaggt atgtaggcgg tgctacagag ttcttgaagt ggtggcctaa ctacggctac   4860
actagaagga cagtatttgg tatctgcgct ctgctgaagc cagttacctt cggaaaaaga   4920
gttggtagct cttgatccgg caaacaaacc accgctggta gcggtggttt ttttgtttgc   4980
aagcagcaga ttacgcgcag aaaaaaagga tctcaagaag atcctttgat cttttctacg   5040
gggtctgacg ctcagtggaa cgaaaactca cgttaaggga ttttggtcat gagattatca   5100
aaaaggatct tcacctagat ccttttaaag gccggccgcg gccgccatcg gcattttctt   5160
ttgcgttttt atttgttaac tgttaattgt ccttgttcaa ggatgctgtc tttgacaaca   5220
gatgttttct tgcctttgat gttcagcagg aagctcggcg caaacgttga ttgtttgtct   5280
```

```
gcgtagaatc ctctgtttgt catatagctt gtaatcacga cattgtttcc tttcgcttga      5340
ggtacagcga agtgtgagta agtaaaggtt acatcgttag gatcaagatc catttttaac      5400
acaaggccag ttttgttcag cggcttgtat gggccagtta agaattaga aacataacca       5460 agcatgtaaa tatcgttaga cgtaatgccg tcaatcgtca ttttttgatcc gcgggagtca     5520 gtgaacaggt accatttgcc gttcatttta aagacgttcg cgcgttcaat ttcatctgtt      5580
actgtgttag atgcaatcag cggtttcatc acttttttca gtgtgtaatc atcgtttagc      5640
tcaatcatac cgagagcgcc gtttgctaac tcagccgtgc gttttttatc gctttgcaga      5700 agttttgac tttcttgacg gaagaatgat gtgcttttgc catagtatgc tttgttaaat       5760
aaagattctt cgccttggta gccatcttca gttccagtgt ttgcttcaaa tactaagtat      5820
ttgtggcctt tatcttctac gtagtgagga tctctcagcg tatggttgtc gcctgagctg      5880
tagttgcctt catcgatgaa ctgctgtaca ttttgatacg ttttccgtc accgtcaaag       5940 attgatttat aatcctctac accgttgatg ttcaaagagc tgtctgatgc tgatacgtta      6000
acttgtgcag ttgtcagtgt ttgtttgccg taatgtttac cggagaaatc agtgtagaat      6060
aaacggattt ttccgtcaga tgtaaatgtg gctgaacctg accattcttg tgtttggtct      6120
tttaggatag aatcatttgc atcgaatttg tcgctgtctt taaagacgcg gccagcgttt      6180
ttccagctgt caatagaagt ttcgccgact ttttgataga acatgtaaat cgatgtgtca     6240
tccgcatttt taggatctcc ggctaatgca aagacgatgt ggtagccgtg atagtttgcg     6300
acagtgccgt cagcgttttg taatggccag ctgtcccaaa cgtccaggcc ttttgcagaa      6360
gagatatttt taattgtgga cgaatcaaat tcagaaactt gatattttc attttttttgc     6420 tgttcaggga tttgcagcat atcatggcgt gtaatatggg aaatgccgta tgtttccta     6480 tatggctttt ggttcgtttc tttcgcaaac gcttgagttg cgcctcctgc cagcagtgcg      6540
gtagtaaagg ttaatactgt tgcttgtttt gcaaactttt tgatgttcat cgttcatgtc     6600
tcctttttta tgtactgtgt tagcggtctg cttcttccag ccctcctgtt tgaagatggc     6660
aagttagtta cgcacaataa aaaaagacct aaaatatgta aggggtgacg ccaaagtata     6720
cactttgccc tttacacatt ttaggtcttg cctgctttat cagtaacaaa cccgcgcgat     6780
ttacttttcg acctcattct attagactct cgtttggatt gcaactggtc tatttttcctc    6840 ttttgtttga tagaaaatca taaaggatt tgcagactac gggcctaaag aactaaaaaa     6900
tctatctgtt tcttttcatt ctctgtatttt tttatagttt ctgttgcatg ggcataaagt     6960
tgccttttta atcacaattc agaaaatatc ataaatatctc atttcactaa ataatagtga    7020
acggcaggta tatgtgatgg gttaaaaagg atcggcggcc gctcgattta aatc          7074
```

<210> SEQ ID NO 19
<211> LENGTH: 7183
<212> TYPE: DNA
<213> ORGANISM: Artificial Sequence
<220> FEATURE:
<223> OTHER INFORMATION: complete nucleotide sequence of plasmid
      pSacB_delta_pflA

<400> SEQUENCE: 19

```
tcgagtcaat gcggatttga cttatgatgt ggcaaacaac cgatttccga ttattactac        60
acgtaaaagt tattggaaag cggcgattgc ggagtttctg ggttatatcc gcggctacga       120
taatgcggcg gatttccgta aattaggagc aaaaacctgg gatgccaacg ctaatgaaaa      180
tcaggtatgg ctgaataacc ctcatcgcaa aggcaccgac gacatggggc gcgtttacgg      240
```

```
cgtacagggc agagcctggc gtaagcctaa cggcgaaacc gttgatcaat tacgcaaaat    300
tgtcaacaat ttaagtcgcg gcattgatga tcgcggcgaa attctgacct ttttaaaccc    360
gggcgaattc gatctcggtt gtctgcgccc ttgtatgtac aatcacacgt tttctttgct    420
gggcgatacg ctttatttaa ccagttatca acgctcctgt gacgtacctt taggcttgaa    480
tttcaatcaa attcaagtat ttacattctt agctttaatg gcgcagatta ccggtaaaaa    540
agccggtcag gcatatcaca aaatcgtcaa tgcgcatatt tacgaagacc agctggaact    600
aatgcgcgac gtgcagttaa aacgcgaacc gttcccgtcg ccaaaactgg aaattaatcc    660
ggacattaaa accccttgaag atttagaaac ctgggtaacc atggatgatt caacgtcgt    720 tggttaccaa tgccacgaac cgataaaata tccgttctcg gtataaaccg acaaaagtgc    780
ggtcaaaaat ttaatatttt catctgttat agaaaatatt tttcaacata aatctaggg    840 atgcctgttt ggcgtccgta aatacgcaga aaatattaa attttgacc gcacttttt     900 catctcaatt aacagcctga taattcttat ggatcaacaa attagctttg acgaaaaaat    960
gatgaatcga gctcttttcc ttgccgacaa ggcggaagct ttaggggaaa ttcccgtagg   1020
tgccgtattg gtggatgaac ggggcaatat cattggtgaa ggctggaacc tctctattgt   1080
gaactcggat cccaccgccc atgccgaaat tattgcgttg cgtaacgccg cgcagaaaat   1140
ccaaaattac cgcctgctca ataccacttt atacgtgact ttagaaccct gcaccatgtg   1200
cgccggcgcg attttacaca gccgaatcaa acgcttggta ttcggggcgt ccgattacaa   1260
aaccggtgcg gtgggttcca gatttcattt ttttgaggat tataaaatga atcatggggt   1320
tgagatcaca agcggtgtct tacaggatca atgcagtcag aagttaagcc gcttttttcca  1380 aaagcgcagg gaacagaaaa aacaacaaaa agctaccgca cttttacaac cccccggct   1440 taactcctct gaaaaatagt gacaaaaaaa ccgtcataat gtttacgacg gttttttat    1500 ttcttaatat gcccttaaat aatcaacaaa atatagcaag aagattatag caaagaattt   1560 cgttttttc agagaatagt caaatcttcg caaaaaacta ccgcactttt atccgcttta   1620
atcaggggaa ttaaaacaaa aaaattccgc ctattgaggc ggaatttatt aagcaataag   1680
acaaactctc aattacattg attgtgtaaa cgtacgagtg atgacgtctt gttgttgctc    1740
tttagttaat gagttgaaac gaaccgcgta acctgaaaca cgaatggtta attgcgggta   1800
tttttccgga ttttccatcg cgtctaacaa catttcacgg ttaagaacgt taacattcaa    1860
gtgttgaccg ccttccactg tcgcttcatg atggaaataa ccgtccatta aaccggcaag   1920
gttgcgtttt tgcgcttcgt catctttacc taatgcgttc ggtacgatag agaaggtata   1980
tgaaataccg tctttcgcgt aagcgaacgg aagtttagcc acagaagtaa gtgaagcaac   2040
cgcacctttt tggtcacgac cgtgcattgg gtttgcaccc ggtccgaatg gcgcgcctgc   2100
tcgacgaccg tccggagtat taccggtttt cttaccgtat accacgttag aagtgatagt   2160
caggatagat tgtgtcggag ttgcgttgcg gtaagttttg tgtttttgaa ctttttttcat  2220 gaaacgttca actaagtcta ccgctaaatc atcaacacgc ggatcattgt taccgaattg   2280
cggatattcg ccttcaattt cgaagtcgat agcaacattc gaggccacga cattaccgtc   2340
tttatctttg atgtcgccgc gaatcggttt aactttcgca tatttgattg cggataatga   2400
gtccgcagcc acggaaagac ccgcgatacc gcaagccatt gtacggaata cgtcgcgatc   2460
gtggaacgcc atcaatgccg cttcatatgc atatttatcg tgcatgaagt ggatgatgtt   2520
caatgcggtt acatattgag tcgccaacca gtccatgaaa ctgtccatac gttcgattac   2580
```

```
ggtatcgaaa ttcaatactt cgtctgtaat cggcgcagtt ttaggaccga cttgcatacc    2640 attttctca tcgataccgc cgttaattgc gtataacata gttttagcta agtttgcgcg     2700
cgcaccgaag aattgcattt gtttacctac gaccatcggt gatacgcagc atgcgattgc    2760
atagtcatcg ttgttgaagt caggacgcat taagtcatca ttttcgtatt gtacggagga    2820
agtatcaata gatactttcg cacagaaacg tttgaacgct tcaggtaatt gttcggacca    2880
aagaatagtt aagtttggtt ccggagaagt acccatagtg tataaagtat gtaatacgcg    2940
gaagctgttt ttagttacca acggacgacc gtctaagccc ataccggcga tagtttcggt    3000
tgccctctag actccatagg ccgctttcct ggctttgctt ccagatgtat gctctcctcc    3060
ggagagtacc gtgactttat tttcggcaca aatacagggg tcgatggata aatacggcga    3120
tagtttcctg acggatgatc cgtatgtacc ggcggaagac aagctgcaaa cctgtcagat    3180
ggagattgat ttaatggcgg atgtgctgag agcaccgccc cgtgaatccg cagaactgat    3240
ccgctatgtg tttgcggatg attggccgga ataaataaag ccgggcttaa tacagattaa    3300
gcccgtatag ggtattatta ctgaatacca aacagcttac ggaggacgga atgttaccca    3360
ttgagacaac cagactgcct tctgattatt aatattttc actattaatc agaaggaata    3420
accatgaatt ttacccggat tgacctgaat acctggaatc gcagggaaca ctttgccctt    3480
tatcgtcagc agattaaatg cggattcagc ctgaccacca aactcgatat taccgctttg    3540
cgtaccgcac tggcggagac aggttataag ttttatccgc tgatgattta cctgatctcc    3600
cgggctgtta atcagtttcc ggagttccgg atggcactga agacaatga acttatttac     3660 tgggaccagt cagacccggt ctttactgtc tttcataaag aaaccgaaac attctctgca    3720
ctgtcctgcc gttattttcc ggatctcagt gagtttatgg caggttataa tgcggtaacg    3780
gcagaatatc agcatgatac cagattgttt ccgcagggaa atttaccgga gaatcacctg    3840
aatatatcat cattaccgtg ggtgagtttt gacgggattt aacctgaaca tcaccggaaa    3900
tgatgattat ttttgccccgg ttttttacgat ggcaaagttt cagcaggaag gtgaccgcgt   3960
attattacct gtttctgtac aggttcatca tgcagtctgt gatggctttc atgcagcacg    4020
gtttattaat acacttcagc tgatgtgtga taacatactg aaataaatta attaattctg    4080
tatttaagcc accgtatccg gcaggaatgg tggcttttt tttatatttt aaccgtaatc    4140
tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260
tttattggtg agaatccaag cactagcggc gcgccggccg gccgggtgtg aaataccgca    4320
cagatgcgta aggagaaaat accgcatcag gcgctcttcc gcttcctcgc tcactgactc    4380
gctgcgctcg tcgttcggc tgcggcgagc ggtatcagct cactcaaagg cggtaatacg    4440
gttatccaca gaatcagggg ataacgcagg aaagaacatg tgagcaaaag gccagcaaaa    4500
ggccaggaac cgtaaaaagg ccgcgttgct ggcgtttttc cataggctcc gcccccctga    4560
cgagcatcac aaaaatcgac gctcaagtca gaggtggcga aacccgacag gactataaag    4620
ataccaggcg tttccccctg gaagctccct cgtgcgctct cctgttccga ccctgccgct    4680
taccggatac ctgtccgcct ttctcccttc gggaagcgtg cgctttctc atagctcacg    4740 ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaaggac    4980
```

```
agtatttggt atctgcgctc tgctgaagcc agttaccttc ggaaaaagag ttggtagctc    5040
ttgatccggc aaacaaacca ccgctggtag cggtggtttt tttgtttgca agcagcagat    5100
tacgcgcaga aaaaaggat ctcaagaaga tcctttgatc ttttctacgg ggtctgacgc    5160
tcagtggaac gaaaactcac gttaagggat tttggtcatg agattatcaa aaaggatctt    5220
cacctagatc cttttaaagg ccggccgcgg ccgccatcgg catttctttt tgcgttttta    5280
tttgttaact gttaattgtc cttgttcaag gatgctgtct ttgacaacag atgttttctt    5340
gcctttgatg ttcagcagga agctcggcgc aaacgttgat tgtttgtctg cgtagaatcc    5400
tctgtttgtc atatagcttg taatcacgac attgtttcct ttcgcttgag gtacagcgaa    5460
gtgtgagtaa gtaaaggtta catcgttagg atcaagatcc atttttaaca caaggccagt    5520
tttgttcagc ggcttgtatg ggccagttaa agaattagaa acataaccaa gcatgtaaat    5580
atcgttagac gtaatgccgt caatcgtcat ttttgatccg cgggagtcag tgaacaggta    5640
ccatttgccg ttcattttaa agacgttcgc gcgttcaatt tcatctgtta ctgtgttaga    5700
tgcaatcagc ggtttcatca cttttttcag tgtgtaatca tcgtttagct caatcatacc    5760
gagagcgccg tttgctaact cagccgtgcg ttttttatcg ctttgcagaa gttttttgact    5820 ttcttgacgg aagaatgatg tgcttttgcc atagtatgct ttgttaaata aagattcttc    5880
gccttggtag ccatcttcag ttccagtgtt tgcttcaaat actaagtatt tgtggccttt    5940
atcttctacg tagtgaggat ctctcagcgt atggttgtcg cctgagctgt agttgccttc    6000
atcgatgaac tgctgtacat tttgatacgt ttttccgtca ccgtcaaaga ttgatttata    6060
atcctctaca ccgttgatgt tcaaagagct gtctgatgct gatacgttaa cttgtgcagt    6120
tgtcagtgtt tgtttgccgt aatgtttacc ggagaaatca gtgtagaata acggattttt    6180
tccgtcagat gtaaatgtgg ctgaacctga ccattcttgt gtttggtctt ttaggataga    6240
atcatttgca tcgaatttgt cgctgtcttt aaagacgcgg ccagcgtttt tccagctgtc    6300
aatagaagtt tcgccgactt tttgatagaa catgtaaatc gatgtgtcat ccgcattttt    6360
aggatctccg gctaatgcaa agacgatgtg gtagccgtga tagtttgcga cagtgccgtc    6420
agcgttttgt aatggccagc tgtcccaaac gtccaggcct tttgcagaag agatattttt    6480
aattgtggac gaatcaaatt cagaaacttg atattttttca ttttttttgct gttcagggat    6540 ttgcagcata tcatggcgtg taatatggga aatgccgtat gtttccttat atggcttttg    6600 gttcgttttct ttcgcaaacg cttgagttgc gcctcctgcc agcagtgcgg tagtaaaggt    6660
taatactgtt gcttgttttg caaacttttt gatgttcatc gttcatgtct cctttttat    6720 gtactgtgtt agcggtctgc ttcttccagc cctcctgttt gaagatggca agttagttac    6780
gcacaataaa aaaagaccta aaatatgtaa ggggtgacgc caaagtatac actttgccct    6840
ttacacattt taggtcttgc ctgctttatc agtaacaaac ccgcgcgatt tacttttcga    6900
cctcattcta ttagactctc gtttggattg caactggtct attttcctct tttgtttgat    6960
agaaaatcat aaaaggattt gcagactacg ggcctaaaga actaaaaaat ctatctgttt    7020
cttttcattc tctgtatttt ttatagtttc tgttgcatgg gcataaagtt gccttttaa    7080 tcacaattca gaaatatca taatatctca tttcactaaa taatagtgaa cggcaggtat    7140
atgtgatggg ttaaaaagga tcggcggccg ctcgatttaa atc    7183
```

<210> SEQ ID NO 20
<211> LENGTH: 5363
<212> TYPE: DNA

<213> ORGANISM: Artificial Sequence
<220> FEATURE:
<223> OTHER INFORMATION: complete nucleotide sequence of plasmid pSacB_pykA1

<400> SEQUENCE: 20

```
tcgagcagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa     180
ttaggtaaac acgtagcaat cttaggtgac ttacaaggcc ctaaaatccg tgtttctact     240
tttaaagaag gcaaaatttt cttaaatatc ggtgataaat tcattttaga cgcagagatg     300
cctaaaggtg aaggtaacca ggaagcggtt ggtttagact ataaaacatt accgcaagat     360
gtggttccgg gcgatatctt attattagat gacggtcgag ttcaattgaa agtattggca     420
accgaaggtg caaaagtatt caccgaagta acggtcggtg cccactatc  aaataataaa     480
ggcattaaca aattaggcgg cggtttatct gccgatgcat taaccgaaaa agataaagcg     540
gatatcatta ctgcggcgcg tatcggtgtg gattaccttg ccgtatcttt cccgcgttca     600
agcgcggatt taaactacgc ccgtcaatta gcaaaagatg cgggcttgga tgcgaaaatc     660
gttgcgaaag tagaacgtgc cgaaacagtt gaaacggacg aagcaatgga cgatatcatc     720
aatgcggcgg acgtaatcat ggttgcgcgc ggtgacttag gtgttgaaat cggtgatccg     780
gaattagtcg gtgttcagaa aaaattaatc cgtcgttcac gtcagttaaa tcgtgttgtt     840
attaccgcaa ctcaaatgat ggaatcaatg attagtaatc ctatgccgac tcgtgcggaa     900
gtaatggacg tagctaacgc agtattggac ggtaccgatg cggtaatgct ttctgctgaa     960
accgcggctg tcaatatcc  ggcggaaact gttgcggcga tggcgaaagt tgcgttaggt    1020
gcggagaaaa tgccaagcat taatgtgtct aaacaccgta tgaacgttca attcgagtct    1080
attgaagaat ctgttgcgat gtctgcaatg tatgcggcaa ccacatgag  aggcgtagcg    1140
gcgattatca cattaacaag tagcggtcgt actgctcgtt taatgtctag actccatagg    1200
ccgctttcct ggctttgctt ccagatgtat gctctcctcc ggagagtacc gtgactttat    1260
tttcggcaca aatacagggg tcgatggata aatacggcga tagtttcctg acggatgatc    1320
cgtatgtacc ggcggaagac aagctgcaaa cctgtcagat ggagattgat ttaatggcgg    1380
atgtgctgag agcaccgccc cgtgaatccg cagaactgat ccgctatgtg tttgcggatg    1440
attggccgga ataaataaag ccgggcttaa tacagattaa gcccgtatag ggtattatta    1500
ctgaatacca aacagcttac ggaggacgga atgttaccca ttgagacaac cagactgcct    1560
tctgattatt aatatttttc actattaatc agaaggaata accatgaatt ttacccggat    1620
tgacctgaat acctggaatc gcagggaaca ctttgcccct tatcgtcagc agattaaatg    1680
cggattcagc ctgaccacca aactcgatat taccgctttg cgtaccgcac tggcggagac    1740
aggttataag tttatatccgc tgatgattta cctgatctcc cggctgtta  atcagtttcc    1800
ggagttccgg atggcactga agacaatga  acttatttac tgggaccagt cagacccggt    1860
ctttactgtc tttcataaag aaaccgaaac attctctgca ctgtcctgcc gttattttcc    1920
ggatctcagt gagtttatgg caggttataa tgcggtaacg gcagaatatc agcatgatac    1980
cagattgttt ccgcagggaa atttaccgga gaatcacctg aatatatcat cattaccgtg    2040
ggtgagtttt gacgggattt aacctgaaca tcaccggaaa tgatgattat tttgccccgg    2100
tttttacgat ggcaaagttt cagcaggaag gtgaccgcgt attattacct gtttctgtac    2160
```

```
aggttcatca tgcagtctgt gatggctttc atgcagcacg gtttattaat acacttcagc      2220
tgatgtgtga taacatactg aaataaatta attaattctg tatttaagcc accgtatccg      2280
gcaggaatgg tggcttttt tttatatttt aaccgtaatc tgtaatttcg tttcagactg       2340
gttcaggatg agctcgcttg gactcctgtt gatagatcca gtaatgacct cagaactcca     2400
tctggatttg ttcagaacgc tcggttgccg ccgggcgttt tttattggtg agaatccaag      2460
cactagcggc gcgccggccg gcccggtgtg aaataccgca cagatgcgta aggagaaaat     2520
accgcatcag gcgctcttcc gcttcctcgc tcactgactc gctgcgctcg tcgttcggc      2580 tgcggcgagc ggtatcagct cactcaaagg cggtaatacg gttatccaca gaatcagggg    2640
ataacgcagg aaagaacatg tgagcaaaag gccagcaaaa ggccaggaac cgtaaaaagg    2700
ccgcgttgct ggcgttttc cataggctcc gcccccctga cgagcatcac aaaaatcgac      2760
gctcaagtca gaggtggcga aacccgacag gactataaag ataccaggcg tttccccctg     2820
gaagctccct cgtgcgctct cctgttccga cctgccgct taccggatac ctgtccgcct     2880
ttctcccttc gggaagcgtg gcgctttctc atagctcacg ctgtaggtat ctcagttcgg     2940
tgtaggtcgt tcgctccaag ctgggctgtg tgcacgaacc ccccgttcag cccgaccgct    3000
gcgccttatc cggtaactat cgtcttgagt ccaacccggt aagacacgac ttatcgccac     3060
tggcagcagc cactggtaac aggattagca gagcgaggta tgtaggcggt gctacagagt     3120
tcttgaagtg gtggcctaac tacggctaca ctagaaggac agtatttggt atctgcgctc    3180
tgctgaagcc agttaccttc ggaaaaagag ttggtagctc ttgatccggc aaacaaacca    3240
ccgctggtag cggtggtttt tttgtttgca agcagcagat tacgcgcaga aaaaaaggat    3300
ctcaagaaga tcctttgatc ttttctacgg ggtctgacgc tcagtggaac gaaaactcac    3360 gttaaggat tttggtcatg agattatcaa aaaggatctt cacctagatc cttttaaagg     3420
ccggccgcgg ccgccatcgg cattttcttt tgcgttttta tttgttaact gttaattgtc    3480
cttgttcaag gatgctgtct ttgacaacag atgttttctt gcctttgatg ttcagcagga    3540
agctcggcgc aaacgttgat tgtttgtctg cgtagaatcc tctgtttgtc atatagcttg    3600
taatcacgac attgttcct ttcgcttgag gtacagcgaa gtgtgagtaa gtaaaggtta    3660
catcgttagg atcaagatcc attttaaca caaggccagt tttgttcagc ggcttgtatg     3720
ggccagttaa agaattagaa acataaccaa gcatgtaaat atcgttagac gtaatgccgt   3780
caatcgtcat ttttgatccg cgggagtcag tgaacaggta ccatttgccg ttcatttaa    3840 agacgttcgc gcgttcaatt tcatctgtta ctgtgttaga tgcaatcagc ggtttcatca    3900
cttttttcag tgtgtaatca tcgtttagct caatcatacc gagagcgccg tttgctaact    3960
cagccgtgcg ttttttatcg ctttgcagaa gttttttgact ttcttgacgg aagaatgatg   4020
tgcttttgcc atagtatgct ttgttaaata aagattcttc gccttggtag ccatcttcag    4080
ttccagtgtt tgcttcaaat actaagtatt tgtggccttt atcttctacg tagtgaggat    4140
ctctcagcgt atggttgtcg cctgagctgt agttgccttc atcgatgaac tgctgtacat    4200
tttgatacgt ttttccgtca ccgtcaaaga ttgatttata atcctctaca ccgttgatgt    4260
tcaaagagct gtctgatgct gatacgttaa cttgtgcagt tgtcagtgtt tgtttgccgt    4320
aatgtttacc ggagaaatca gtgtagaata aacggatttt tccgtcagat gtaaatgtgg    4380
ctgaacctga ccattcttgt gtttggtctt ttaggataga atcatttgca tcgaatttgt    4440
cgctgtcttt aaagacgcgg ccagcgtttt tccagctgtc aatagaagtt tcgccgactt    4500
tttgatagaa catgtaaatc gatgtgtcat ccgcattttt aggatctccg gctaatgcaa    4560
```

```
agacgatgtg gtagccgtga tagtttgcga cagtgccgtc agcgttttgt aatggccagc    4620
tgtcccaaac gtccaggcct tttgcagaag agatatttt aattgtggac gaatcaaatt    4680
cagaaacttg atatttttca ttttttgct gttcagggat ttgcagcata tcatggcgtg    4740
taatatggga aatgccgtat gtttccttat atggcttttg gttcgtttct ttcgcaaacg    4800
cttgagttgc gcctcctgcc agcagtgcgg tagtaaaggt taatactgtt gcttgttttg    4860 caaactttt gatgttcatc gttcatgtct ccttttttat gtactgtgtt agcggtctgc    4920
ttcttccagc cctcctgttt gaagatggca agttagttac gcacaataaa aaaagaccta    4980
aaatatgtaa ggggtgacgc caaagtatac actttgccct ttacacattt taggtcttgc    5040
ctgctttatc agtaacaaac ccgcgcgatt tactttcga cctcattcta ttagactctc    5100
gtttggattg caactggtct attttcctct tttgtttgat agaaaatcat aaaaggattt    5160
gcagactacg ggcctaaaga actaaaaaat ctatctgttt cttttcattc tctgtatttt    5220
ttatagtttc tgttgcatgg gcataaagtt gccttttaa tcacaattca gaaaatatca    5280
taatatctca tttcactaaa taatagtgaa cggcaggtat atgtgatggg ttaaaaagga    5340
tcggcggccg ctcgatttaa atc                                            5363
```

<210> SEQ ID NO 21
<211> LENGTH: 7557
<212> TYPE: DNA
<213> ORGANISM: Artificial Sequence
<220> FEATURE:
<223> OTHER INFORMATION: complete nucleotide sequence of plasmid pSacB_wcaJ*

<400> SEQUENCE: 21

```
tcgagtaagc cgattcagct gatccgccac atggggaaaa agcctaatct gcggaatatg      60
aaaccgatac cagtccagta aagttgacaa atcgacatca tattgctcaa ccaagtattg     120
aaaagcgttt tcaccgcgat gatacaattc gaccagccgg ttaaataacg tttcactccg     180
ttccggtgcc aaacgagacg caatatgctt ataggcggaa tacagaaaat cgatttccgc     240
ataaagcgta tcgtccaaat ctaaaaccaa cgctttattt ttcataatga tgagccagta     300
cttccgcgtc ataccgcaac attaataaat ccgcttccca gtcttcgaac gcaggaatcg     360
gctgattaaa caaatattcc tgaatcaacc aacggggata attggctccc gccagataac     420
tcaacggata accgccgccg aacctagggt taatttcaat accaagaatt tcagcggtgg     480
attccttata aaatacttgg attgttaagc aaccgcgcgc ccccggtaaa cgggacaatt     540
tttccgataa ttgcgtcacg atggcatttt ttctggtcac acctttgtta atttcccccg     600
ctctgacaaa aattctcttt ctcggtaccg cactttcag ttcggaattt ttatcaaaat      660
aacaatccac ggtatattcg tcgtattccg ccggcgaaat atattgcata acattaatt      720 cgggattttc caattgctcc ggtgaaatat cttccggttt ctccgccaca aaaattcctt     780
tacttaaact accgttgtaa ggcttcacaa aaacaggata ttcaaattga ccttttttcaa    840 actgcttcgg taccgcaata ttatgttcaa taaacagttg attggttaat cgtttgtcgc     900
gacattttct gacaaactct gtatcactaa cggaaataaa aataccttt tctttaaacc      960 gttgcagatg ttcgcttaaa ataagcaatt ccgtatcaat agtcggaata atcaatttca    1020
cgttattttc ttcacagatt ttaagtaagg tcggaatata ctccgcatca gtgacccggg    1080
gtacaggaaa atgtccgtcg gccacataac aagccgcgc caactcggga tttaaatcta    1140
cggttaacac ttttccgtca cttactaact gcgataattc cttttttaaac gcctgaacga    1200
```

```
gagaaacacg ttgtccggcc gatgtaacaa gaatattcat gatttttat tcccttcaaa    1260 tttaggcatg gtggcatcat ctgccgcatt aatatcgtct tttgcgatca cttttttggat   1320 ggtctttgcg ataattttca aatccagcca caaggattga tgttcaacat accaggcatc   1380
caattcaaat ttctgctccc aactgatggc attgcgaccg tttacctgtg cataaccggt   1440
aattccgggt ttcacttcat ggcgcttagc ctgtctttcg ttatacagcg gcaaatattc   1500
catcagtaga ggacgcggcc ccaccagact catatcacct tttaatacat tccaaagttc   1560
cggcaactcg tccagactgg tagcgcgcaa cattttgccg aaaggtgtta agcgctccgc   1620
atccggcaaa atattaccgt tttcatctgc gccgtctttc attgttctga acttaatcat   1680
ctcaaagggt ttaccatgca atccggggcg ggtttgttta ataacaccg gtgatcccaa    1740 atttttgtttt accttgataa gccacaaaca aatataaggg cgaaaacaaa atcaatgcta   1800
tcaatgcgac aacaatatcg aaaaggcgtt ttatcatgaa aatctcctac gaccgaccaa   1860
tttggggctg acaaaagtgc cgttttttcac cagaaccgta taaactaaaa ccaggaaaag   1920
cggataccag actaacggca gtcttaatat ggaagacggc acccaaacga tccaacaaaa   1980
attaataaaa ataaataaaa taaatatacg ttctttccac gccaacaatt gggtattcat   2040
cacatagata attgaattta ataaaaaata tataaatgcc aaaaatgcaa aaatgccaaa   2100
tgccaaataa agttctataa agaagctatg cggattagtg taaccaaag ggaaacttaa    2160 ctttatttga tcgaaatact gaatgtagtc ccgcggtcca taccccaacc ataaaatttt   2220
aaaattatct aaaaatgtcg tataaatttc cgtccggtaa cctacggact tatcatcgcc   2280
catagaaaat attaccaatg aaaaacgttc aatcggacgc tccagccaat caattttggc   2340
gagcagaata aacacttcct gtaaccaaga aagattaaat ataataatg cgatcacgca    2400 ggcgaaaaac agatataccg ccttaaaata ggtagatgcg tttaaaaaca agatcagcat   2460
caacataatc aaatagctca gtaataccga acgggaggca ctgatcacaa tagctaaccc   2520
cataataaaa ataagagcat agccgattaa cttaattttc cagttgtttt ctctgatgat   2580
gtaaaaaaat cccaccgcca ccgcaagaga aatcataatt acggactggt cattggtatt   2640
aaagaaaaaa cctttaaacg ccttatcagt tacggttaat tcttcattac ccgaaaccaa   2700
ctggaacccc aataaagcct caataaaaaa gcccgccagc acaattaatg atattcccaa   2760
caaaaggtgc ctaatccctg cttctccatc accccggtta aacgtcaaaa aagaataatg   2820
aaataaaaac atcacaattc cgaagaaaaa caaatcaact aatttttctg tagaaaacgc   2880
atttaatacc gataaaaagc cgaagaaaaa caacacgtac accggaaact gtaatttaaa   2940
aaaatcagtt tccatatccc ttaaaaaagg ggttattacc gctaagaaaa agaacaaaaa   3000
acacaacgca ctatctaacc tcggcactcc tatttgtgtc gatagtgcgg gagaaagtat   3060
caccagtccc aacgcaaaga gtaatagcaa cttaaaaatg ctgataacat taatattcat   3120
atcaaataat attttttgatt aatttctcaa tttcttata agaacgctcg cgcagaaact    3180
tctcttttgc cagcgataaa ttcacttgcg acattttgtc taaaaccgtt ctgtcttcgg   3240
ccaatttatt caacgtctca gccaactccc gataatctcc cgccgtatat tgaattccac   3300
cgcctttcgc cagtagttttt tccacttcag gatgtttctg acagcttaca atcggtaatg   3360
cgcaacagat ataatcggat ctagactcca taggccgctt tcctggcttt gcttccagat   3420
gtatgctctc ctccggagag taccgtgact ttatttttcgg cacaaataca ggggtcgatg   3480
gataaatacg gcgatagttt cctgacggat gatccgtatg taccggcgga agacaagctg   3540
```

```
caaacctgtc agatggagat tgatttaatg gcggatgtgc tgagagcacc gccccgtgaa    3600
tccgcagaac tgatccgcta tgtgtttgcg gatgattggc cggaataaat aaagccgggc    3660
ttaatacaga ttaagcccgt atagggtatt attactgaat accaaacagc ttacggagga    3720
cggaatgtta cccattgaga caaccagact gccttctgat tattaatatt tttcactatt    3780
aatcagaagg aataaccatg aattttaccc ggattgacct gaatacctgg aatcgcaggg    3840
aacactttgc cctttatcgt cagcagatta aatgcggatt cagcctgacc accaaactcg    3900
atattaccgc tttgcgtacc gcactggcgg agacaggtta aagttttat ccgctgatga    3960 tttacctgat ctcccgggct gttaatcagt ttccggagtt ccggatggca ctgaaagaca    4020
atgaacttat ttactgggac cagtcagacc cggtctttac tgtctttcat aaagaaaccg    4080
aaacattctc tgcactgtcc tgccgttatt ttccggatct cagtgagttt atggcaggtt    4140
ataatgcggt aacggcagaa tatcagcatg ataccagatt gtttccgcag ggaaatttac    4200
cggagaatca cctgaatata tcatcattac cgtgggtgag ttttgacggg atttaacctg    4260
aacatcaccg gaaatgatga ttattttgcc ccggttttta cgatggcaaa gtttcagcag    4320
gaaggtgacc gcgtattatt acctgtttct gtacaggttc atcatgcagt ctgtgatggc    4380
tttcatgcag cacggtttat taatacactt cagctgatgt gtgataacat actgaaataa    4440
attaattaat tctgtattta agccaccgta tccggcagga atggtggctt tttttttata    4500
ttttaaccgt aatctgtaat ttcgtttcag actggtcag gatgagctcg cttggactcc    4560
tgttgataga tccagtaatg acctcagaac tccatctgga tttgttcaga acgctcggtt    4620
gccgccgggc gttttttatt ggtgagaatc caagcactag cggcgcgccg gccggcccgg    4680
tgtgaaatac cgcacagatg cgtaaggaga aaataccgca tcaggcgctc ttccgcttcc    4740
tcgctcactg actcgctgcg ctcggtcgtt cggctgcggc gagcggtatc agctcactca    4800
aaggcggtaa tacggttatc cacagaatca ggggataacg caggaaagaa catgtgagca    4860
aaaggccagc aaaaggccag gaaccgtaaa aaggccgcgt tgctggcgtt tttccatagg    4920
ctccgccccc ctgacgagca tcacaaaaat cgacgctcaa gtcagaggtg gcgaaacccg    4980
acaggactat aaagatacca ggcgtttccc cctggaagct ccctcgtgcg ctctcctgtt    5040
ccgaccctgc cgcttaccgg atacctgtcc gcctttctcc cttcgggaag cgtggcgctt    5100
tctcatagct cacgctgtag gtatctcagt tcggtgtagg tcgttcgctc caagctgggc    5160
tgtgtgcacg aaccccccgt tcagcccgac cgctgcgcct tatccggtaa ctatcgtctt    5220
gagtccaacc cggtaagaca cgacttatcg ccactggcag cagccactgg taacaggatt    5280
agcagagcga ggtatgtagg cggtgctaca gagttcttga agtggtggcc taactacggc    5340
tacactagaa ggacagtatt tggtatctgc gctctgctga gccagttac cttcggaaaa    5400 agagttggta gctcttgatc cggcaaacaa accaccgctg gtagcggtgg tttttttgtt    5460
tgcaagcagc agattacgcg cagaaaaaaa ggatctcaag aagatccttt gatcttttct    5520
acggggtctg acgctcagtg gaacgaaaac tcacgttaag ggattttggt catgagatta    5580
tcaaaaagga tcttcaccta gatcctttta aaggccggcc gcggccgcca tcggcatttt    5640
cttttgcgtt tttatttgtt aactgttaat tgtccttgtt caaggatgct gtctttgaca    5700
acagatgttt tcttgccttt gatgttcagc aggaagctcg gcgcaaacgt tgattgtttg    5760
tctgcgtaga atcctctgtt tgtcatatag cttgtaatca cgacattgtt cctttcgct    5820 tgaggtacag cgaagtgtga gtaagtaaag gttacatcgt taggatcaag atccattttt    5880
aacacaaggc cagttttgtt cagcggcttg tatgggccag ttaaagaatt agaaacataa    5940
```

-continued

```
ccaagcatgt aaatatcgtt agacgtaatg ccgtcaatcg tcattttga tccgcgggag    6000
tcagtgaaca ggtaccattt gccgttcatt ttaaagacgt tcgcgcgttc aatttcatct   6060
gttactgtgt tagatgcaat cagcggtttc atcactttt tcagtgtgta atcatcgttt   6120
agctcaatca taccgagagc gccgtttgct aactcagccg tgcgtttttt atcgctttgc   6180
agaagttttt gactttcttg acggaagaat gatgtgcttt tgccatagta tgctttgtta   6240
aataaagatt cttcgccttg gtagccatct tcagttccag tgtttgcttc aaatactaag   6300
tatttgtggc ctttatcttc tacgtagtga ggatctctca gcgtatggtt gtcgcctgag   6360
ctgtagttgc cttcatcgat gaactgctgt acattttgat acgttttttcc gtcaccgtca   6420
aagattgatt tataatcctc tacaccgttg atgttcaaag agctgtctga tgctgatacg   6480
ttaacttgtg cagttgtcag tgtttgtttg ccgtaatgtt taccggagaa atcagtgtag   6540
aataaacgga ttttccgtc agatgtaaat gtggctgaac ctgaccattc ttgtgtttgg   6600
tcttttagga tagaatcatt tgcatcgaat ttgtcgctgt cttaaagac gcggccagcg   6660
tttttccagc tgtcaataga agtttcgccg acttttgat agaacatgta aatcgatgtg   6720
tcatccgcat ttttaggatc tccggctaat gcaaagacga tgtggtagcc gtgatagttt   6780
gcgacagtgc cgtcagcgtt ttgtaatggc cagctgtccc aaacgtccag gccttttgca   6840
gaagagatat ttttaattgt ggacgaatca aattcagaaa cttgtatttt tcattttt    6900
tgctgttcag ggatttgcag catatcatgg cgtgtaatat gggaaatgcc gtatgtttcc   6960
ttatatggct tttggttcgt ttctttcgca aacgcttgag ttgcgcctcc tgccagcagt   7020
gcggtagtaa aggttaatac tgttgcttgt tttgcaaact ttttgatgtt catcgttcat   7080
gtctcctttt ttatgtactg tgttagcggt ctgcttcttc cagccctcct gtttgaagat   7140
ggcaagttag ttacgcacaa taaaaaaaga cctaaaatat gtaagggtg acgccaaagt    7200
atacactttg ccctttacac attttaggtc ttgcctgctt tatcagtaac aaacccgcgc   7260
gatttacttt tcgacctcat tctattagac tctcgtttgg attgcaactg gtctattttc   7320
ctcttttgtt tgatagaaaa tcataaaagg atttgcagac tacgggccta agaactaaa    7380
aaatctatct gtttcttttc attctctgta tttttatag tttctgttgc atgggcataa   7440
agttgccttt ttaatcacaa ttcagaaaat atcataatat ctcatttcac taaataatag   7500
tgaacggcag gtatatgtga tgggttaaaa aggatcggcg ccgctcgat ttaaatc       7557
```

<210> SEQ ID NO 22
<211> LENGTH: 7183
<212> TYPE: DNA
<213> ORGANISM: Artificial Sequence
<220> FEATURE:
<223> OTHER INFORMATION: complete nucleotide sequence of plasmid
    pSacB_delta_ptsA

<400> SEQUENCE: 22

```
tcgagtcgca atgtcctatt ttagacatag cctccgtaag cgcatgggct aaattcatac     60
cgccgctgcg atcccgttgc aaaagatgat atgccatacg ctgtgcggat tcggcccga    120
caccgggcaa acagcgtaaa ctttcgatta aattttctaa taaaggactg gtttgcataa   180
gactctaaaa ataacaaaaa acaaaccgca cttttaaaag tgcggtctta tttcataaaa   240
ttttacttaa aacggcattt taaacccggg aggaatcggc ataccagcgg taactgacgc   300
cattttctct ttttgtaact catccgcgcg gcgagcggca tcattaaatg cggcggcgat   360
gagatcttcc aacatatcct tatcgtcttc cattaatgaa ggatcaattt ccacgcgacg   420
```

```
gcaattatgc gcaccgttaa ttgttacttt aactaaccccc gcaccggact caccggttac      480
ttcaagttgg gcaatttctt cctgcatttt ttgcatacgc tcttgcattt gctgagcttg      540
tttcattaaa ttgcctaagc caccttttcc aaacataatt cttcttccat ttttgagcgt      600
ataaaatata cgaataaatt aaataaaaag tccgctctaa acaaagcgaa ctttctaaca      660
attataatga gactaatcag cttttatttt tttagtgata aaccactga atcgccggca       720 acaacctggc ctactttttt atccaacgca ctaatttcat ccatatttga aattactacc      780
ggagtaagaa tagatttcgc ttttttgttct aaagtggta atcaaactc aataatagta      840 tcaccacgtt tcacagactg accctcttgt gcaacacggg taaaaccttc acctttaagt     900
tcaacggtat caataccgaa gtgaacaaat aattcaatac cttctttga ttccattgaa      960 aatgcatgat ttgtttcaaa aatcttgcca atcacgccgt ccaccggtgc aacaattttg     1020
tcaccgttcg gacgaatcgc aataccgtcg ccaacgattt tttcagaaaa aaccacatcc     1080
ggtacatctt caatattaac aatttcacct gaaagcggcg cataaatgtc cacttctacg     1140
gttttactat ttttttgaacc aaataattta tcaataagc ccattttta atctcctgaa      1200 tcgacaattt tccgtattct acatgaaaaa catgaatttg tatctaattt aatgtttttt     1260
cagctaaaaa atcagcaact aattttttcaa tttcggcagc agtcggtaat tgcagggctt    1320
tatccgctaa tgcttttgct tcggcaaaat taacactacg aaccaattt ttaatacgag      1380 gaacggaaat agcgctcatg ctgaattcgt ctaatcccat acctaataat aaaatagtgg     1440 cttttcatc accggctaac tcaccgcaca taccagtcca tttgccttcg gtatgagagg      1500
cgtcacgccg tacggccttc ataaaaacga gctacttcag tttcaacttg atcttcagca     1560
attttttgca tatcaagtac aatttttttcc tctttcagaa ctaacgcttt accaaaaacg    1620
atacctggtg aggccgggat tcctgaaatc atgtgtaacc ttccgataat aatttaatta    1680
aaaaaatcta actatgataa acgacatagc cataaaactc ttttattaac agtgataaat    1740
caataagaaa gttttatggc cagacaaatt attctaatgt aggaattaat gcaactaaat    1800
ggtcaacagc attttgctca tcttcgcctt cagctgaaat tgtaattaca gttccttgag    1860
ttaagcctaa agtttgtaat ttgaataaac ttttcgcact tgcactttta ccggcagaag    1920
tcactgttac atcagatgca aacgcttttg cttctttac aaattgtgca gccggacgag      1980
tgtgtaagcc gttaggagct gtaatttcaa catcttttga atacataatt ttacctctaa     2040
tagtaatgtt ttttgttta atgtggagca aacaggtaaa cggttaactt ttgacctgcc     2100
tactaaaatt taattattca taaaccacag cggacactct aaaccatttt gtctgatagt    2160
tcaaaataaa tcttatttag tatcaagatt attcctaatt aattcaagtt aaatcctata    2220 aaacttgag ctagttcatc tttttgtcaa ccgatagatt aatttttaat aaaaatgtaa     2280
caaattagta ataaaaaata accgaattac cttatatcct gctccataaa atggcgttgc    2340
gatttatttt cttcccggct tgaaatcaag cgatggtaat tatcaaatct gacggggtgg    2400
attttcccga gctccacagc ttcccgtaag gcgcagcccg gatcatcaat atgtttgcag    2460
tctctgaatt tgcaggtccc taagaaatat tggaattccc gataaccgtt ggtgatttgt    2520
gcaggttcca aatgccataa accgaactct cgaatgcccg gcgaatcaat cagatttccg    2580
ccctgaggta aatgatataa acgggaagac gtggtggtat gctgtcccaa tcccgaagtt    2640
tcgctgattt caccggtttg cgcattaact tccggtaaaa tatagttgat taaactggac    2700
ttccctaccc cggattgccc gacgaaaatc gacgtaccat ccgctaaaag tgcggtcagt    2760
```

```
ttttccatat tttttccact aatcgccgaa atcattaatg tttcatagcc gattttcgg    2820 tagatttcca gttgttcttc cgcttcccgc cactgttcgt ccgttaataa atcaaccta    2880 ttcaacaaga taacggcagg aatattagcg ttttcacaaa taaccaaata acgatcaata   2940
atattcaggg ataacgccgg tagcaccgac gaaacaataa taatgcgatc gatattcgat   3000
gccattctag actccatagg ccgctttcct ggctttgctt ccagatgtat gctctcctcc   3060
ggagagtacc gtgactttat tttcggcaca aatacagggg tcgatggata aatacggcga   3120
tagtttcctg acggatgatc cgtatgtacc ggcggaagac aagctgcaaa cctgtcagat   3180
ggagattgat ttaatggcgg atgtgctgag agcaccgccc cgtgaatccg cagaactgat   3240
ccgctatgtg tttgcggatg attggccgga ataaataaag ccgggcttaa tacagattaa   3300
gcccgtatag ggtattatta ctgaatacca aacagcttac ggaggacgga atgttaccca   3360
ttgagacaac cagactgcct tctgattatt aatatttttc actattaatc agaaggaata   3420
accatgaatt tacccggat tgacctgaat acctggaatc gcaggaaca ctttgccctt    3480 tatcgtcagc agattaaatg cggattcagc ctgaccacca aactcgatat taccgctttg    3540
cgtaccgcac tggcggagac aggttataag ttttatccgc tgatgattta cctgatctcc   3600
cgggctgtta atcagtttcc ggagttccgg atggcactga agacaatga acttatttac    3660 tgggaccagt cagacccggt ctttactgtc tttcataaag aaaccgaaac attctctgca   3720
ctgtcctgcc gttattttcc ggatctcagt gagtttatgg caggttataa tgcggtaacg   3780
gcagaatatc agcatgatac cagattgttt ccgcagggaa atttaccgga gaatcacctg   3840
aatatatcat cattaccgtg ggtgagtttt gacgggattt aacctgaaca tcaccggaaa   3900
tgatgattat tttgccccgg tttttacgat ggcaaagttt cagcaggaag gtgaccgcgt   3960
attattacct gtttctgtac aggttcatca tgcagtctgt gatggctttc atgcagcacg   4020
gtttattaat acacttcagc tgatgtgtga taacatactg aaataaatta attaattctg   4080
tatttaagcc accgtatccg gcaggaatgg tggctttttt tttatatttt aaccgtaatc   4140
tgtaatttcg tttcagactg gttcaggatg agctcgcttg gactcctgtt gatagatcca   4200
gtaatgacct cagaactcca tctggatttg ttcagaacgc tcggttgccg ccgggcgttt   4260
tttattggtg agaatccaag cactagcggc gcgccggccg gcccggtgtg aaataccgca   4320
cagatgcgta aggagaaaat accgcatcag gcgctcttcc gcttcctcgc tcactgactc   4380
gctgcgctcg gtcgttcggc tgcggcgagc ggtatcagct cactcaaagg cggtaatacg   4440
gttatccaca gaatcagggg ataacgcagg aaagaacatg tgagcaaaag gccagcaaaa   4500
ggccaggaac cgtaaaaagg ccgcgttgct ggcgtttttc cataggctcc gccccctga    4560 cgagcatcac aaaatcgac gctcaagtca gaggtggcga acccgacag gactataaag    4620 ataccaggcg tttccccctg aagctccct cgtgcgctct cctgttccga ccctgccgct    4680
taccggatac ctgtccgcct ttctcccttc gggaagcgtg cgctttctc atagctcacg    4740 ctgtaggtat ctcagttcgg tgtaggtcgt tcgctccaag ctgggctgtg tgcacgaacc   4800
ccccgttcag cccgaccgct gcgccttatc cggtaactat cgtcttgagt ccaacccggt   4860
aagacacgac ttatcgccac tggcagcagc cactggtaac aggattagca gagcgaggta   4920
tgtaggcggt gctacagagt tcttgaagtg gtggcctaac tacggctaca ctagaaggac   4980
agtatttggt atctgcgctc tgctgaagcc agttaccttc ggaaaaagag ttggtagctc    5040
ttgatccggc aaacaaacca ccgctggtag cggtggtttt tttgtttgca agcagcagat   5100
tacgcgcaga aaaaaaggat ctcaagaaga tccttttgatc ttttctacgg ggtctgacgc   5160
```

```
tcagtggaac gaaaactcac gttaagggat tttggtcatg agattatcaa aaaggatctt    5220
cacctagatc cttttaaagg ccggccgcgg ccgccatcgg catttctttt tgcgttttta    5280
tttgttaact gttaattgtc cttgttcaag gatgctgtct ttgacaacag atgttttctt    5340
gcctttgatg ttcagcagga agctcggcgc aaacgttgat tgtttgtctg cgtagaatcc    5400
tctgtttgtc atatagcttg taatcacgac attgtttcct ttcgcttgag gtacagcgaa    5460
gtgtgagtaa gtaaaggtta catcgttagg atcaagatcc atttttaaca caaggccagt    5520
tttgttcagc ggcttgtatg ggccagttaa agaattagaa acataaccaa gcatgtaaat    5580
atcgttagac gtaatgccgt caatcgtcat ttttgatccg cgggagtcag tgaacaggta    5640
ccatttgccg ttcattttaa agacgttcgc gcgttcaatt tcatctgtta ctgtgttaga    5700
tgcaatcagc ggtttcatca cttttttcag tgtgtaatca tcgtttagct caatcatacc    5760
gagagcgccg tttgctaact cagccgtgcg ttttttatcg ctttgcagaa gttttttgact   5820 ttcttgacgg aagaatgatg tgcttttgcc atagtatgct ttgttaaata aagattcttc    5880
gccttggtag ccatcttcag ttccagtgtt tgcttcaaat actaagtatt tgtggccttt    5940
atcttctacg tagtgaggat ctctcagcgt atggttgtcg cctgagctgt agttgccttc    6000
atcgatgaac tgctgtacat tttgatacgt ttttccgtca ccgtcaaaga ttgatttata    6060
atcctctaca ccgttgatgt tcaaagagct gtctgatgct gatacgttaa cttgtgcagt    6120
tgtcagtgtt tgtttgccgt aatgtttacc ggagaaatca gtgtagaata aacggatttt    6180
tccgtcagat gtaaatgtgg ctgaacctga ccattcttgt gtttggtctt ttaggataga    6240
atcatttgca tcgaatttgt cgctgtcttt aaagacgcgg ccagcgtttt tccagctgtc    6300
aatagaagtt tcgccgactt tttgatagaa catgtaaatc gatgtgtcat ccgcattttt    6360
aggatctccg gctaatgcaa agacgatgtg gtagccgtga tagtttgcga cagtgccgtc    6420
agcgttttgt aatggccagc tgtcccaaac gtccaggcct tttgcagaag agatattttt    6480
aattgtggac gaatcaaatt cagaaacttg atattttca ttttttgct gttcagggat     6540 ttgcagcata tcatggcgtg taatatggga aatgccgtat gtttccttat atggcttttg    6600
gttcgtttct ttcgcaaacg cttgagttgc gcctcctgcc agcagtgcgg tagtaaaggt    6660
taatactgtt gcttgttttg caaacttttt gatgttcatc gttcatgtct cctttttat     6720 gtactgtgtt agcggtctgc ttcttccagc cctcctgttt gaagatggca agttagttac    6780
gcacaataaa aaaagaccta aaatatgtaa ggggtgacgc caaagtatac actttgccct    6840
ttacacattt taggtcttgc ctgctttatc agtaacaaac ccgcgcgatt tacttttcga    6900
cctcattcta ttagactctc gtttggattg caactggtct attttcctct tttgtttgat    6960
agaaaatcat aaaaggattt gcagactacg ggcctaaaga actaaaaaat ctatctgttt    7020
cttttcattc tctgtatttt ttatagtttc tgttgcatgg gcataaagtt gccttttaa    7080 tcacaattca gaaatatca taatatctca tttcactaaa taatagtgaa cggcaggtat    7140
atgtgatggg ttaaaaagga tcggcggccg ctcgatttaa atc                       7183
```

<210> SEQ ID NO 23
<211> LENGTH: 7233
<212> TYPE: DNA
<213> ORGANISM: Artificial Sequence
<220> FEATURE:
<223> OTHER INFORMATION: complete nucleotide sequence of plasmid
      pSacB_delta_ptsH

<400> SEQUENCE: 23

```
tcgagccgat actgaagaag tccacttctt ttgctaagaa ttttgcattt actgcagctg    60
acggcgtttc acacattaca ccgatttgaa tattttcatc aaaggcttta ccttcggtgc   120
gtaattcttg ttttaaagtt tcgataacgg atttcaattc gcgaatttct tcaacggaaa   180
taatcatcgg gaacattacc gctaatttac cgaatgcgga agcacgtaat accgcacgca   240
attgagcatt taagatttcg cgacgatcca atgcgatacg aaccgcacgc cagcctaaga   300
acggattcat ttcttttggc agattcatat aaggtaattc tttatctcca ccaatatcca   360
tggtacgtaa taccacctgg cgaccgttca tcgcttctac cacttcttta taagcgataa   420
attgttcttc ttctgaaggc agttggtcac gatccatgaa caggaactcg gtacggtata   480
aaccgacacc ttccgcaccg ttacgatccg caccctcaca gtcacgaatc gtaccgatat   540
tcgccaccac ttcaacacgg tgaccgtcca atgttactgc cggtaaatct tttaatttag   600
ctaattccgc ttttcttcc gctaattttg cttgttgggc ttttaagccg tcaatcacgt   660
cttgagccgg attcacataa acagcgttat tgattgcatc aagtactaaa taatcaccgc   720
tgttaatcat tgcggttgca ttatttgtac ctacaattgc cggtaattcc agcgaacggg   780
ccataataga ggtatgtgaa gtacgaccac cgatatcagt aataaaacct aatactttgt   840
ctaaattcaa ttgtgcggtt tctgatggcg ttaagtcata agcaaccaag attgactctt   900
cattgatttc gcccaaatcc acaattttca tgcctaagat attttaatt aaacggttac   960 cgatatcgcg aatatcgccg gcacgttctt ttaagtactc atcatcaata tccgcaagca  1020
tagcaacttg ttgatcaatg attttacttg ccgcaacgcc cgcatttact ttgtttgaac  1080
gcaaataatc aatgatttct tcttccaact cttcatcttc aagaatcatt aaatgacctt  1140
cgaagatagc cgcttttctt tcaccgagag ttttctctgc acgatctcta atggcgctta  1200
attgttccac tgccgccgta cggccttcat aaaaacgagc tacttcagtt tcaacttgat  1260
cttcagcaat tttttgcata tcaagtacaa ttttttcctc tttcagaact aacgctttac  1320
caaaaacgat acctggtgag gccgggattc ctgaaatcat gtgtaacctt ccgataataa  1380
tttaattaaa aaaatctaac tatgataaac gacatagcca taaaactctt ttattaacag  1440
tgataaatca ataagaaagt tttatggcca gacaaattat tctaatgtag gaattaatgc  1500
aactaaatgg tcaacagcat tttgctcatc ttcgccttca acctctaata gtaatgtttt  1560
ttgttttaat gtggagcaaa caggtaaacg gttaactttt gacctgccta ctaaaattta  1620
attattcata aaccacagcg gacactctaa accattttgt ctgatagttc aaaataaatc  1680
ttatttagta tcaagattat tcctaattaa ttcaagttaa atcctataaa aacttgagct  1740
agttcatctt tttgtcaacc gatagattaa tttttaataa aaatgtaaca aattagtaat  1800
aaaaaataac cgaattacct tatatcctgc tccataaaat ggcgttgcga tttattttct  1860
tcccggcttg aaatcaagcg atggtaatta tcaaatctga cggggtggat tttcccgagc  1920
tccacagctt cccgtaaggc gcagcccgga tcatcaatat gtttgcagtc tctgaatttg  1980
caggtcccta agaaatattg gaattcccga taaccgttgg tgatttgtgc aggttccaaa  2040
tgccataaac cgaactctcg aatgcccggc gaatcaatca gatttccgcc ctgaggtaaa  2100
tgatataaac gggaagacgt ggtggtatgc tgtcccaatc ccgaagtttc gctgatttca  2160
ccggtttgcg cattaacttc cggtaaaata tagttgatta aactggactt ccctaccccg  2220
gattgcccga cgaaaatcga cgtaccatcc gctaaaagtg cggtcagttt ttccatattt  2280
tttccactaa tcgccgaaat cattaatgtt tcatagccga ttttcggta gatttccagt  2340
```

```
tgttcttccg cttcccgcca ctgttcgtcc gttaataaat caaccttatt caacaagata   2400
acggcaggaa tattagcgtt ttcacaaata accaaataac gatcaataat attcagggat   2460
aacgccggta gcaccgacga acaataata atgcgatcga tattcgatgc catgactttc   2520
agtccgtcat aataatccgg gcgggcaatt tcattttcac gcggtttaat cgcctcaatg   2580
accccgctaa taccctgtag tttttcatgc cctcggcgcc acactacgtg atctcccacc   2640
accacattgg ctaatgtgcg acgtaaatta caacggaaaa tctcgccttg actattctcc   2700
acatccgcat gcatagaata acgagtgacg acaacgccgt cttgcgtatc gccaagcatt   2760
tcttcctgcc aatcaatctc ttttttact cttcggtgat gacgatccaa tgcttttaca   2820
ttatttgaat gaattcgacg tttttgattt tgagttaatt tacgcttagt caaacagaag   2880
tccttaaagt gcggtagatt ttcgtataat attacgggtc aacaaatcag ttaacgtata   2940
aatgcttata ggatactcca aattatgcaa ttagataacc aaaatctaat ctggatcgac   3000
ttagaaatga ccgggttaga ccctgaaaac gagcgcatta ttgaaatcgc caccatctag   3060
actccatagg ccgcttctcct ggctttgctt ccagatgtat gctctcctcc ggagagtacc   3120
gtgactttat tttcggcaca aatacagggg tcgatggata aatacggcga tagtttcctg   3180
acggatgatc cgtatgtacc ggcggaagac aagctgcaaa cctgtcagat ggagattgat   3240
ttaatggcgg atgtgctgag agcaccgccc cgtgaatccg cagaactgat ccgctatgtg   3300
tttgcggatg attggccgga ataaataaag ccgggcttaa tacagattaa gcccgtatag   3360
ggtattatta ctgaatacca aacagcttac ggaggacgga atgttaccca ttgagacaac   3420
cagactgcct tctgattatt aatatttttc actattaatc agaaggaata accatgaatt   3480
ttacccggat tgacctgaat acctggaatc gcagggaaca ctttgcccctt tatcgtcagc   3540 agattaaatg cggattcagc ctgaccacca aactcgatat taccgctttg cgtaccgcac   3600
tggcggagac aggttataag ttttatccgc tgatgattta cctgatctcc cgggctgtta   3660
atcagtttcc ggagttccgg atggcactga agacaatga acttatttac tgggaccagt   3720
cagacccggt ctttactgtc tttcataaag aaaccgaaac attctctgca ctgtcctgcc   3780
gttattttcc ggatctcagt gagtttatgg caggttataa tgcggtaacg gcagaatatc   3840
agcatgatac cagattgttt ccgcagggaa atttaccgga gaatcacctg aatatatcat   3900
cattaccgtg ggtgagtttt gacgggattt aacctgaaca tcaccggaaa tgatgattat   3960
tttgccccgg ttttttacgat ggcaaagttt cagcaggaag gtgaccgcgt attattacct   4020
gtttctgtac aggttcatca tgcagtctgt gatggctttc atgcagcacg gtttattaat   4080
acacttcagc tgatgtgtga taacatactg aaataaatta attaattctg tatttaagcc   4140
accgtatccg gcaggaatgg tggcttttttt tttataattt aaccgtaatc tgtaatttcg   4200
tttcagactg gttcaggatg agctcgcttg gactcctgtt gatagatcca gtaatgacct   4260
cagaactcca tctggatttg ttcagaacgc tcggttgccg ccgggcgttt tttattggtg   4320
agaatccaag cactagcggc gcgccggccg gcccggtgtg aaataccgca cagatgcgta   4380
aggagaaaat accgcatcag gcgctcttcc gcttcctcgc tcactgactc gctgcgctcg   4440
gtcgttcggc tgcggcgagc ggtatcagct cactcaaagg cggtaatacg ttatccaca   4500 gaatcagggg ataacgcagg aaagaacatg tgagcaaaag gccagcaaaa ggccaggaac   4560
cgtaaaaagg ccgcgttgct ggcgtttttc cataggctcc gcccccctga cgagcatcac   4620
aaaaatcgac gctcaagtca gaggtggcga aacccgacag gactataaag ataccaggcg   4680
tttccccctg gaagctccct cgtgcgctct cctgttccga ccctgccgct taccggatac   4740
```

```
ctgtccgcct ttctcccttc gggaagcgtg gcgctttctc atagctcacg ctgtaggtat   4800
ctcagttcgg tgtaggtcgt tcgctccaag ctgggctgtg tgcacgaacc ccccgttcag   4860
cccgaccgct gcgccttatc cggtaactat cgtcttgagt ccaacccggt aagacacgac   4920
ttatcgccac tggcagcagc cactggtaac aggattagca gagcgaggta tgtaggcggt   4980
gctacagagt tcttgaagtg gtggcctaac tacggctaca ctagaaggac agtatttggt   5040
atctgcgctc tgctgaagcc agttaccttc ggaaaaagag ttggtagctc ttgatccggc   5100
aaacaaacca ccgctggtag cggtggtttt tttgtttgca agcagcagat tacgcgcaga   5160
aaaaaaggat ctcaagaaga tcctttgatc ttttctacgg ggtctgacgc tcagtggaac   5220
gaaaactcac gttaagggat tttggtcatg agattatcaa aaaggatctt cacctagatc   5280
cttttaaagg ccgccgcgg ccgccatcgg cattttcttt tgcgttttta tttgttaact   5340
gttaattgtc cttgttcaag gatgctgtct ttgacaacag atgttttctt gcctttgatg   5400
ttcagcagga agctcggcgc aaacgttgat tgtttgtctg cgtagaatcc tctgtttgtc   5460
atatagcttg taatcacgac attgttttcct ttcgcttgag gtacagcgaa gtgtgagtaa   5520
gtaaaggtta catcgttagg atcaagatcc attttttaaca caaggccagt tttgttcagc   5580
ggcttgtatg ggccagttaa agaattagaa acataaccaa gcatgtaaat atcgttagac   5640
gtaatgccgt caatcgtcat ttttgatccg cgggagtcag tgaacaggta ccatttgccg   5700
ttcattttaa agacgttcgc gcgttcaatt tcatctgtta ctgtgttaga tgcaatcagc   5760
ggtttcatca cttttttcag tgtgtaatca tcgtttagct caatcatacc gagagcgccg   5820
tttgctaact cagccgtgcg ttttttatcg ctttgcagaa gttttttgact ttcttgacgg   5880
aagaatgatg tgcttttgcc atagtatgct tgttaaaata aagattcttc gccttggtag   5940
ccatcttcag ttccagtgtt tgcttcaaat actaagtatt tgtggccttt atcttctacg   6000
tagtgaggat ctctcagcgt atggttgtcg cctgagctgt agttgccttc atcgatgaac   6060
tgctgtacat tttgatacgt ttttccgtca ccgtcaaaga ttgatttata atcctctaca   6120
ccgttgatgt tcaaagagct gtctgatgct gatacgttaa cttgtgcagt tgtcagtgtt   6180
tgtttgccgt aatgtttacc ggagaaatca gtgtagaata aacggatttt tccgtcagat   6240
gtaaatgtgg ctgaacctga ccattcttgt gtttggtctt ttaggataga atcatttgca   6300
tcgaatttgt cgctgtcttt aaagacgcgg ccagcgtttt tccagctgtc aatagaagtt   6360
tcgccgactt tttgatagaa catgtaaatc gatgtgtcat ccgcattttt aggatctccg   6420
gctaatgcaa agacgatgtg gtagccgtga tagtttgcga cagtgccgtc agcgttttgt   6480
aatggccagc tgtcccaaac gtccaggcct tttgcagaag atatttttt aattgtggac   6540
gaatcaaatt cagaaacttg atatttttca tttttttgct gttcagggat ttgcagcata   6600
tcatggcgtg taatatggga aatgccgtat gttttccttat atggcttttg gttcgtttct   6660
ttcgcaaacg cttgagttgc gcctcctgcc agcagtgcgg tagtaaaggt taatactgtt   6720
gcttgttttg caaactttt gatgttcatc gttcatgtct cctttttat gtactgtgtt   6780
agcggtctgc ttcttccagc cctcctgttt gaagatggca agttagttac gcacaataaa   6840
aaaagaccta aatatgtaa ggggtgacgc caaagtatac actttgccct ttacacattt   6900
taggtcttgc ctgctttatc agtaacaaac ccgcgcgatt tacttttcga cctcattcta   6960
ttagactctc gtttggattg caactggtct attttcctct tttgtttgat agaaaatcat   7020
aaaaggattt gcagactacg ggcctaaaga actaaaaaat ctatctgttt cttttcattc   7080
```

```
tctgtatttt ttatagtttc tgttgcatgg gcataaagtt gcctttttaa tcacaattca    7140
gaaaatatca taatatctca tttcactaaa taatagtgaa cggcaggtat atgtgatggg    7200
ttaaaaagga tcggcggccg ctcgatttaa atc                                 7233
```

The invention claimed is:

1. A modified microorganism of the family Pasteurellaceae having, compared to its wildtype, a reduced activity of the enzyme encoded by the ptsA-gene (energy coupling Enzyme I of phosphoenolpyruvate-dependent phosphotransferase system), wherein the reduction of the activity of the enzyme encoded by the ptsA-gene is achieved by a deletion of the ptsA-gene, wherein the ptsA-gene comprises a nucleic acid selected from the group consisting of
- a1) nucleic acids having the nucleotide sequence of SEQ ID NO: 3;
- b1) nucleic acids encoding the amino acid sequence of SEQ ID NO: 4;
- c1) nucleic acids which are at least 90% identical to the nucleic acid of a1) or b1), the identity being the identity over the total length of the nucleic acids of a1) or b1);
- d1) nucleic acids encoding an amino acid sequence which is at least 90% identical to the amino acid sequence encoded by the nucleic acid of a1) or b1), the identity being the identity over the total length of amino acid sequence encoded by the nucleic acids of a1) or b1); and
- e1) nucleic acids encoding the same protein as any of the nucleic acids of a1) or b1), but differing from the nucleic acids of a1) or b1) above due to the degeneracy of the genetic code;

and wherein the wildtype refers to the microorganism whose genome is present in a state as before the introduction of the modification of the ptsA-gene.

2. Modified microorganism according to claim 1, wherein the modified microorganism belongs to the genus *Basfia*.

3. Modified microorganism according to claim 1, wherein the microorganism comprises at least one of the following genetic modifications A) to D):
- A) a deletion of the ldhA-gene (gene encoding lactate dehydrogenase);
- B) a deletion of the pflA-gene (gene encoding an activator of pyruvate formate lyase) or a deletion of the pflD-gene (gene encoding pyruvate formate lyase);
- C) an introduction of at least one mutation into the wcaJ-gene (gene encoding UDP-glucose:undecaprenyl-phosphate glucose-1-phosphate transferase) that leads to the expression of a truncated enzyme encoded by the wcaJ-gene; and
- D) an introduction of at least one mutation into the pykA-gene (gene encoding pyruvate kinase).

4. A method of producing an organic compound comprising:
- I) cultivating the modified microorganism according to claim 1 in a culture medium comprising at least one assimilable carbon source to allow the modified microorganism to produce the organic compound, thereby obtaining a fermentation broth comprising the organic compound;
- II) recovering the organic compound from the fermentation broth obtained in process step I).

5. Method according to claim 4, wherein the organic compound is succinic acid.

6. Method according to claim 4, wherein at least 50 wt.-% of the assimilable carbon source, based on the total weight of the assimilable carbon source with the exception of carbon dioxide, is sucrose.

7. Method according to claim 4, wherein the process further comprises the process step:
- III) conversion of the organic compound contained in the fermentation broth obtained in process step I) or conversion of the recovered organic compound obtained in process step II) into a secondary organic product being different from the organic compound by at least one chemical reaction.

8. Method according to claim 7, wherein the organic compound is succinic acid and wherein the secondary organic product is selected from the group consisting of succinic acid esters or polymers thereof, tetrahydrofuran (THF), 1,4-butanediol (BDO), gamma-butyrolactone (GBL) and pyrrolidones.

* * * * *